(12) United States Patent
Snyder et al.

(10) Patent No.: US 9,174,988 B2
(45) Date of Patent: Nov. 3, 2015

(54) SMALL MOLECULE INHIBITORS OF HEPATITIS C VIRUS

(75) Inventors: John K. Snyder, Harvard, MA (US); Wanguo Wei, San Diego, CA (US); Feng Ni, Allston, MA (US); Arthur Donny Strosberg, Palm Beach, FL (US); Eliane Leuwenkroon, legal representative, Palm Beach, FL (US); Smitha Kota, Wellington, FL (US); Virginia Ngocthanh Takahashi, Rockville, MD (US)

(73) Assignees: TRUSTEES OF BOSTON UNIVERSITY, Boston, MA (US); THE SCRIPPS RESEARCH INSTITUTE, La Jolla, CA (US)

( * ) Notice: Subject to any disclaimer, the term of this patent is extended or adjusted under 35 U.S.C. 154(b) by 135 days.

(21) Appl. No.: 13/504,822

(22) PCT Filed: Oct. 27, 2010

(86) PCT No.: PCT/US2010/054220
§ 371 (c)(1),
(2), (4) Date: Nov. 20, 2012

(87) PCT Pub. No.: WO2011/056630
PCT Pub. Date: May 12, 2011

(65) Prior Publication Data
US 2013/0065875 A1    Mar. 14, 2013

Related U.S. Application Data

(60) Provisional application No. 61/279,856, filed on Oct. 27, 2009.

(51) Int. Cl.
*A61P 31/12* (2006.01)
*C07D 471/18* (2006.01)
*C07D 471/22* (2006.01)
*C07D 487/18* (2006.01)

(52) U.S. Cl.
CPC ............ *C07D 471/18* (2013.01); *C07D 471/22* (2013.01); *C07D 487/18* (2013.01)

(58) Field of Classification Search
CPC ... C07D 471/18; C07D 471/22; C07D 487/18
USPC ................ 514/210.02, 287; 546/64; 544/125; 540/362
See application file for complete search history.

(56) References Cited

U.S. PATENT DOCUMENTS

2008/0287449 A1    11/2008    Niu et al.

OTHER PUBLICATIONS

Wei, W., et al., "New small molecule inhibitors of hepatitis C virus," Bioorganic & Medicinal Chemistry Letters, vol. 19, No. 24, pp. 6926-6930.

*Primary Examiner* — Paul V Ward
(74) *Attorney, Agent, or Firm* — Nixon Peabody LLP

(57) ABSTRACT

The invention provides derivatives and analogs of triazatetracyclo[7.7.0.0$^{1,13}$.0$^{2,7}$]-hexadeca-2,4,6,10,12-pentaenes, 5,7,11-triazatetracyclo[8.7.0.0$^{1,6}$.0$^{12,17}$]-heptadeca-6,8,12, 14,16-pentaenes, pharmaceutical compositions comprising these compounds and methods for treatment of hepatitis C viral infections using these compounds.

9 Claims, 8 Drawing Sheets

SMALL MOLECULE INHIBITORS OF HEPATITIS C VIRUS

CROSS REFERENCE TO RELATED APPLICATION

This application is a 35 U.S.C. §371 National Phase Entry Application of International Application No. PCT/US2010/054220 filed Oct. 27, 2010, which designates the U.S., and which claims benefit under 35 U.S.C. §119(e) of the U.S. provisional application No. 61/279,856 filed Oct. 27, 2009, the content of which is incorporated herein by reference in its entirety.

GOVERNMENT SUPPORT

This invention was made with government support under grant nos. GM067041, GM076263 and GM086180 awarded by the National Institutes of Health. The government has certain rights in the invention.

FIELD OF THE INVENTION

The invention relates to compositions and methods for inhibiting hepatitis C virus (HCV) core dimerization. The compositions and methods of the invention also relate to treatment of HCV infection.

BACKGROUND OF THE INVENTION

Hepatitis C virus (HCV) is a single stranded positive RNA virus belonging to the flaviviridae family. Infection by HCV is the main cause of chronic liver disease with over 170 million people infected worldwide. See, for example, Rosenberg, S. *J. Mo. Biol.* (2001) 313: 451 and Giannini, C.; Brechot, C. *Cell Death Differ.* (2003) 10: S27. Over three million Americans are infected by the HCV virus, which is particularly lethal for AIDS patients (http://www.cdc.gov/hepatitis/Statistics.htm#section1), of whom increasing numbers are co-infected with HIV and HCV (McGovern, B. H. *J. Acquir. Immune Defic. Syndr.* (2007) 45: S47). Nearly 40,000 new cases of HCV are reported yearly in this country, 20% of whom will develop liver cirrhosis, and up to 2.5% of these patients will develop hepatocellular-carcinoma. There is no vaccine for HCV, and the only treatment, a combination of interferon-α and ribavirin, is successful in less than half of the patients. See for example, Simmonds, P. J. *J. Gen. Virol.* (2004) 85: 3173 and Cristina, J.; del Pilar Moreno, M.; Moratorio, G. *Virus Res.* (2007) 127: 185. Until recently, the main efforts to develop novel HCV inhibitors has been on the viral protease and polymerase enzymes, but escape mutants have already been reported. See Courcameck, et al., *Antivir. Ther.* (2006) 11: 847 and DeFrancesco, R.; Caffi, A. *Adv. Drug Delivery Rev.* (2007) 59: 1242.

The HCV RNA enodes a polyprotein which is co- and post-translationally processed into ten individual proteins by host cell signal peptidases and viral peptidases (Bartenschlager, R.; Lohmann, V. *J. Gen. Virol.* (2000) 81: 1631). All ten proteins are essential for viral infectivity. One of these proteins, known as "core", is a 191 amino acid capsid protein which is required for viral assembly within the host cell following post-translational processing (Santolini, E.; Migliaccio, G.; La Monica, N. *J. Virol.* (1994) 68: 3631). Core is the most conserved of all HCV proteins, across the 6 major genotypes, and that it is the least variable of the ten HCV proteins in variant viruses emerging constantly in patients. As such, core has emerged as a viable target for drug therapy against HCV (Strosberg, A. D.; Kota, S.; Takahashi, V.; Snyder, J. K.; Mousseau, G. *Viruses* (2010) 2: 1734).

SUMMARY OF THE INVENTION

In one aspect, the invention provides a compound of formula (I):

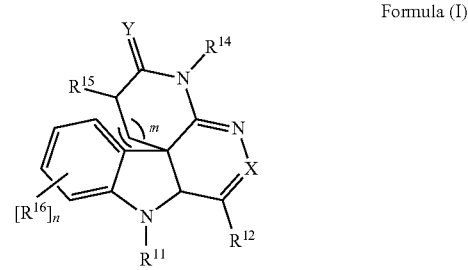

Formula (I)

wherein:
X is $CR^{13}$ or N;
Y is O or S;
$R^{11}$ is H, $C(O)R^{17}$, $CO_2R^{17}$, $S(O)R^{17}$, $S(O)_2R^{17}$, alkyl, alkenyl, alkynyl, acyl, aryl, heteroaryl, cyclyl, heterocyclyl, each of which can be optionally substituted, or $R^{11}$ is a linker that links two compounds of formula (I) together;
$R^{12}$ and $R^{13}$ are independently for each occurrence H, halogen, $N(R^{17})_2$, $NO_2$, $OR^{17}$, $CF_3$, CN, $C(O)R^{17}$, $CO_2R^{17}$, $SO_3R^{17}$, $SR^{17}$, $S(O)R^{17}$, $S(O)_2R^{17}$, $CH(CO_2R^{17})_2$, alkyl, alkenyl, alkynyl, acyl, aryl, heteroaryl, cyclyl or heterocyclyl, each of which can be optionally substituted;
$R^{14}$ is $C(O)R^{17}$, $CO_2R^{17}$, $C(O)N(R^{17})_2$, $S(O)R^{17}$, $S(O)_2R^{17}$, alkyl, alkenyl, alkynyl, acyl, aryl, heteroaryl, cyclyl, heterocyclyl, each of which can be optionally substituted;
$R^{15}$ is H, halogen, $CF_3$, CN, $—(CH_2)_tOR^{17}$ (t is 1, 2, 3, 4, 5, 6, 7, 8, 9 or 10), $C(O)R^{17}$, $CO_2R^{17}$, $OR^{17}$, $SR^{17}$, $S(O)R^{17}$, $S(O)_2R^{17}$, alkyl, alkenyl, alkynyl, aryl, heteroaryl, cyclyl, heterocyclyl, each of which can be optionally substituted;
$R^{16}$ is independently for each occurrence halogen, $N(R^{17})_2$, $NO_2$, $OR^{17}$, $CF_3$, CN, $C(O)R^{17}$, $CO_2R^{17}$, $SO_3R^{17}$, $SR^{17}$, $S(O)R^{17}$, $S(O)_2R^{17}$, $CH(CO_2R^{17})_2$, alkyl, alkenyl, alkynyl, acyl, aryl, heteroaryl, cyclyl or heterocyclyl, each of which can be optionally substituted;
$R^{17}$ is independently for each occurrence H, alkyl, alkenyl, alkynyl, acyl, aryl, heteroaryl, cyclyl, or heterocyclyl, each of which can be optionally substituted
m is 1, 2, or 3;
n is 0, 1, 2, 3, or 4; and
analogs, derivatives, isomers, prodrugs and pharmaceutically acceptable salts thereof, a compound of formula (II):

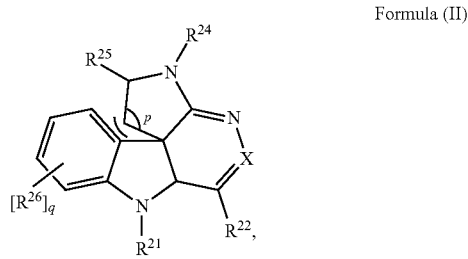

Formula (II)

wherein:

X is $CR^{22}$ or N;

$R^{21}$ is H, $C(O)R^{27}$, $COR^{27}S(O)R^{27}$, $S(O)_2R^{27}$, alkyl, alkenyl, alkynyl, acyl, aryl, heteroaryl, cyclyl, heterocyclyl, each of which can be optionally substituted, or $R^{21}$ is a linker that links two compounds of formula (II) together;

$R^{22}$ and $R^{23}$ are independently for each occurrence H, halogen, $N(R^{27})_2$, $NO_2$, $OR^{27}$, $CF_3$, CN, $C(O)R^{27}$, $CO_2R^{27}$, $SO_3R^{27}$, $SR^{27}$, $S(O)R^{27}$, $S(O)_2R^{27}$, $CH(CO_2R^{27})_2$, alkyl, alkenyl, alkynyl, acyl, aryl, heteroaryl, cyclyl or heterocyclyl, each of which can be optionally substituted;

$R^{24}$ is $C(O)R^{27}$, $CO_2R^{27}$, $C(O)N(R^{27})_2$, $S(O)R^{27}$, $S(O)_2R^{27}$, alkyl, alkenyl, alkynyl, acyl, aryl, heteroaryl, cyclyl, heterocyclyl, each of which can be optionally substituted;

$R^{25}$ is halogen, $CF_3$, CN, $—(CH_2)_tOR^{27}$ (t is 1, 2, 3, 4, 5, 6, 7, 8, 9 or 10), $C(O)R^{27}$, $CO_2R^{27}$, $OR^{27}$, $SR^{27}$, $S(O)R^{27}$, $S(O)_2R^{27}$, alkyl, alkenyl, alkynyl, aryl, heteroaryl, cyclyl, heterocyclyl, each of which can be optionally substituted;

$R^{26}$ is independently for each occurrence halogen, $N(R^{27})_2$, $NO_2$, $OR^{27}$, $CF_3$, CN, $C(O)R^{27}$, $CO_2R^{27}$, $SO_3R^{27}$, $SR^{27}$, $S(O)R^{27}$, $S(O)_2R^{27}$, $CH(CO_2R^{27})_2$, alkyl, alkenyl, alkynyl, acyl, aryl, heteroaryl, cyclyl or heterocyclyl, each of which can be optionally substituted;

$R^{27}$ is independently for each occurrence H, alkyl, alkenyl, alkynyl, acyl, aryl, heteroaryl, cyclyl, or heterocyclyl, each of which can be optionally substituted p is 1, 2, 3, or 4;

q is 0, 1, 2, 3, or 4; and analogs, derivatives, isomers, prodrugs and pharmaceutically acceptable salts thereof, a compound of formula (III):

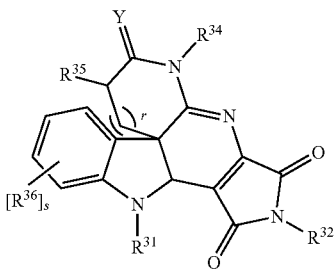

Formula (III)

wherein:

Y is O or S $R^{31}$ is H, $C(O)R^{37}$, $CO_2R^{37}$, $S(O)R^{37}$, $S(O)_2R^{37}$, alkyl, alkenyl, alkynyl, acyl, aryl, heteroaryl, cyclyl, heterocyclyl, each of which can be optionally substituted, or $R^{31}$ is a linker that links two compounds of formula (III) together;

$R^{32}$ is H, halogen, $N(R^{37})_2$, $NO_2$, $OR^{37}$, $CF_3$, CN, $C(O)R^{37}$, $—(CH_2)_tOR^{37}$ (t is 1, 2, 3, 4, 5 or 6), $CO_2R^{37}$, $SO_3R^{37}$, $SR^{37}$, $S(O)R^{37}$, $S(O)_2R^{37}$, $CH(CO_2R^{37})_2$, alkyl, alkenyl, alkynyl, acyl, aryl, heteroaryl, cyclyl or heterocyclyl, each of which can be optionally substituted;

$R^{34}$ is $C(O)R^{37}$, $CO_2R^{37}$, $C(O)N(R^{37})_2$, $S(O)R^{37}$, $S(O)_2R^{37}$, alkyl, alkenyl, alkynyl, acyl, aryl, heteroaryl, cyclyl, heterocyclyl, each of which can be optionally substituted;

$R^{35}$ is H, halogen, $CF_3$, CN, $—(CH_2)_tOR^{17}$ (t is 1, 2, 3, 4, 5, 6, 7, 8, 9 or 10), $C(O)R^{17}$, $CO_2R^{17}$, $OR^{17}$, $SR^{17}$, $S(O)R^{17}$, $S(O)_2R^{17}$, alkyl, alkenyl, alkynyl, aryl, heteroaryl, cyclyl, heterocyclyl, each of which can be optionally substituted;

$R^{36}$ is independently for each occurrence halogen, $N(R^{37})_2$, $NO_2$, $OR^{37}$, $CF_3$, CN, $C(O)R^{37}$, $CO_2R^{37}$, $SO_3R^{37}$, $SR^{37}$, $S(O)_R^{37}$, $S(O)_2R^{37}$, $CH(CO_2R^{37})_2$, alkyl, alkenyl, alkynyl, acyl, aryl, heteroaryl, cyclyl or heterocyclyl, each of which can be optionally substituted;

$R^{37}$ is independently for each occurrence H, alkyl, alkenyl, alkynyl, acyl, aryl, heteroaryl, cyclyl, or heterocyclyl, each of which can be optionally substituted r is 1, 2, or 3;

s is 0, 1, 2, 3, or 4; and analogs, derivatives, stereoisomers and pharmaceutically acceptable salts thereof, or a compound of formula (IV):

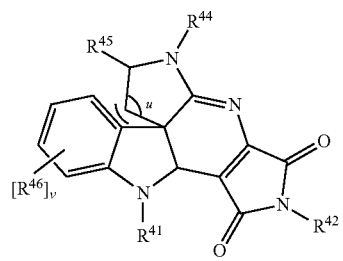

Formula (IV)

wherein:

$R^{41}$ is H, $C(O)R^{47}$, $CO_2R^{47}$, $S(O)R^{47}$, $S(O)_2R^{47}$, alkyl, alkenyl, alkynyl, acyl, aryl, heteroaryl, cyclyl, heterocyclyl, each of which can be optionally substituted, or $R^{41}$ is a linker that links two compounds of formula (IV) together;

$R^{42}$ is H, halogen, $N(R^{47})_2$, $NO_2$, $OR^{47}$, $CF_3$, CN, $C(O)R^{47}$, $—(CH_2)_tOR^{47}$ (t is 1, 2, 3, 4, 5 or 6), $CO_2R^{47}$, $SO_3R^{47}$, $SR^{47}$, $S(O)R^{47}$, $S(O)_2R^{47}$, $CH(CO_2R^{47})_2$, alkyl, alkenyl, alkynyl, acyl, aryl, heteroaryl, cyclyl or heterocyclyl, each of which can be optionally substituted;

$R^{44}$ is H, $C(O)R^{47}$, $CO_2R^{47}$, $C(O)N(R^{47})_2$, $S(O)R^{47}$, $S(O)_2R^{47}$, alkyl, alkenyl, alkynyl, acyl, aryl, heteroaryl, cyclyl, heterocyclyl, each of which can be optionally substituted;

$R^{45}$ is halogen, $CF_3$, CN, $—(CH_2)_tOR^{47}$ (t is 1, 2, 3, 4, 5, 6, 7, 8, 9 or 10), $C(O)R^{47}$, $CO_2R^{47}$, $OR^{47}$, $SR^{47}$, $S(O)R^{47}$, $S(O)_2R^{47}$, alkyl, alkenyl, alkynyl, aryl, heteroaryl, cyclyl, heterocyclyl, each of which can be optionally substituted;

$R^{46}$ is independently for each occurrence halogen, $N(R^{47})_2$, $NO_2$, $OR^{47}$, $CF_3$, CN, $C(O)R^{47}$, $CO_2R^{47}$, $SO_3R^{47}$, $SR^{47}$, $S(O)_R^{47}$, $S(O)_2R^{47}$, $CH(CO_2R^{47})_2$, alkyl, alkenyl, alkynyl, acyl, aryl, heteroaryl, cyclyl or heterocyclyl, each of which can be optionally substituted;

$R^{47}$ is independently for each occurrence H, alkyl, alkenyl, alkynyl, acyl, aryl, heteroaryl, cyclyl, or heterocyclyl, each of which can be optionally substituted u is 1, 2, 3, or 4;

v is 0, 1, 2, 3, or 4; and analogs, derivatives, isomers and pharmaceutically acceptable salts thereof.

In another aspect, the invention provides a method of treating a viral infection or preventing a disease or disorder caused by a viral infection in a subject in need thereof, the method comprising administering to the subject a therapeutically effective amount of a compound described herein, e.g., a compound of formula (I)-(IV), analogs, derivatives, isomers, prodrugs and pharmaceutically acceptable salts thereof.

In yet another aspect, the invention provides a method of inhibiting hepatitis core dimerization in a cell, the method comprising contacting a cell with a compound of formula (I)-(IV), or an analog, a derivative, an isomer, a prodrug or a pharmaceutically acceptable salt thereof.

In still yet another aspect, the invention provides a pharmaceutical composition comprising a compound of formula (I)-(IV) and a pharmaceutically acceptable carrier.

DETAILED DESCRIPTION OF THE INVENTION

Figure 1:
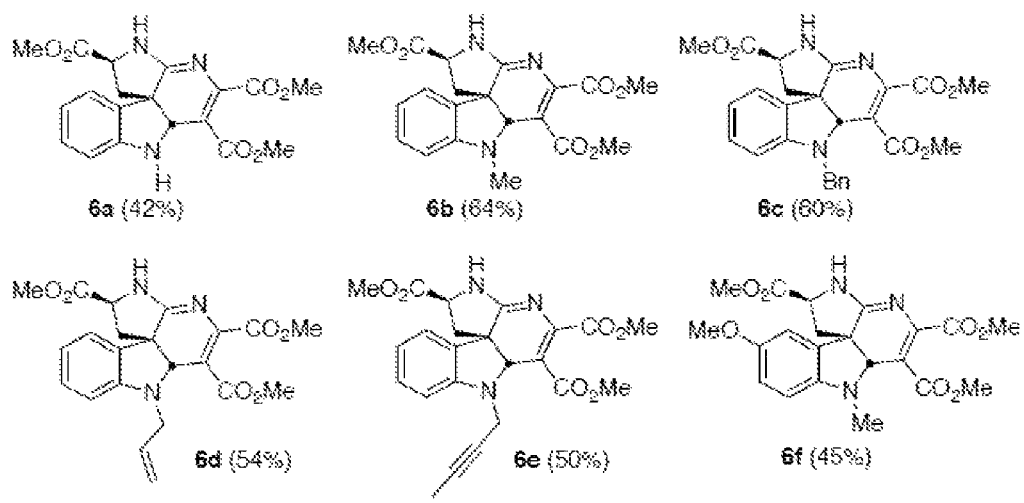
FIG. 1 shows scaffolds (6) for library preparation (overall yield in parentheses).
Figure 2:
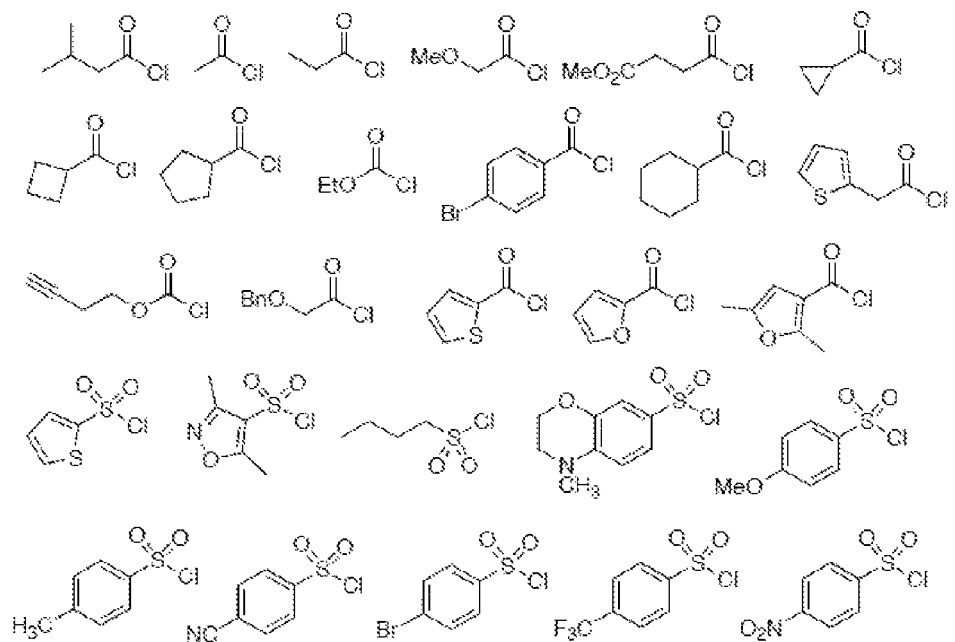
FIG. 2 shows acid chlorides and sulfonyl chlorides used to diversify the scaffolds of 6 at N-14.

In one aspect, the invention provides a compound of formula (I)-(IV): and:

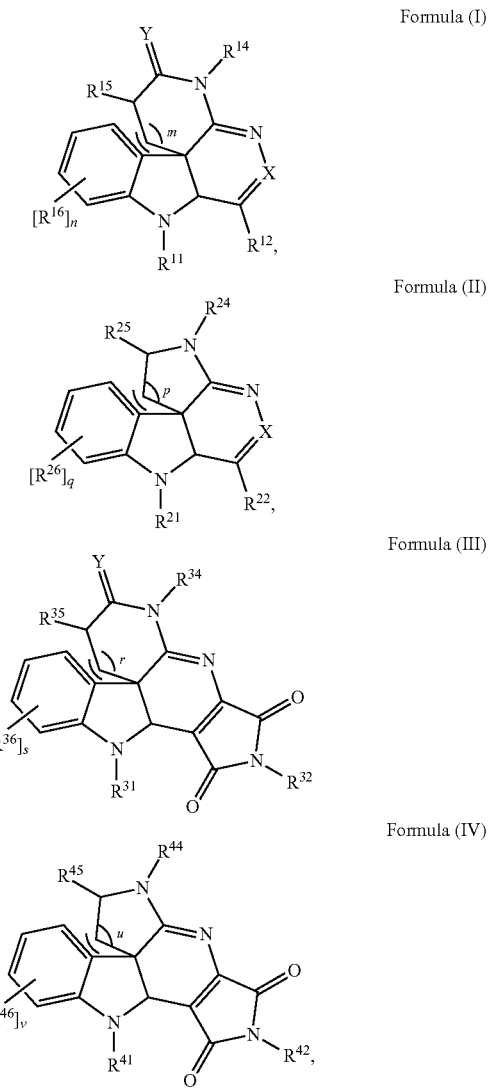

wherein variables are as defined above, and analogs, derivatives, isomers, prodrugs and pharmaceutically acceptable salts thereof.

Compounds of Formula (I)

In some embodiments, Y is O.

In some embodiments, X is $CR^{13}$.

In some embodiments, m is 1, e.g., the lactam is a δ-lactam.

In some embodiments, $R^{11}$ is H, alkyl, alkenyl, or alkynyl. In some further embodiments of this $R^{11}$ is selected from the group consisting of H, methyl, ethyl, propyl, butyl, pentyl, hexyl, allyl, but-2-ynyl, 3-methyl-but-2ynyl, benzyl, phenyl, and terminal alkyne, e.g., hept-6-ynyl.

In some embodiments, $R^{11}$ is

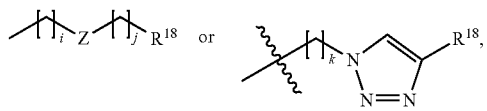

wherein i, j and k are independently an integer from 1 to 10 (e.g., 1, 2, 3, 4, 5, 6, 7, 8, 9, or 10); Z is O, S, NH or $CH_2$; and $R^{18}$ is optionally substituted alkyl, optionally substituted alkenyl, optionally substituted aryl, optionally substituted heteroaryl, optionally substituted cyclyl, or optionally substituted heterocyclyl. In some further embodiments of this k is 5. In some other embodiments, of this $R^{18}$ is

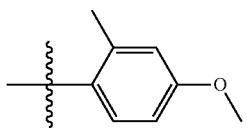

or $-CH_2NHC(O)CH_3$.

In some embodiments, at least one of $R^{12}$ and $R^{13}$ (e.g., $R^{12}$ only, $R^{13}$ only, or both $R^{12}$ and $R^{13}$) can be independently selected from the group consisting of $CO_2R^{17}$, $CF_3$, $SR^{17}$, CN, $CH(CO_2(R^{17})_2)_2$, aryl, heteroaryl and any combinations thereof. In some further embodiments of this, both of $R^{12}$ and $R^{13}$ are $CO_2R^{17}$. When $R^{12}$ or $R^{13}$ comprise a $R^{17}$ substituent, $R^{17}$ can be an $C_1$-$C_6$ alkyl. Preferably $R^{17}$ is methyl, ethyl, propyl, butyl, pentyl, or t-butyl. A preferred aryl is 4-nitrophenyl, which may be optionally substituted.

In some embodiments, at least one of $R^{12}$ and $R^{13}$ is $CF_3$ and the other is aryl or heteroaryl. In one further embodiment of this $R^{12}$ is $CF_3$ and $R^{13}$ is aryl or heteroaryl.

In some embodiments, $R^{14}$ is selected from the group consisting of

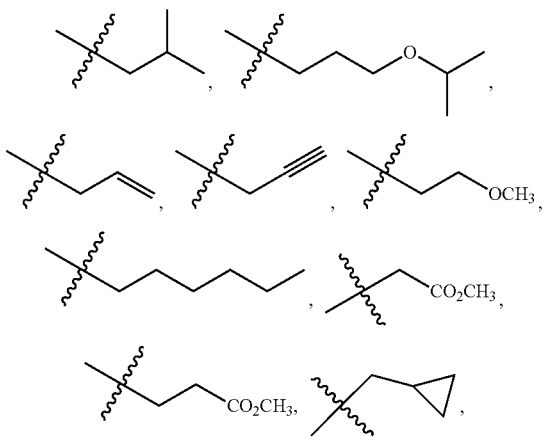

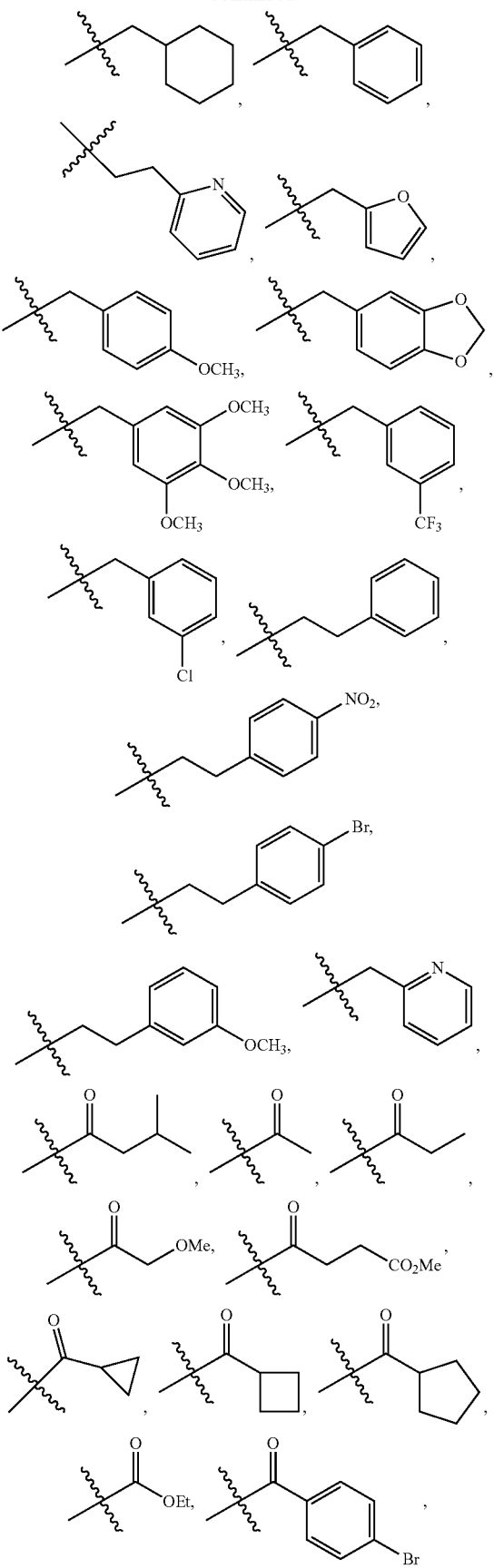

-continued

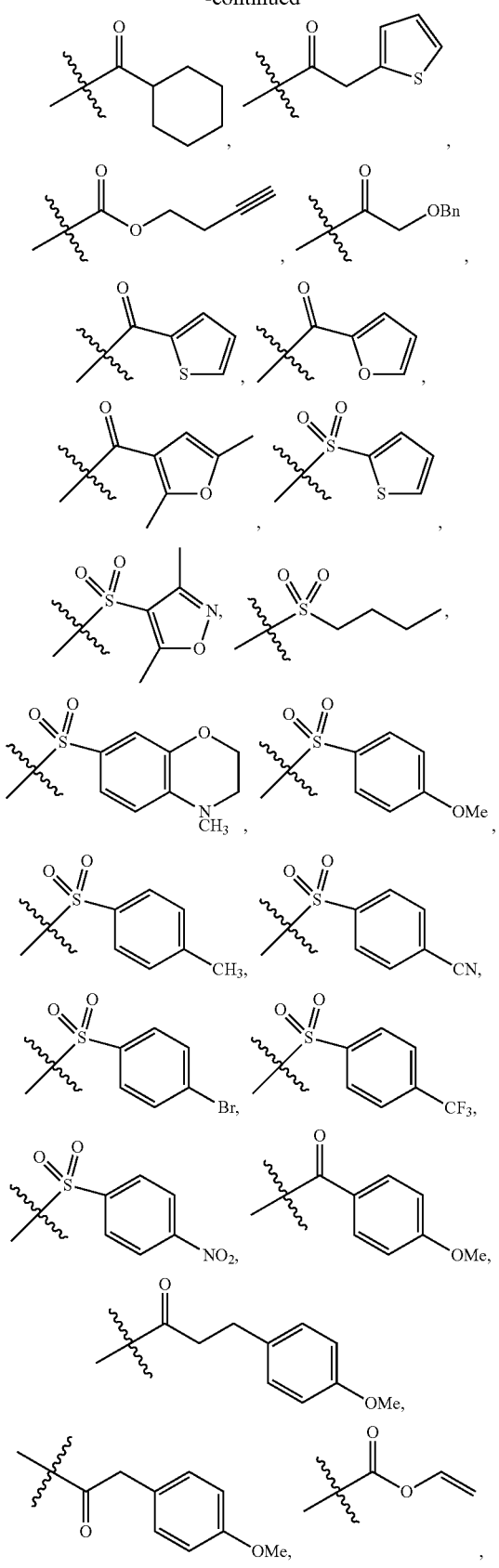

and any combinations thereof.

In some embodiments, $R^{15}$ is H.

In some embodiments, $R^{16}$ is selected from the group consisting of $OR^{17}$, $N(R^{17})_2$, F, Br, I, Cl, CN, $NO_2$, $CF_3$, $-C{\equiv}CCH_2CH_2CH_2CH_2CH_2CH_3$, $-C{\equiv}CCH_2CH_2CH_3$, $-C{\equiv}CCH_2CH_2OH$,

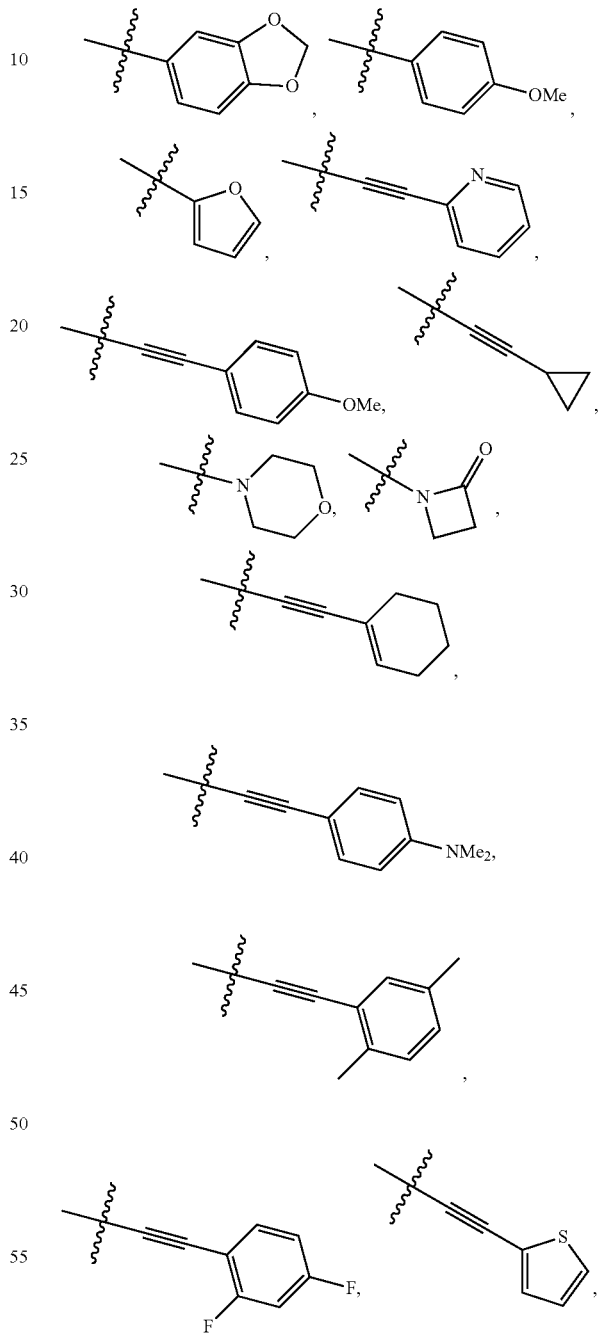

and any combinations thereof. When $R^{16}$ comprises a $R^{17}$ substituent, $R^{17}$ can be a $C_1$-$C_6$ alkyl. Preferably $R^{17}$ is methyl, ethyl, propyl, butyl, pentyl, or t-butyl.

While all isomers of the compounds of claim 1 are claimed, the following two isomers are specifically illustrated. Accordingly, in some embodiments, the compound of formula (I) is of formula (Ia) or (Ib):

Formula (Ia)

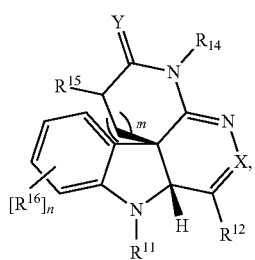

Formula (I)

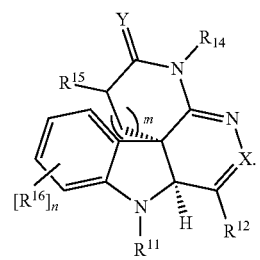

In some embodiments, n is 0 or 1. When n is 1, a preferred compound of formula (I) has the structure of formula (Ic):

Formula (Ic)

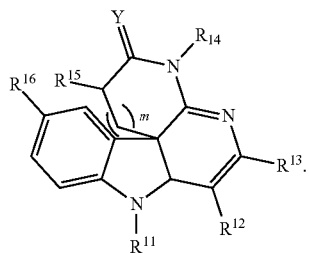

In some embodiments, a compound of formula (I) has the structure shown in formula (Id):

Formula (Id)

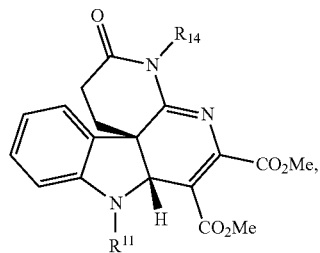

wherein:

$R^{11}$ is —$CH_3$, —$CH_2CH=CH_2$, —$CH_2CH=C(CH_3)_2$, —$CH_2Ph$, or —$CH_2C\equiv CCH_3$, and $R^{14}$ is 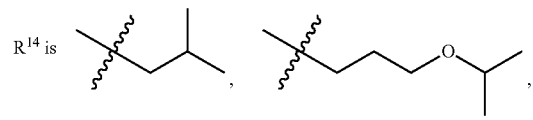,

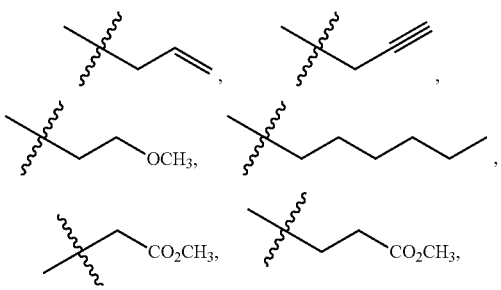

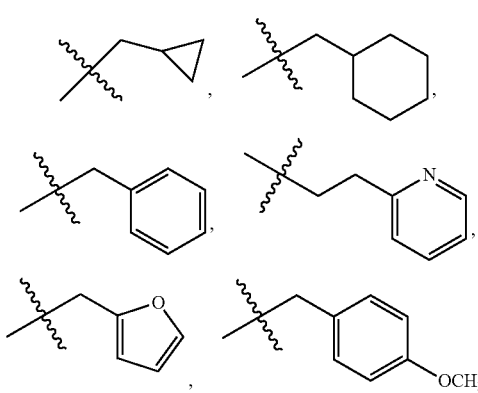

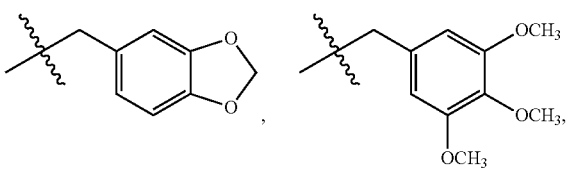

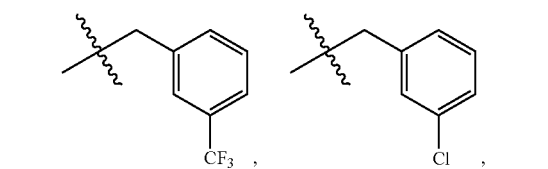

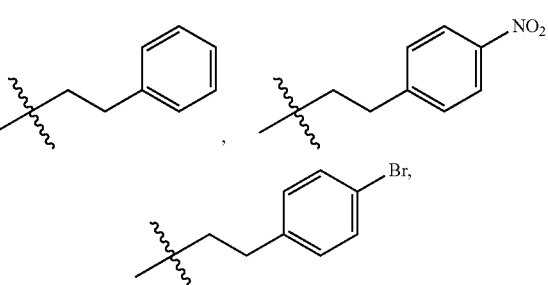

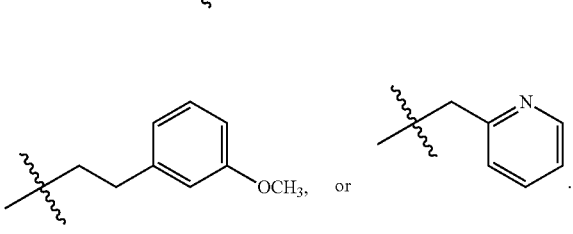 or

The compounds of formula (Id) are members of library 14 as exemplified in Example 2 herein.

In some embodiments, compounds of formula (I) do not include those compounds described in Benson et al., Tetrahedron (2000) 56: 1165-1180, content of which is herein incorporated by reference.

In some embodiments, a compound of formula (I) does not include

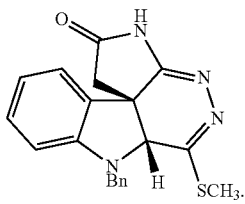 [SMILES: CSC1=NN=C2NC(=O)C[C@@]23c2ccccc2N(Cc2ccccc2)[C@@H]13]

Compounds of Formula (II)

In some embodiments, p is 1.
In some embodiments, X is $CR^{23}$.
In some embodiments, $R^{21}$ is H, alkyl, alkenyl, or alkynyl. In some further embodiments of this $R^{21}$ is selected from the group consisting of H, methyl, ethyl, propyl, butyl, pentyl, hexyl, allyl, but-2-ynyl, 3-methyl-but-2ynyl, benzyl, phenyl, and terminal alkyne, e.g., hept-6-ynyl.
In some embodiments, $R^{21}$ is

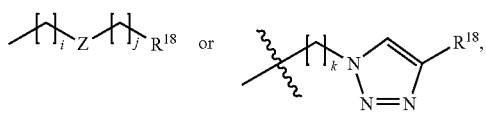

wherein i, j and k are independently an integer from 1 to 10 (e.g., 1, 2, 3, 4, 5, 6, 7, 8, 9, or 10); Z is O, S, NH or $CH_2$; and $R^{18}$ is optionally substituted alkyl, optionally substituted alkenyl, optionally substituted aryl, optionally substituted heteroaryl, optionally substituted cyclyl, or optionally substituted heterocyclyl. In some further embodiments of this k is 5. In some other embodiments, of this $R^{18}$ is

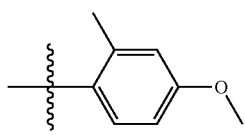 [SMILES: *c1ccc(OC)cc1C]

or —$CH_2NHC(O)CH_3$.

In some embodiments, at least one of $R^{22}$ and $R^{23}$ (e.g., $R^{22}$ only, $R^{23}$ only, or both $R^{22}$ and $R^{23}$) can be independently selected from the group consisting of $CO_2R^{27}$, $CF_3$, $SR^{27}$, CN, $CH(CO_2(R^{27})_2)_2$, aryl, heteroaryl and any combinations thereof. In some further embodiments of this, both of $R^{22}$ and $R^{23}$ are $CO_2R^{27}$. When $R^{22}$ or $R^{23}$ comprise a $R^{27}$ substituent, $R^{27}$ can be an $C_1$-$C_6$ alkyl. Preferably $R^{27}$ is methyl, ethyl, propyl, butyl, pentyl, or t-butyl. A preferred aryl is 4-nitrophenyl, which may be optionally substituted.

In some embodiments, at least one of $R^{22}$ and $R^{23}$ is $CF_3$ and the other is aryl or heteroaryl. In one further embodiment of this $R^{12}$ is $CF_3$ and $R^{13}$ is aryl or heteroaryl.

In some embodiments, $R^{24}$ is selected from the group consisting of

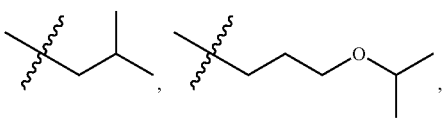

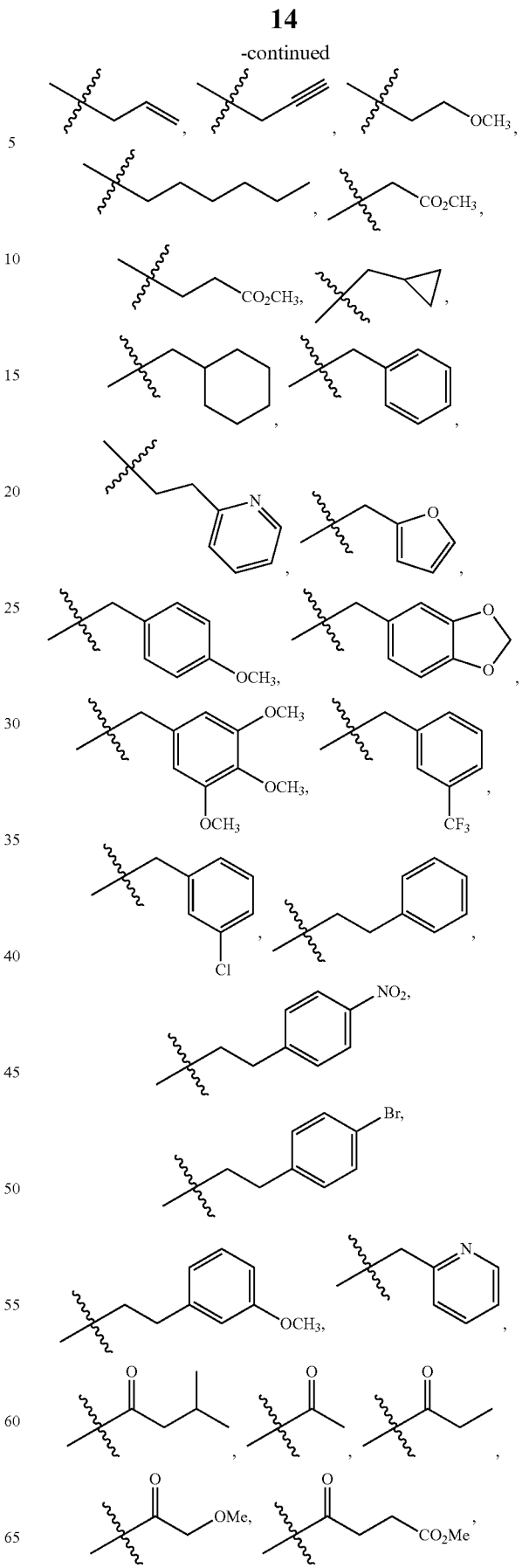

-continued

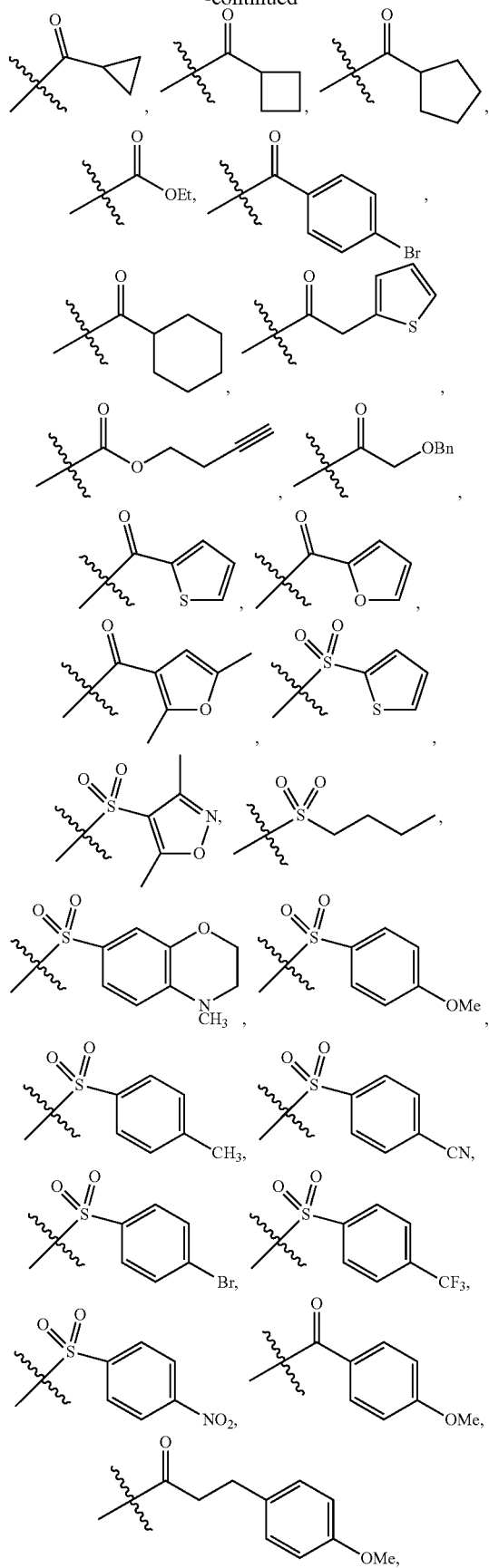

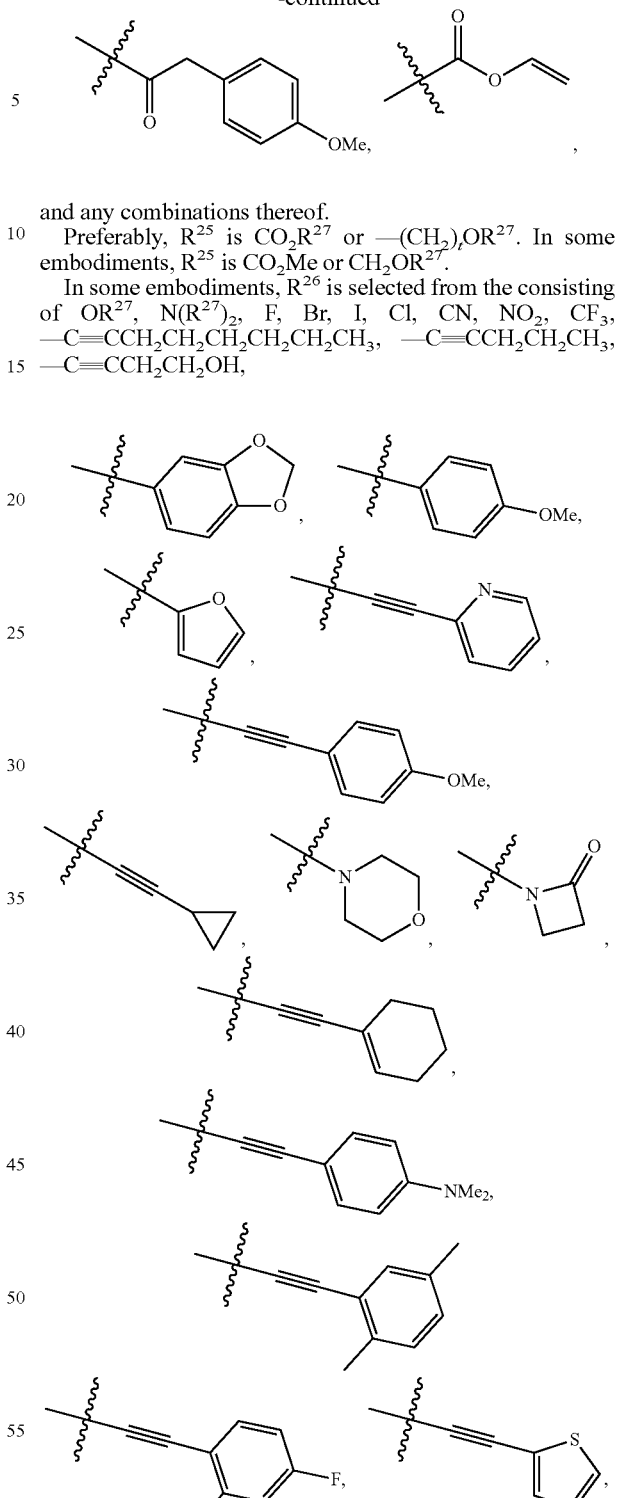

and any combinations thereof.

Preferably, $R^{25}$ is $CO_2R^{27}$ or $-(CH_2)_tOR^{27}$. In some embodiments, $R^{25}$ is $CO_2Me$ or $CH_2OR^{27}$.

In some embodiments, $R^{26}$ is selected from the consisting of $OR^{27}$, $N(R^{27})_2$, F, Br, I, Cl, CN, $NO_2$, $CF_3$, $-C\equiv CCH_2CH_2CH_2CH_2CH_2CH_3$, $-C\equiv CCH_2CH_2CH_3$, $-C\equiv CCH_2CH_2OH$, and any combinations thereof. When $R^{26}$ comprises a $R^{27}$ substituent, $R^{27}$ can be a $C_1$-$C_6$ alkyl. Preferably $R^{17}$ is methyl, ethyl, propyl, butyl, pentyl, or t-butyl.

While all isomers of the compounds of formula (II) are claimed, the following two isomers are specifically illustrated. Accordingly, in some embodiments, the compound of formula (II) is of formula (IIa) or (IIb):

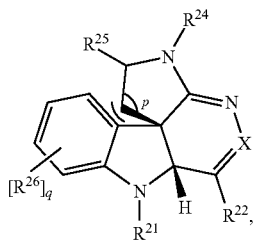
Formula (IIa)
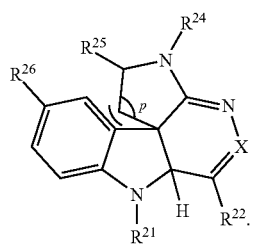
Formula (IIb)
In some embodiments, q is 0 or 1. When q is 1, a preferred compound of formula (II) has the structure of formula (IIc):
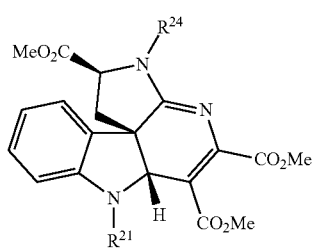
Formula (IIc)
In some embodiments, a compound of formula (II) has a structure as shown in formula (IId):
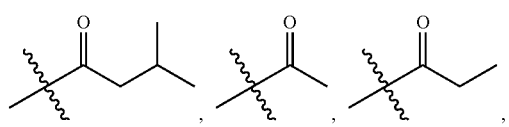
Formula (IId)
wherein:
$R^{21}$ is H, —$CH_3$, —$CH_2CH=CH_2$, —$CH_2C≡CCH_3$, or —$CH_2Ph$; and
$R^{24}$ is
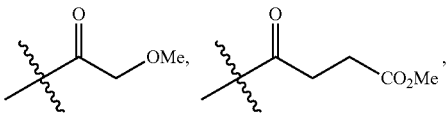
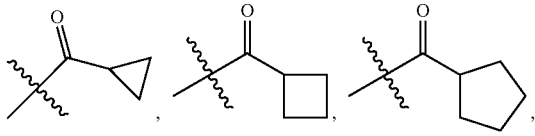
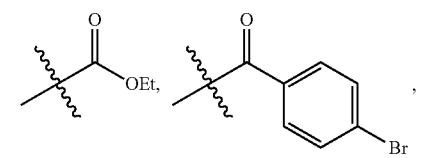
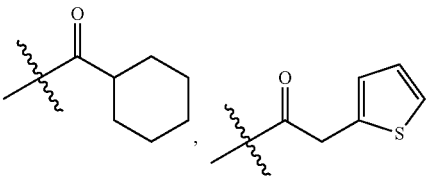
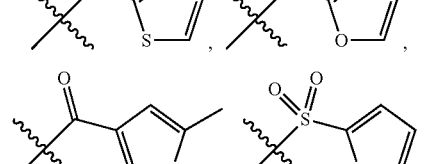
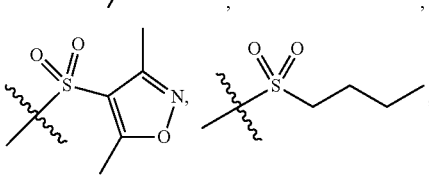
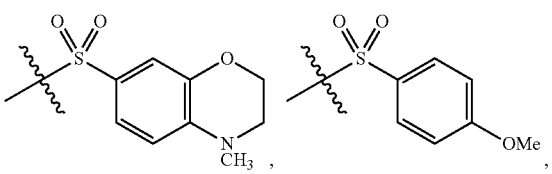
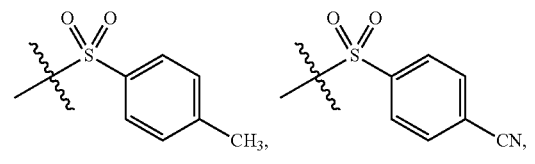
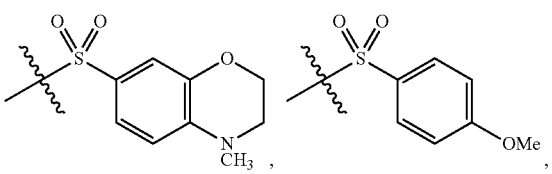
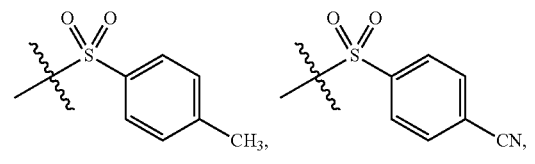
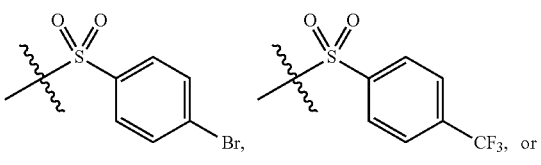

-continued

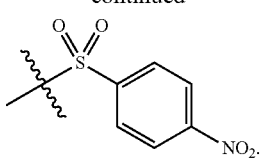

In some embodiments, a compound of formula (II) has a structure as shown in formula (IIe):

Formula (IIe)

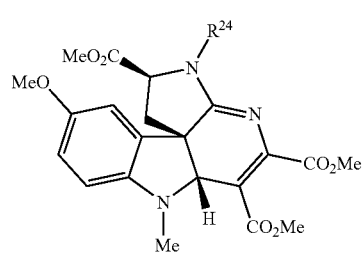

wherein:

$R^{24}$ is

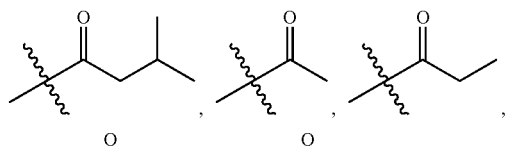

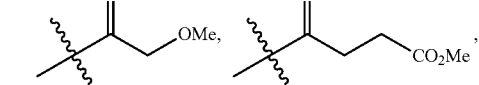

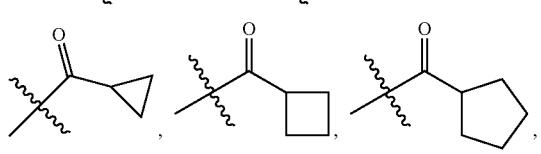

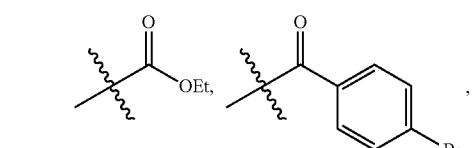

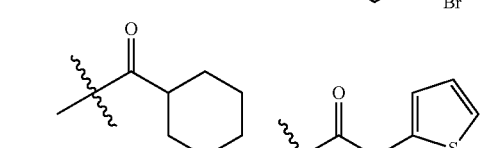

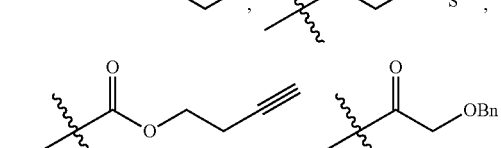

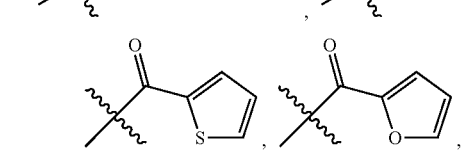

-continued

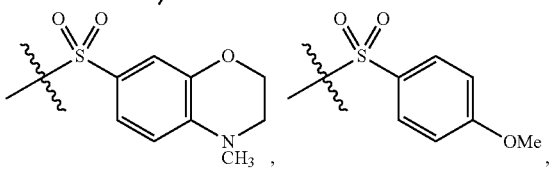

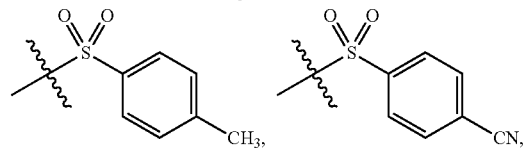

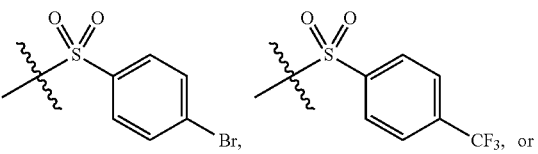

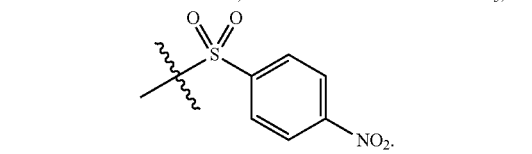

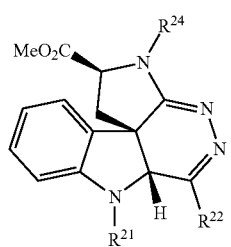

The compounds of formula (IId) and (IIe) are members of library 7 as exemplified in Example 1 herein.

In some embodiments, a compound of formula (II) has a structure shown in formula (IIf):

Formula (IIf)

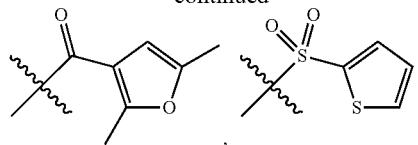

wherein:

$R^{21}$ is H, —CH$_3$, —CH$_2$Ph, —CH$_2$CH=CH$_2$, or —CH$_2$C≡CCH$_3$;

$R^{22}$ is SMe, Me, CN, or —CH(CO$_2$CH$_3$)$_2$: and $R^{24}$ is

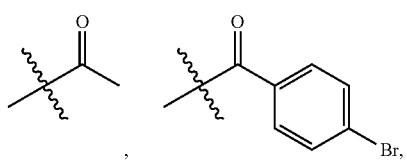

-continued

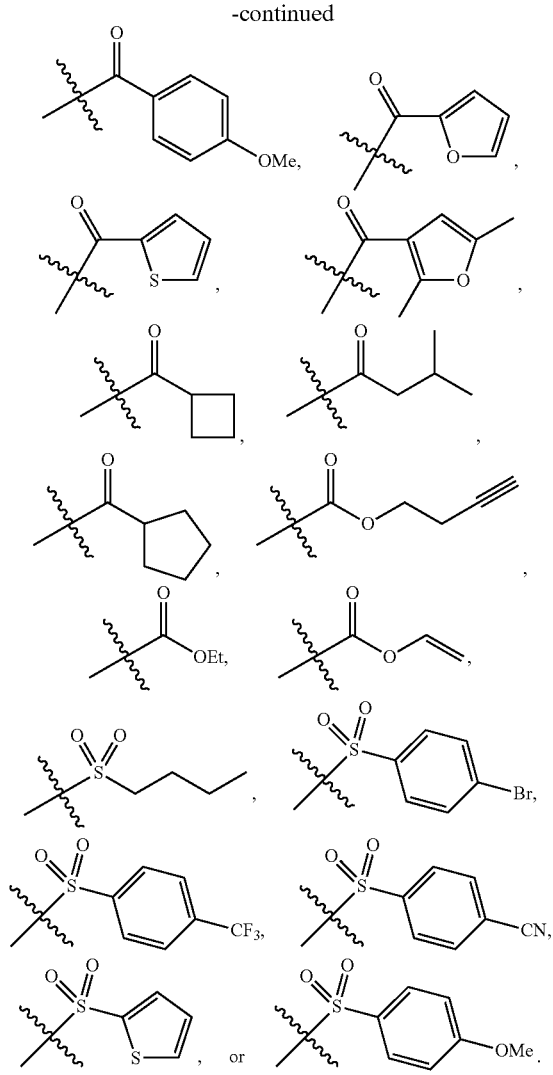

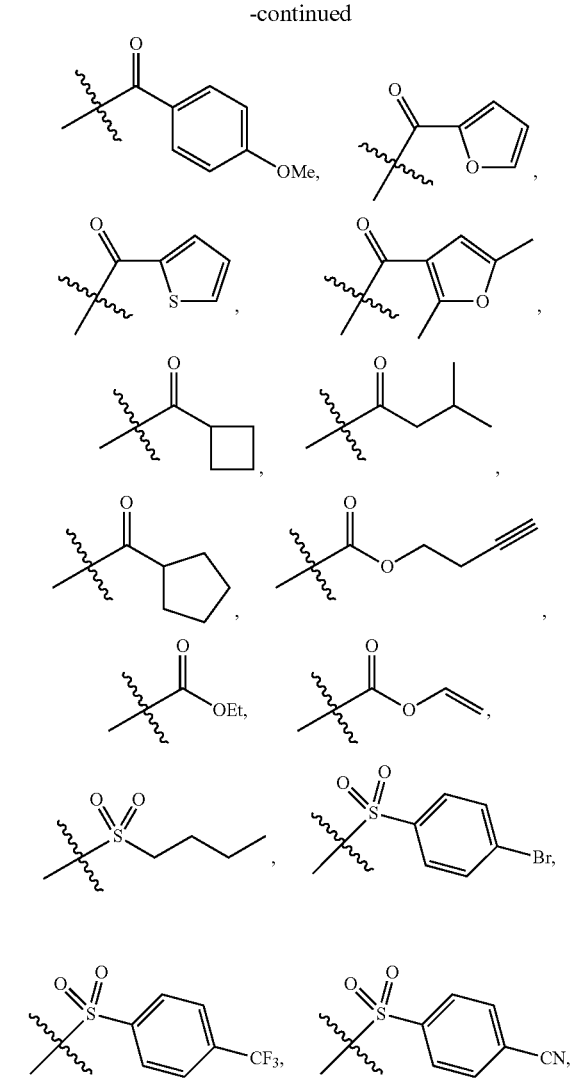

In some embodiments, a compound of formula (II) has a structure shown in formula (IIg):

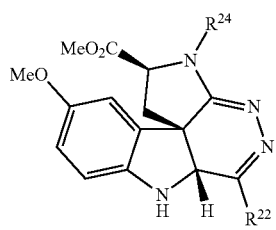

Formula (IIg)

wherein:
$R^{22}$ is SMe, Me, CN, or —CH(CO$_2$CH$_3$)$_2$: and
$R^{24}$ is

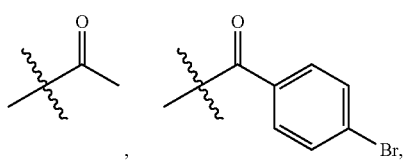

In some embodiments, compounds of formula (II) do not include those compounds described in Benson et al., Tetrahedron (2000) 56: 1165-1180, content of which is herein incorporated by reference.

In some embodiments, a compound of formula (II) does not include

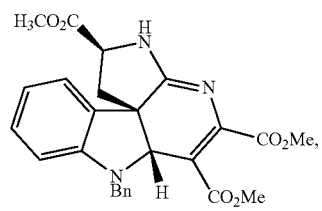

-continued

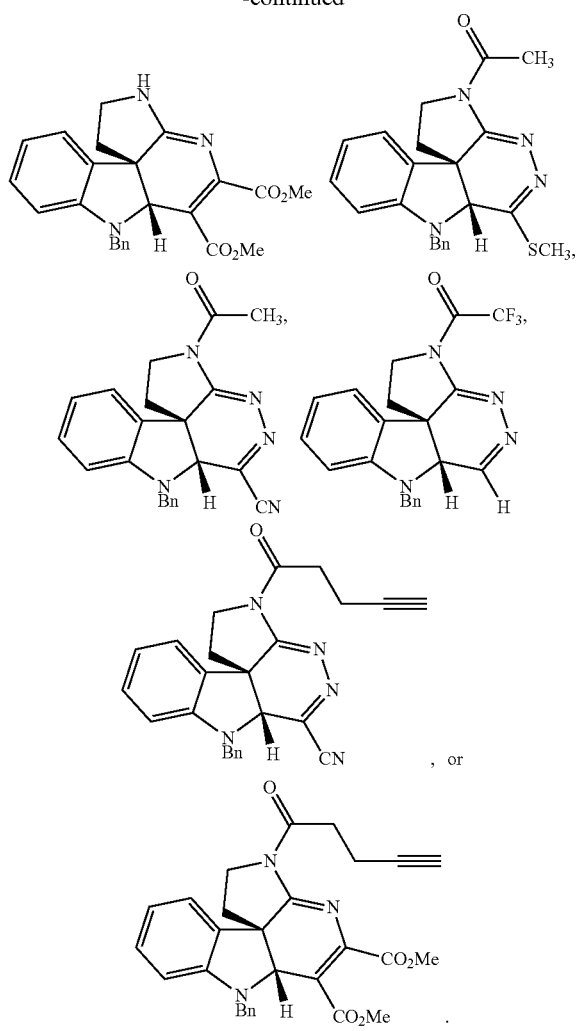

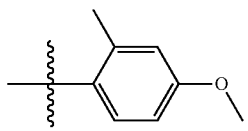

or —CH$_2$NHC(O)CH$_3$.

R$^{32}$ can be selected from the group consisting of alky, aryl, heteroaryl, each of which can be optionally substituted. In some embodiments, R$^{32}$ is

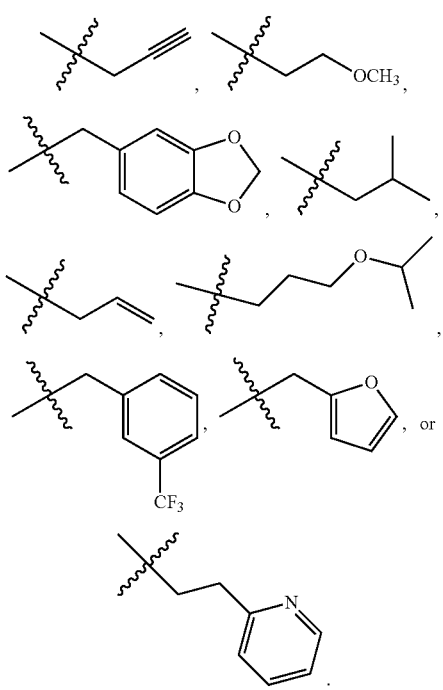

Compounds of Formula (III)

In some embodiments, Y is O.

In some embodiments, r is 1.

In some embodiments, R$^{31}$ is H, alkyl, alkenyl, or alkynyl. In some further embodiments of this R$^{21}$ is selected from the group consisting of H, methyl, ethyl, propyl, butyl, pentyl, hexyl, allyl, but-2-ynyl, 3-methyl-but-2ynyl, benzyl, phenyl, and terminal alkyne, e.g., hept-6-ynyl.

In some embodiments, R$^{31}$ is

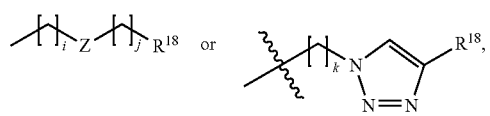

wherein i, j and k are independently an integer from 1 to 10 (e.g., 1, 2, 3, 4, 5, 6, 7, 8, 9, or 10); Z is O, S, NH or CH$_2$; and R$^{18}$ is optionally substituted alkyl, optionally substituted alkenyl, optionally substituted aryl, optionally substituted heteroaryl, optionally substituted cyclyl, or optionally substituted heterocyclyl. In some further embodiments of this k is 5. In some other embodiments, of this R$^{18}$ is Similar to compounds of formula (I), R$^{34}$ can be selected from the group consisting of

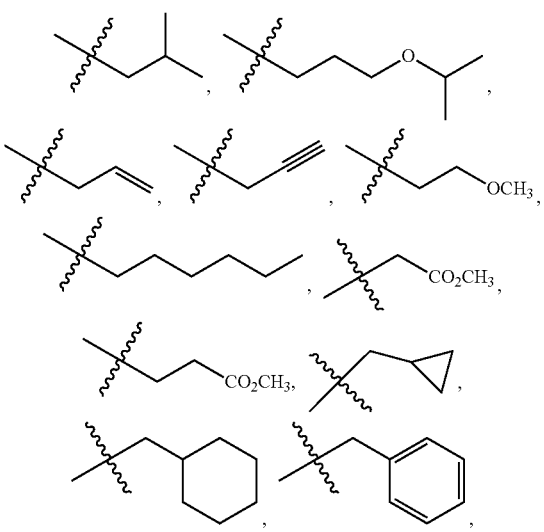

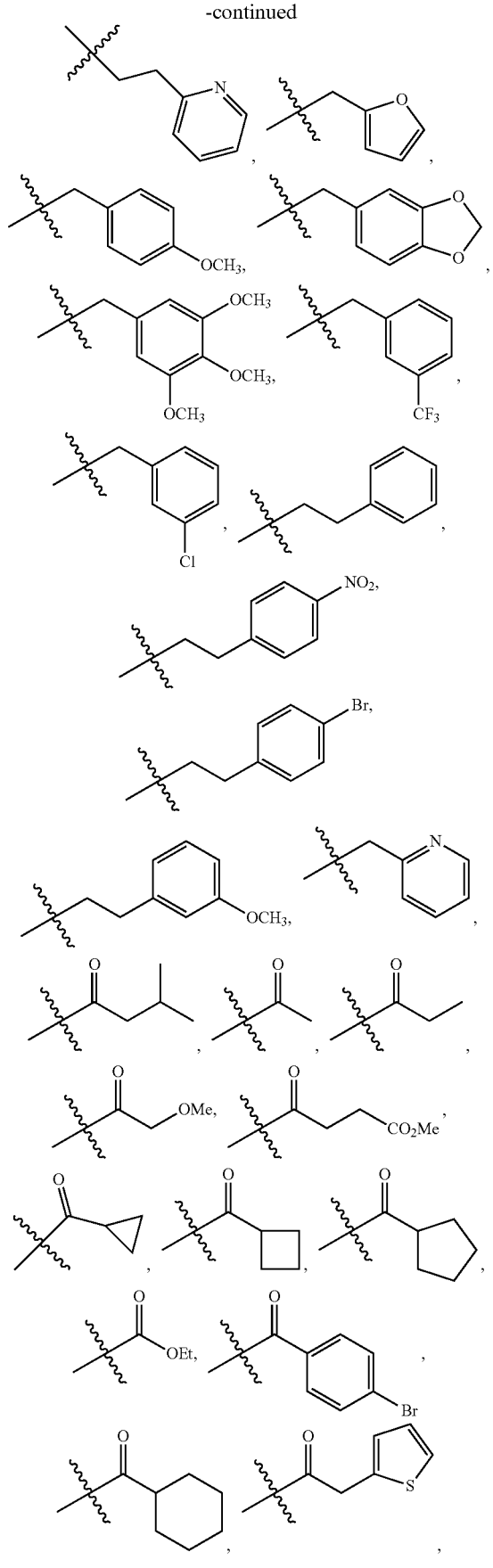
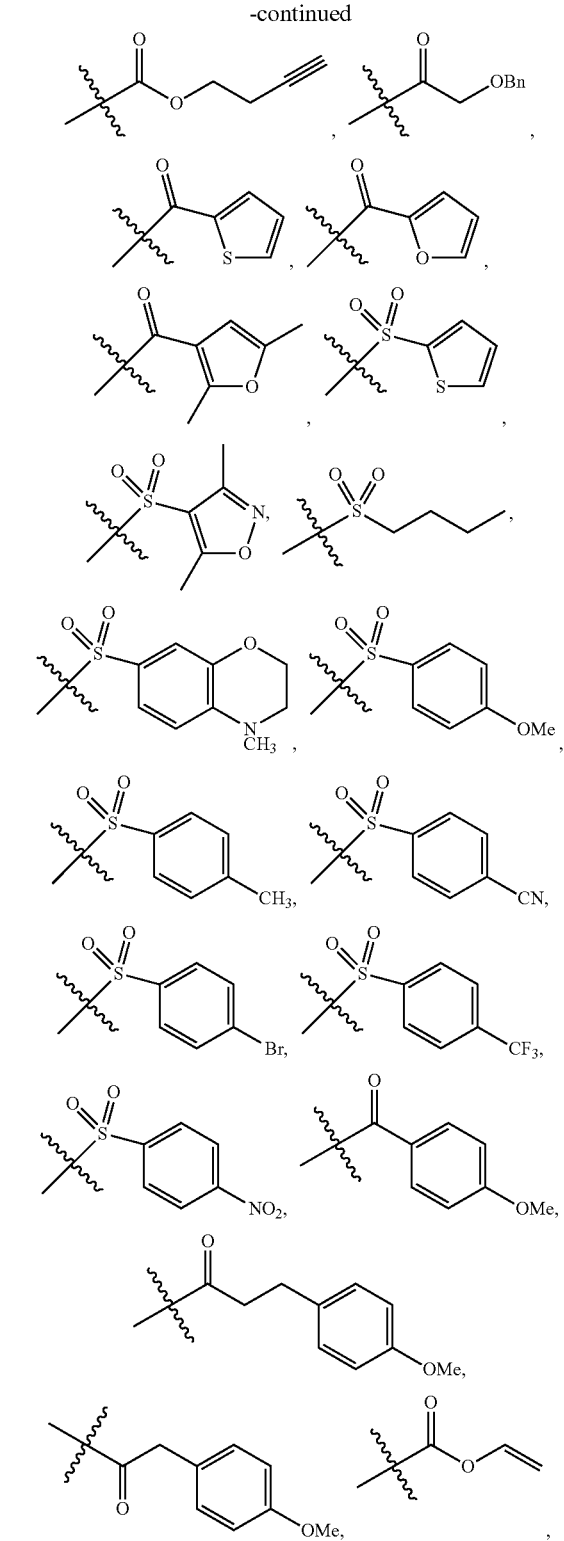
and any combinations thereof.
Preferably, $R^{35}$ is H.
$R^{36}$ can be selected from the group consisting of $OR^{37}$, $N(R^{37})_2$, F, Br, I, Cl, CN, $NO_2$, $CF_3$, $-C\equiv CCH_2CH_2CH_2CH_2CH_2CH_3$, $-C\equiv CCH_2CH_2CH_3$, $-C\equiv CCH_2CH_2OH$,

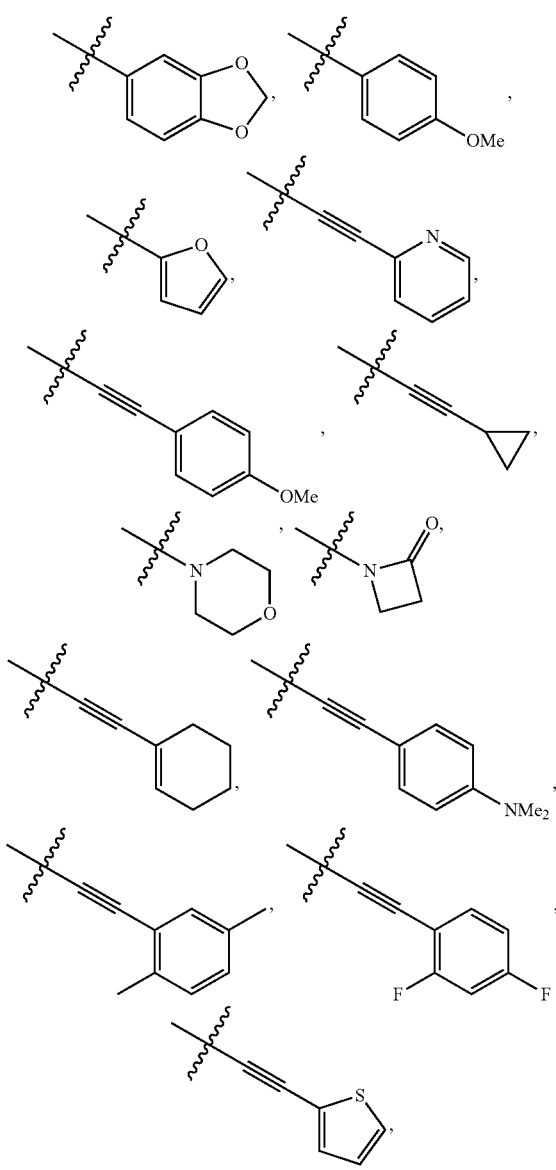

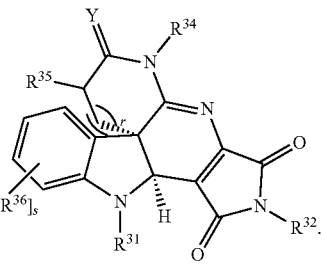

and any combinations thereof. When $R^{36}$ comprises a $R^{37}$ substituent, $R^{37}$ can be a $C_1$-$C_6$ alkyl. Preferably $R^{37}$ is methyl, ethyl, propyl, butyl, pentyl, or t-butyl.

While all isomers of the compounds of formula (III) are claimed, the following two isomers are specifically illustrated. Accordingly, in some embodiments, the compound of formula (III) is of formula (IIIa) or (IIIb):

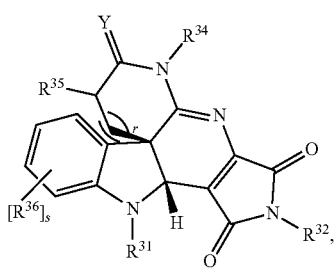

Formula (IIIa)

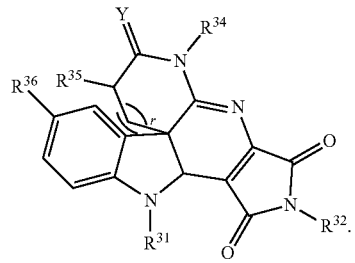

Formula (IIIb)

Preferably, s is 0 or 1. When s is 1, a preferred compound of formula (III) has the structure of formula (IIIc):

Formula (IIIc)

Compounds of Formula (IV)

In some embodiments, u is 1.

In some embodiments, $R^{41}$ is H, alkyl, alkenyl, or alkynyl. In some further embodiments of this $R^{41}$ is selected from the group consisting of H, methyl, ethyl, propyl, butyl, pentyl, hexyl, allyl, but-2-ynyl, 3-methyl-but-2ynyl, benzyl, phenyl, and terminal alkyne, e.g., hept-6-ynyl.

In some embodiments, $R^{41}$ is

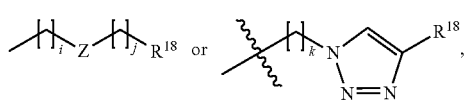

wherein i, j and k are independently an integer from 1 to 10 (e.g., 1, 2, 3, 4, 5, 6, 7, 8, 9, or 10); Z is O, S, NH or $CH_2$; and $R^{18}$ is optionally substituted alkyl, optionally substituted alkenyl, optionally substituted aryl, optionally substituted heteroaryl, optionally substituted cyclyl, or optionally substituted heterocyclyl. In some further embodiments of this k is 5. In some other embodiments, of this $R^{18}$ is

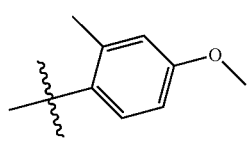 [SMILES: *c1ccc(OC)cc1C]

or —$CH_2NHC(O)CH_3$.

Similarly to compounds of formula (III), $R^{42}$ can be selected from the group consisting of alkyl, aryl, heteroaryl and any combinations thereof. In some embodiments, $R^{42}$ is $R^{42}$ is $SCH_3$, methyl, CN, $CH(CO_2Me)_2$,

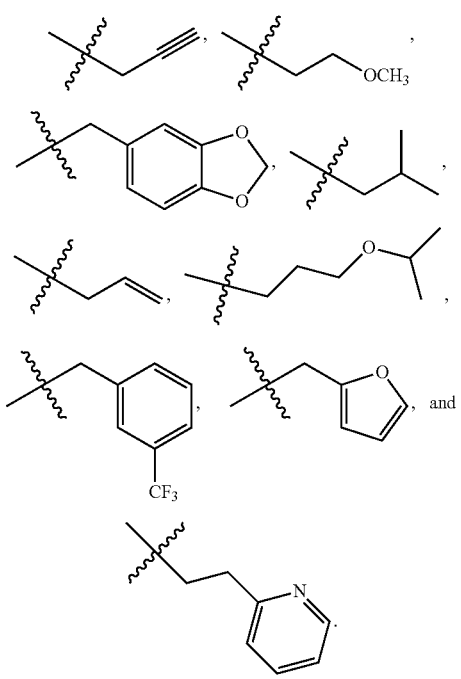
In some embodiments, $R^{44}$ is selected from the group consisting of
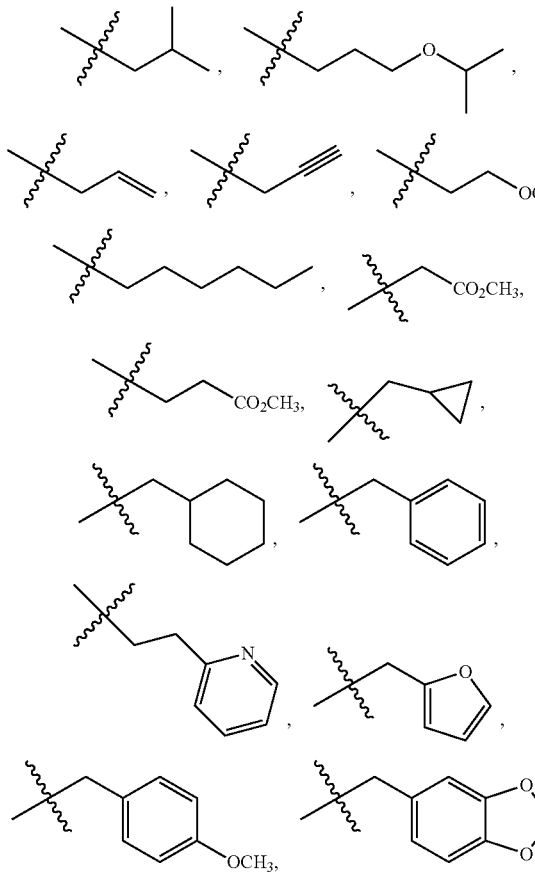
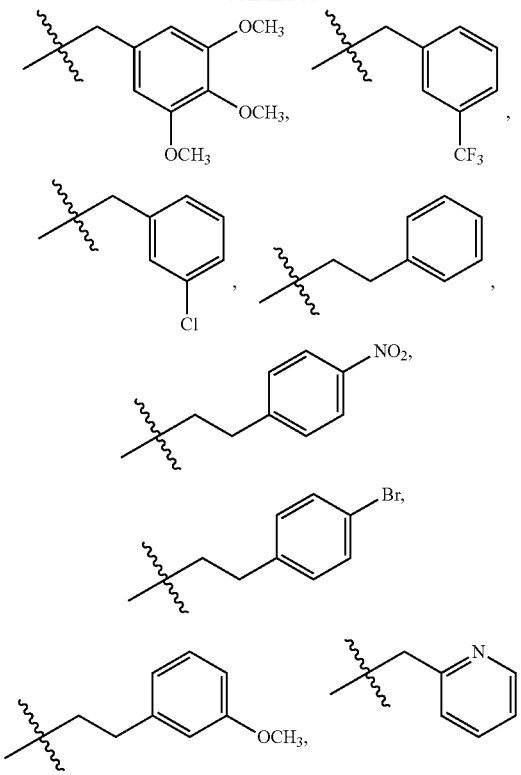
-continued
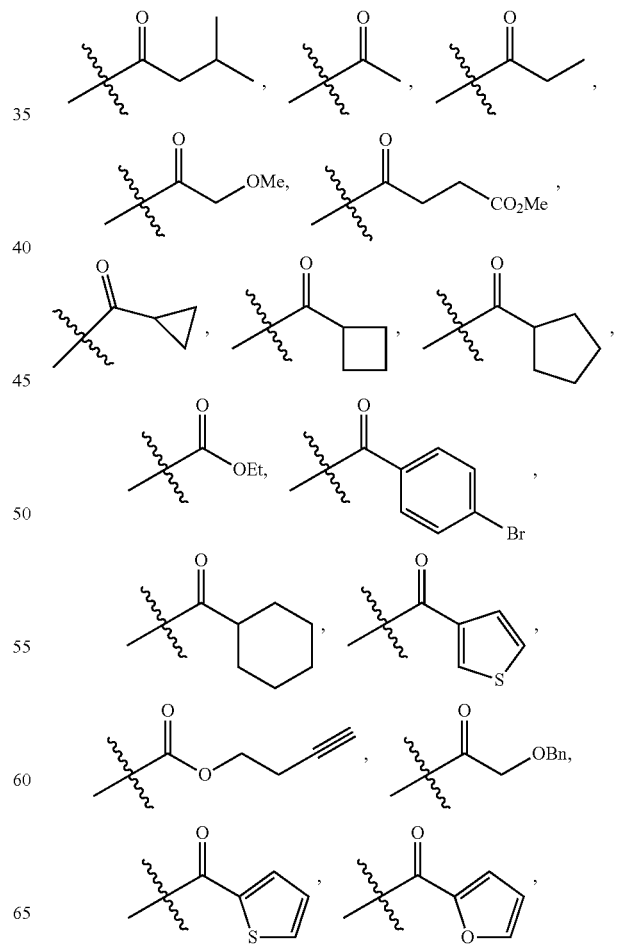

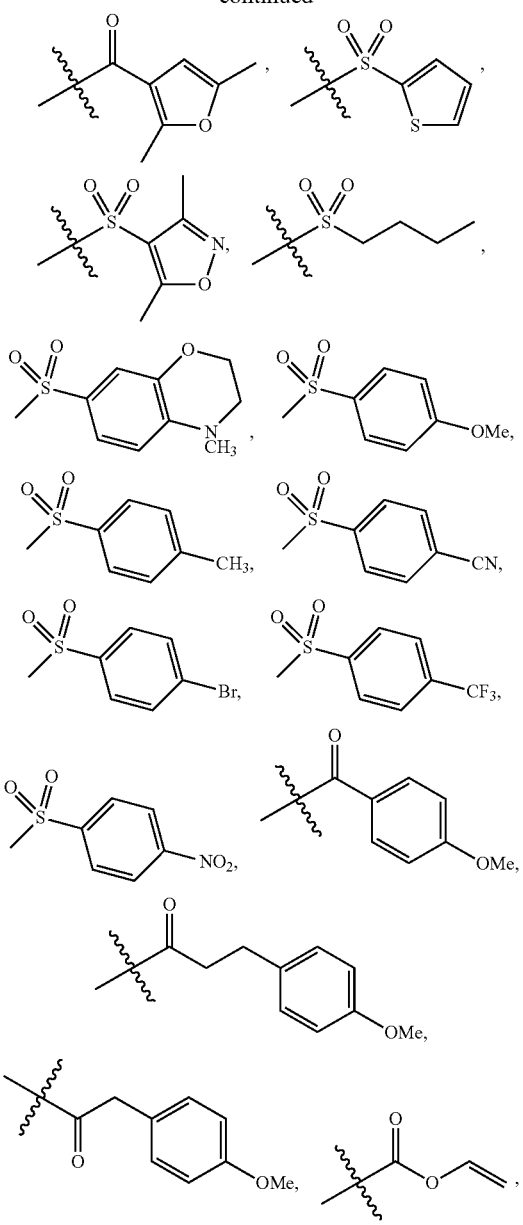

and any combinations thereof.

Preferably, $R^{45}$ is $CO_2R^{47}$ or —$CH_2OR^{47}$, wherein $R^{47}$ is alkyl, aryl or heteroaryl, each of which can be optionally substituted. In some further embodiments of this, $R^{47}$ is methyl.

Without limitations, $R^{46}$ can be selected from the group consisting of $OR^{47}$, $N(R^{47})_2$, F, Br, I, Cl, CN, $NO_2$, $CF_3$, —C≡$CCH_2CH_2CH_2CH_2CH_2CH_3$, —C≡$CCH_2CH_2CH_3$, —C≡$CCH_2CH_2OH$,

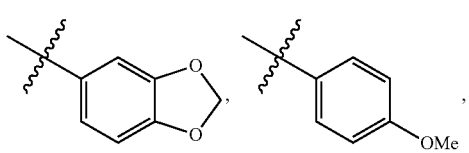

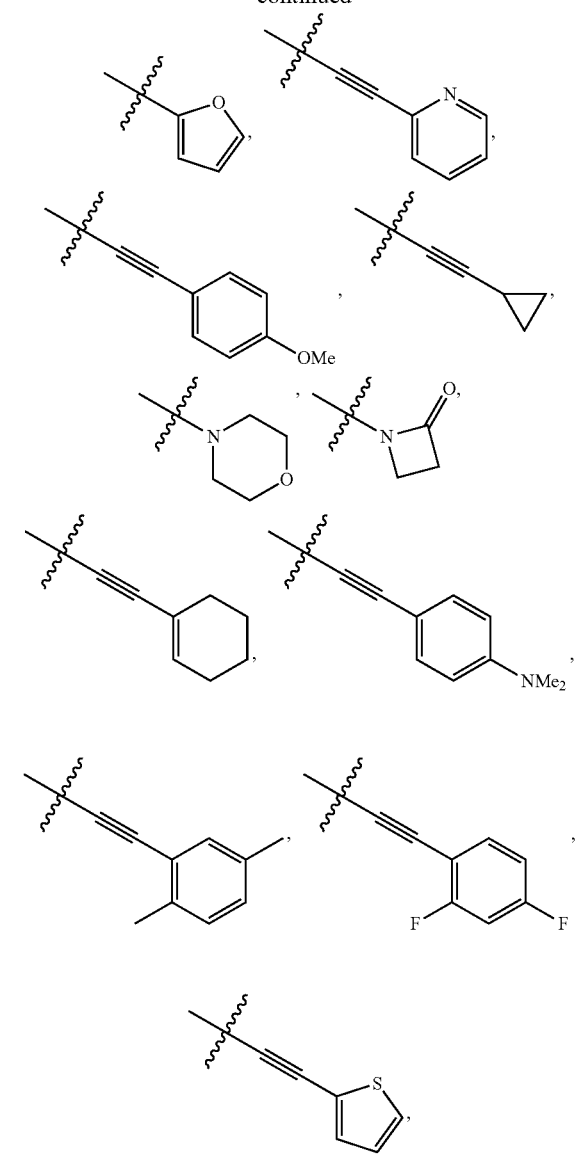

and any combinations thereof. When $R^{46}$ comprises a $R^{47}$ substituent, $R^{47}$ can be a $C_1$-$C_6$ alkyl. Preferably $R^{47}$ is methyl, ethyl, propyl, butyl, pentyl, or t-butyl.

While all isomers of the compounds of formula (IV) are claimed, the following two isomers are specifically illustrated. Accordingly, in some embodiments, the compound of formula (IV) is of formula (IVa) or (IVb):

Formula (IVa)

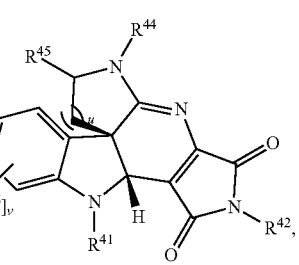

Formula (IVa)
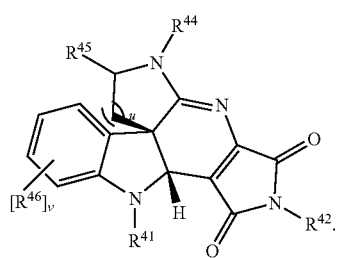
Preferably, v is 0 or 1. When v is 1, a preferred compound of formula (IV) has the structure of formula (IVc):
Formula (IVc)
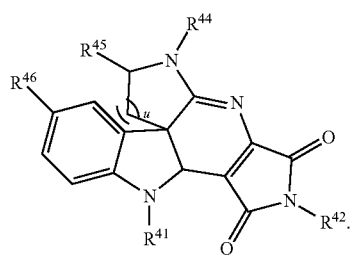
In some embodiments, a compound of formula (IV) has a structure as shown in formula (IVd):
Formula (IVd)
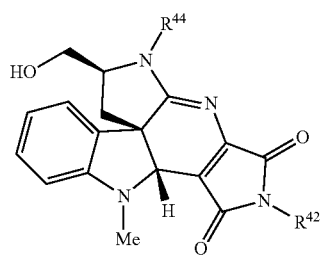
wherein:
$R^{42}$ is
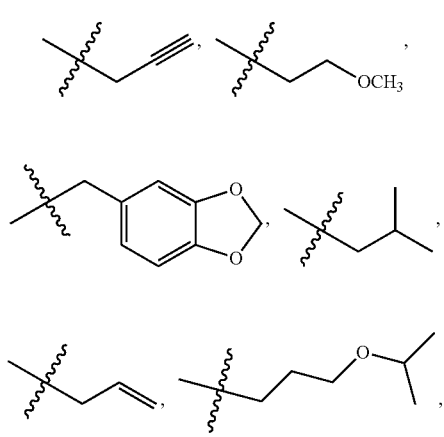
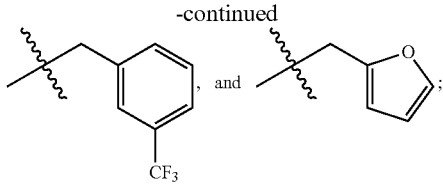
and
$R^{44}$ is
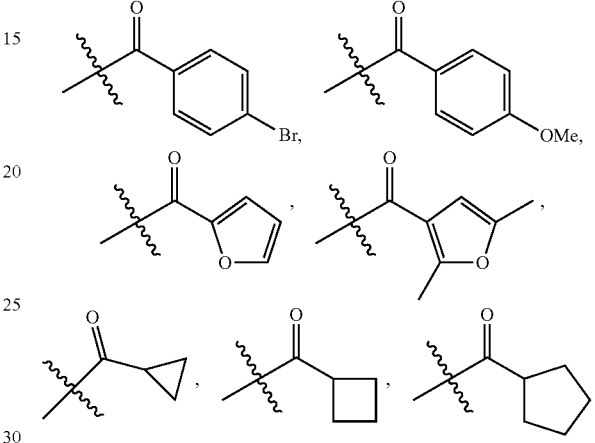
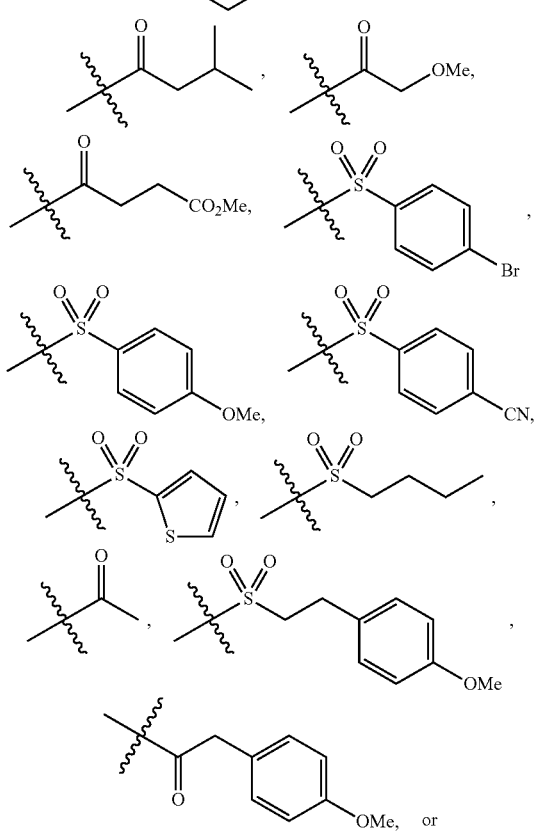

-continued

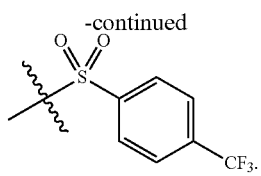

Methods of Inhibiting Core Dimerization

One aspect of the present invention relates to a method of inhibiting hepatitis C virus core dimerization, the method comprising contacting a cell with a compound of formula (I)-(IV), analog, derivative, isomer or prodrug thereof.

The phrases "HCV core dimerization inhibitor" and "HCV inhibitor" are used interchangeably herein and refer to a compound or composition that inhibits Core oligomerization, e.g. Core dimerization.

The term "contacting" or "contact" as used herein in connection with contacting a cell includes subjecting the cell to an appropriate culture media which comprises the indicated HCV inhibitor. Where the cell is in vivo, "contacting" or "contact" includes administering the HCV inhibitor in a pharmaceutical composition to a subject via an appropriate administration route such that the HCV inhibitor contacts the cell in vivo.

For in vivo methods, a therapeutically effective amount of a HCV inhibitor modulator can be administered to a subject. Methods of administering compounds to a subject are well known in the art and available to the skilled artisan.

It is to be understood that the cell is a HCV infected cell and/or a cell that harbors HCV. In some embodiments, the cell is a liver cell. In some embodiments, the cell is a hepatocyte, a Kupffer cell, or a macrophage.

In some embodiments, the cell is a Huh7-5 hepatoma cell.

Dimerization or oligomerization of Core, HCV's most conserved (capsid) protein, plays an essential role in forming the viral particle (McLauchlan, J. (2000) J. Virol. Hepat. 7: 2-14). Interference with HCV core dimerization leads to inhibition of HCV replication and/or inhibit production of infectious viral particles. Thus, Core dimerization, can be monitored by assaying for HCV particles and/or HCV RNA in the cell culture and/or blood of a subject. Methods of assaying for HCV are well known in the art. A number of commercial HCV assays are also available and include, but are not limited to, VITROS® Anti-HCV assay (Ortho Clinical Diagnostics), PROCLEIX® HIV-1/HCV Assay (Novartis Diagnostics), Elecsys Anti-HCV Assay (Roche), Cobas Amplicor HCV Assay, and Abbott RealTime HCV Assay.

In some embodiments, a compound of formula (I)-(IV) has an $IC_{50}$ of less than 100 µM, less than 50 µM, less than 25 µM, less than 20 µM, less than 15 µM, less than 10 µM, less than 5 µM, less than 2.5 µM, less than less than 100 nm, or less than 50 nm. $IC_{50}$ can be determined by the methods as described in the Examples herein, by the Core106 ALPHA screen assay as described in Kota, et al. J. Gen. Virol. (2009) 90: 1319-1328, or by the TR-FRET method described in Kota, et al., ASSAY and Drug Development Technologies (2010(8(1): 96-105, content of both of which is herein incorporated by reference.

In some embodiments, a compound of formula (I)-(IV) has a cytotoxic concentration ($CC_{50}$) against a cell of higher than higher than 1 µM, higher than 50 µM, higher than 100 µM, higher than 200 µM, higher than 300 µM, higher than 400 µM, higher than 500 µM, higher than 600 µM, higher than 700 µM, higher than 800 µM, higher than 900 µM, or higher than 1 mM. As used herein, the term "$CC_{50}$" refers to a standard of measure indicating the concentration of a compound that causes 50 percent of maximum cytotoxicity.

In some embodiments, a compound of formula (I)-(IV) has an $EC_{50}$ of less than 100 µM, less than 50 µM, less than 25 µM, less than 20 µM, less than 15 µM, less than 10 µM, less than 5 µM, less than 2.5 µM, less than less than 100 nm, or less than 50 nm. As used herein, the term "$EC_{50}$," refers to that concentration of a compound at which a given activity is 50% of the maximum for the same activity measurable using the same assay in the absence of the compound. Without limitations, the $EC_{50}$ value can be calculated at an early stage and/or a late stage.

Methods of Treatment

Because interference with Core dimerization inhibits HCV viral particle formation, inhibiting Core dimerization in a subject can lead to treatment, prevention or amelioration of a number of conditions and/or disorders associated with HCV infection. Accordingly, in one aspect, the invention provides a method of treating a viral infection or preventing a disease or disorder caused by a viral infection in a subject in need thereof, the method comprising administering to the subject a therapeutically effective amount of a compound described herein, e.g., a compound of formula (I)-(IV), analogs, derivatives, isomers, prodrugs and pharmaceutically acceptable salts thereof.

As used herein, the term "viral infection" generally encompasses infection of an animal host, particularly a human host, by one or more viruses. Thus, treating viral infection will encompass the treatment of a person who is a carrier of one or more specific viruses or a person who is diagnosed of active symptoms caused by and/or associated with infection by the viruses. A carrier of virus may be identified by any methods known in the art. For example, a subject can be identified as virus carrier on the basis that the subject is antiviral antibody positive, or is virus-positive, or has symptoms of viral infection. That is, "treating viral infection" should be understood as treating a subject who is at any one of the several stages of viral infection progression. In addition, "treating or preventing viral infection" will also encompass treating suspected infection by a particular virus after suspected past exposure to virus by e.g., blood transfusion, exchange of body fluids, bites, accidental needle stick, or exposure to patient blood during surgery, or other contacts with a person with viral infection that may result in transmission of the virus.

Exemplary viral infections include, but are not limited to, infection with hepatitis A virus, hepatitis B virus, hepatitis C virus, HIV, HTLV-1, HTLV-II, influenza A, influenza B, respiratory syncytial virus (RSV), herpes simplex virus types 1 and 2 (HSV), varicella zoster virus (VZV), cytomegalovirus (CMV), Epstein-Barr virus (EBV), human herpes virus type 6 (HHV6), human herpes virus type 7 (HHV-7), human herpes virus type 8 (HHV-8), human papilloma virus infection, rotavirus, adenovirus, and SARS virus.

In some embodiments, viral infection is with a negative RNA strand virus. As used herein, the term "negative strand RNA virus" is defined as a classification of RNA viruses in which the genome comprises the negative strand of an RNA molecule. Exemplary negative RNA strand viruses include, but are not limited to, Ebola virus, Marburg virus, Measeles virus, Mumps virus, Nipah virus, Hendra virus, Rabies virus, Lassa virus, Rift Valley fever virus, La Crosse virus, Hanta virus, Crimean-Congo hemorrhagic fever, influenza viruses, and those viruses in the genera of Deltavirus, Nyavirus (e.g., Nyamanini virus and Midway virus), Ophiovirus, Tenuivirs, and Varicosavirus. Examples of human diseases caused by negative-strand viruses include mumps, measles, pneumonia, bronchitis, influenza, infectious croup, rabies, ebola hemorrhagic fever, marburg hemorrhagic fever, and LaCrosse encephalitis Hepatitis C virus (HCV) infection refers to a clinical disorder caused by infectious agents, e.g., viral agents, which are antigenically and genetically different from hepatitis A virus and hepatitis B virus. Symptoms of HCV infection include at least one or more of the following: fever, nausea, vomiting, jaundice, fatigue, abdominal pain, and dark urine. Infection may be associated with inflammation of the liver and/or necrosis of liver cells. In acute stages, HCV infection is generally milder than hepatitis B virus, but a greater proportion of HCV infections become chronic. As used herein, the term "acute HCV" refers to the initial onset of HCV. Symptoms of acute HCV include at least one or more of the following: malaise, jaundice, a rise in alanine aminotransferase (ALT) levels, the presence of HCV RNA, and the presence of anti-HCV antibodies. As symptoms of HCV persist in a subject, HCV can progress from acute HCV to a chronic state. "Chronic HCV", as used herein, refers to the persistence of HCV infection in a subject. Patients can be classified as having chronic HCV based on the persistence of elevated serum ALT levels and/or the presence of serum HCV RNA and/or the presence of antiHCV antibodies in a patient over a period of at least about 4 months, preferably at least about 6 months, more preferably 7, 8, 9, 10, 11, or 12 months.

Methods of detecting HCV infection and monitoring symptoms of HCV in a subject are known in the art. For example, radioimmunoassays can be used to determine the presence of anti-HCV antibodies in the sera of a subject. See, e.g., Kuo et al. (1989) *Science* 244:362-364. Alternatively, anti-hepatitis C virus antibody to HCV antigen can be detected by fluorescent antibody blocking (Alter et al. 1992. New England Journal of Medicine 327:1899). In addition, several methods are known in the art for detecting HCV RNA in a biological sample. For example, nucleic acid probes (e.g., labeled nucleic acid probes) capable of hybridizing to HCV mRNA can be used to detect the presence of HCV mRNA, preferably serum HCV mRNA. Nucleotide sequences which encode the HCV genome are known in the art. See, for example, EP 0318216, EP 0388232, EP 398748; Kato et al. (1990) *Proc. Natl. Acad. Sci. USA* 87:9524-9528; Choo et al. (1990) *Proc. Natl Acad. Sci. USA* 88:2451-2455; and Choo et al. (1989) *Science* 244:359-362. Thus, using, for example, the nucleotide sequence of cDNA encoding HCV genome as described in Choo et al. (1989) *Science* 244:359362, probes can be derived for detecting the presence of HCV mRNA. HCV RNA can also be detected and quantified, for example, by homogenous reverse transcription polymerase chain reaction (RT-PCR) as described in U.S. Pat. No. 5,527,669, or by nested PCR using a primer set within the 5' non-coding region of HCV as described, for example, in Kobayashi et al. (1998) *I. Gastroenterol.* 33:500-507; Tsai et al. (1997) *Hepatology* 449-458; Di Bischegie et al. (1992) *Hepatology* 16(3):649-655; and, Garson et al. (1990) *Lancet* 335:1419-1422. Such methods can be used to identify subjects infected with HCV as well as to monitor the course of HCV infection in a subject to determine whether the subject has an acute or chronic HCV infection.

As used herein, a "subject" means a human or animal, which can be infected by a virus or have virus-mediated disease or condition. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of conditions or disorders associated with viral infection. In addition, the methods and compositions described herein can be used to treat domesticated animals and/or pets.

A subject can be one who has been previously diagnosed with or identified as suffering from or having a viral infection or a disease or disorder a disease or disorder caused by a viral infection.

A subject can one who is currently being treated for a viral infection or a disease or disorder a disease or disorder caused by a viral infection.

In some embodiments of the aspects described herein, the method further comprising diagnosing a subject for a viral infection or a disease or disorder caused by a viral infection before onset of treatment with a method described herein. Methods of diagnosing viral infections are well known in the art. For example, a subject can be diagnosed with a viral infection based on the presence of anti-virus antibodies, viral RNA, viral-DNA, viral proteins, or viral particles in a subject's serum or blood. Methods for detecting anti-virus antibodies, viral RNA, viral-DNA, viral proteins, or viral particles are well known to the skilled artisan. In many cases kits for diagnosing viral infections are also commercially. A number of commercial HCV assay kits are listed above.

In some embodiments, the method further comprising selecting a subject diagnosed with a viral infection or a disease or disorder caused by a viral infection before For administration to a subject, the compounds of the invention can be provided in pharmaceutically acceptable compositions. Accordingly, in one aspect, the invention provides a pharmaceutical composition comprising a compound of formula (I)-(IV) and a pharmaceutically acceptable carrier.

These pharmaceutically acceptable compositions comprise a compound of the invention, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9)

nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising an aggregate which is effective for producing some desired therapeutic effect in at least a sub-population of cells in an animal at a reasonable benefit/risk ratio applicable to any medical treatment. For example, an amount of a compound described herein administered to a subject that is sufficient to produce a statistically significant, measurable inhibition of HCV core dimerization.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

An aggregate or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments of the aspects described herein, the compositions are administered by intravenous infusion or injection.

The amount of a compound described herein that can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that a compound described herein is given at a dose from 1 µg/kg to 150 mg/kg, 1 µg/kg to 100 mg/kg, 1 µg/kg to 50 mg/kg, 1

μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that HCV inhibitor or a metabolite thereof has an in vivo, e.g., serum or blood, concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the HCV inhibitors. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such subdoses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The compounds described herein can be administrated to a subject in combination with one or more pharmaceutically active agents. Exemplary pharmaceutically active compound include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

In some embodiments of the aspects described herein, pharmaceutically active agent is an antiviral agent. As used herein, the term "antiviral agent" means an agent that is effective to inhibit the formation and/or replication of a virus in a mammal. This includes agents that interfere with either host or viral mechanisms necessary for the formation and/or replication of a virus in a mammal. Such agents can be selected from immunomodulatory agents, inhibitors of a virus polymerase or inhibitors of another target in the virus life cycle. Examples of anti-viral agents include a-methyl-1-adamantanemethylamine, hydroxy-ethoxymethylguanine, adamantanamine, 5-iodo-2'-deoxyuridine, trifluorothymidine, interferon, and adenine arabinoside. Exemplary antiviral agents known in the art for treatment of HCV infection include interferon alpha, ribavirin (1-(3-D-ribofuranosyl-1H-1,2,4-triazoleScarboxamide), non-immunosuppressive cyclosporins, and analogs and derivatives thereof. Exemplary non-immunosuppressive cyclosporins amenable to the present invention include those described in U.S. Pat. App. Pub. No. 2009/0104149, content of which is herein incorporated by reference in its entirety. Additional treatments for HCV infection include those described in U.S. Pat. No. 5,633,388, content of which is herein incorporated by reference in its entirety.

In some embodiments, pharmaceutically active agent include those agents known in the art for treatment of inflammation or inflammation associated disorders.

In some embodiments, the pharmaceutically active agent is an anti-inflammatory agent. Exemplary anti-inflammatory agents include, but are not limited to, non-steroidal anti-inflammatory drugs (NSAIDs—such as aspirin, ibuprofen, or naproxen, coricosteroids (such as presnisone), anti-malarial medication (such as hydrochloroquine), methotrexrate, sulfasalazine, leflunomide, anti-TNF medications, cyclophosphamise and mycophenolate.

The HCV inhibitor and the pharmaceutically active agent can be administrated to the subject in the same pharmaceutical composition or in different pharmaceutical compositions (at the same time or at different times). When administrated at different times, the HCV inhibitor and the pharmaceutically active agent can be administered within 5 minutes, 10 minutes, 20 minutes, 60 minutes, 2 hours, 3 hours, 4, hours, 8 hours, 12 hours, 24 hours of administration of the other When the HCV inhibitor and the pharmaceutically active agent are administered in different pharmaceutical compositions, routes of administration can be different.

In some embodiments, the pharmaceutically active agent is selected from the group consisting of interferon, ribavirin, levovirin, viramidine, isatoribine, an HCV protease inhibitor, an HCV polymerase inhibitor, an HCV IRES inhibitor, an HCV Helicase, an HCV ATPase inhibitor, an NS5A phosphorylation inhibitor, an HCV NS2 inhibitor, a-methyl-1-adamantanemethylamine, hydroxy-ethoxymethylguanine, adamantanamine, 5-iodo-2'-deoxyuridine, trifluorothymidine, adenine arabinoside, a L-nucleoside, non-immunosuppressive cyclosporins, and any combinations thereof.

The invention may be defined as in any of the following paragraphs:

1. A compound having the structure shown in formula (I):

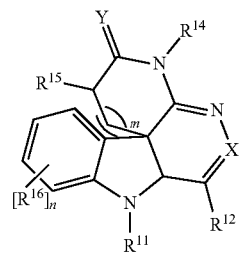

Formula (I)

wherein:

X is CR$^{13}$ or N;

Y is O or S;

R$^{11}$ is H, C(O)R$^{17}$, CO$_2$R$^{17}$, S(O)R$^{17}$, S(O)$_2$R$^{17}$, alkyl, alkenyl, alkynyl, acyl, aryl, heteroaryl, cyclyl, heterocyclyl, each of which can be optionally substituted, or R$^{11}$ is a linker that links two compounds of formula (I) together;

R$^{12}$ and R$^{13}$ are independently for each occurrence H, halogen, N(R$^{17}$)$_2$, NO$_2$, OR$^{17}$, CF$_3$, CN, C(O)R$^{17}$, CO$_2$R$^{17}$, SO$_3$R$^{17}$, SR$^{17}$, S(O)R$^{17}$, S(O)$_2$R$^{17}$, CH(CO$_2$R$^{17}$)$_2$, alkyl, alkenyl, alkynyl, acyl, aryl, heteroaryl, cyclyl or heterocyclyl, each of which can be optionally substituted;

R$^{14}$ is C(O)R$^{17}$, CO$_2$R$^{17}$, C(O)N(R$^{17}$)$_2$, S(O)R$^{17}$, S(O)$_2$R$^{17}$, alkyl, alkenyl, alkynyl, acyl, aryl, heteroaryl, cyclyl, heterocyclyl, each of which can be optionally substituted;

R$^{15}$ is H, halogen, CF$_3$, CN, —(CH$_2$)$_t$OR$^{17}$ (t is 1, 2, 3, 4, 5, 6, 7, 8, 9 or 10), C(O)R$^{17}$, CO$_2$R$^{17}$, OR$^{17}$, SR$^{17}$, S(O)R$^{17}$, S(O)$_2$R$^{17}$, alkyl, alkenyl, alkynyl, aryl, heteroaryl, cyclyl, heterocyclyl, each of which can be optionally substituted;

R$^{16}$ is independently for each occurrence halogen, N(R$^{17}$)$_2$, NO$_2$, OR$^{17}$, CF$_3$, CN, C(O)R$^{17}$, CO$_2$R$^{17}$, SO$_3$R$^{17}$, SR$^{17}$, S(O)R$^{17}$, S(O)$_2$R$^{17}$, CH(CO$_2$R$^{17}$)$_2$, alkyl, alkenyl, alkynyl, acyl, aryl, heteroaryl, cyclyl or heterocyclyl, each of which can be optionally substituted;

R$^{17}$ is independently for each occurrence H, alkyl, alkenyl, alkynyl, acyl, aryl, heteroaryl, cyclyl, or heterocyclyl, each of which can be optionally substituted m is 1, 2, or 3;

n is 0, 1, 2, 3, or 4; and analogs, derivatives, stereoisomers and pharmaceutically acceptable salts thereof.

2. The compound of paragraph 1, wherein m is 1.

3. The compound of any of paragraphs 1-3, wherein R$^{11}$ is selected from the group consisting of H, methyl, ethyl, propyl, butyl, pentyl, hexyl, allyl, but-2-ynyl, 3-methyl-but-2ynyl, benzyl, phenyl, hetp-6-ynyl,

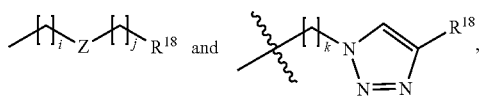

wherein i, j and k are independently an integer from 1 to 10; Z is O, S, NH or CH$_2$; and R$^{18}$ is optionally substituted alkyl, optionally substituted alkenyl, optionally substituted aryl, optionally substituted heteroaryl, optionally substituted cyclyl, or optionally substituted heterocyclyl.

4. The compound of paragraph 3, wherein R$^{18}$ is

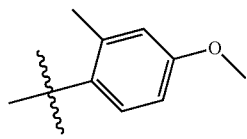 [SMILES: *c1ccc(OC)cc1C]

or —CH$_2$NHC(O)CH$_3$.

5. The compound of any of paragraphs 1-4, wherein at least one of R$^{12}$ and R$^{13}$ is selected from the group consisting of CO$_2$Me, CH$_3$, CF$_3$, SMe, CN, CH(CO$_2$Me$_2$)$_2$, aryl, heteroaryl and any combinations thereof.

6. The compound of any of paragraphs 1-5, wherein R$^{14}$ is selected from the group consisting of

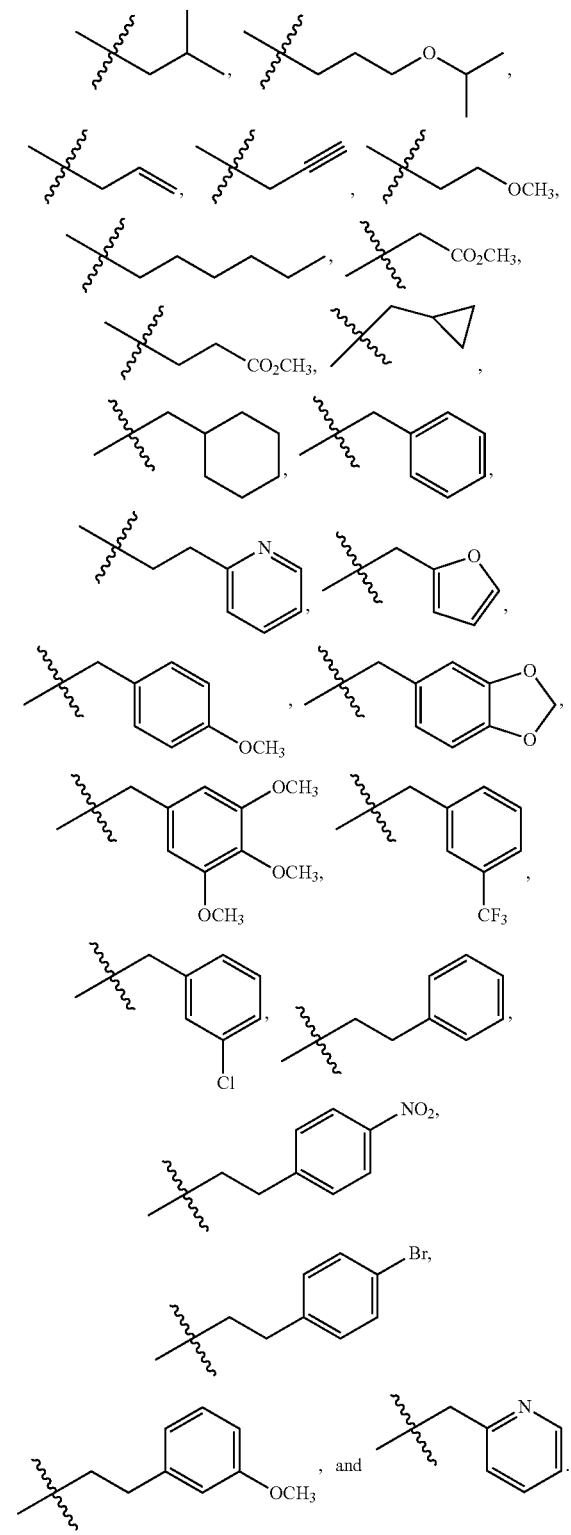

7. The compound of any of paragraphs 1-6, wherein R$^{15}$ is H.

8. The compound of any of paragraphs 1-7, wherein $R^{16}$ is selected from the group consisting of OMe, $NH_2$, F, Br, I, Cl, CN, $CF_3$, $NO_2$, $CF_3$, —C≡CCH$_2$CH$_2$CH$_2$CH$_2$CH$_2$CH$_3$, —C≡CCH$_2$CH$_2$CH$_3$, —C≡CCH$_2$CH$_2$OH,

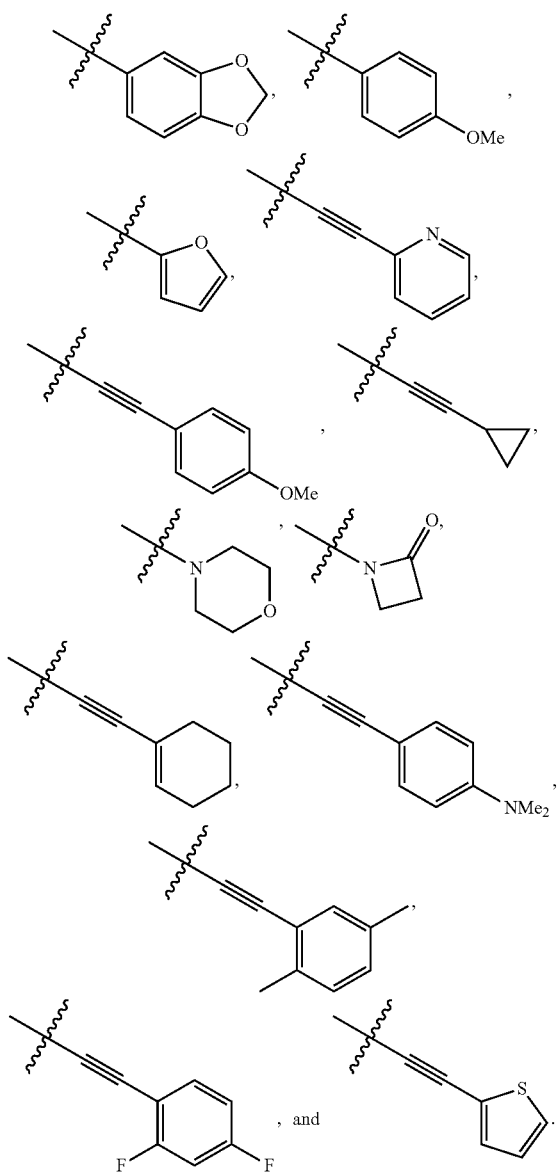

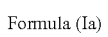, and

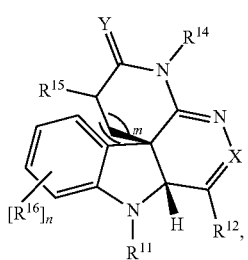

9. The compound of any of paragraphs 1-8, wherein the compound is of formula (Ia) or (Ib):

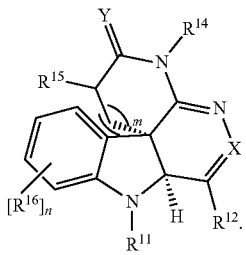

Formula (Ia)

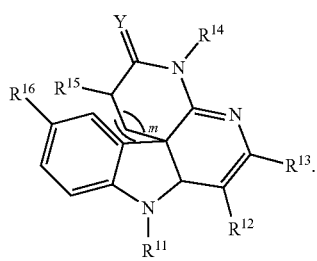

Formula (I)

10. The compound of any of paragraphs 1-9, wherein n is 0.
11. The compound of any of paragraphs 1-9, wherein the compound is of formula (Ic):

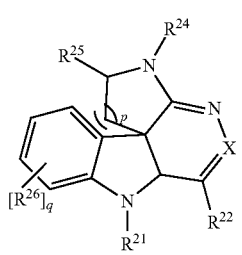

Formula (Ic)

12. A compound having the structure shown in formula (II):

Formula (II)

wherein:
X is $CR^{22}$ or N;
$R^{21}$ is H, $C(O)R^{27}$, $CO_2R^{27}$, $S(O)R^{27}$, $S(O)_2R^{27}$, alkyl, alkenyl, alkynyl, acyl, aryl, heteroaryl, cyclyl, heterocyclyl, each of which can be optionally substituted, or $R^{21}$ is a linker that links two compounds of formula (II) together;
$R^{22}$ and $R^{23}$ are independently for each occurrence H, halogen, $N(R^{27})_2$, $NO_2$, $OR^{27}$, $CF_3$, CN, $C(O)R^{27}$, $CO_2R^{27}$, $SO_3R^{27}$, $SR^{27}$, $S(O)R^{27}$, $S(O)_2R^{27}$, $CH(CO_2R^{27})_2$, alkyl, alkenyl, alkynyl, acyl, aryl, heteroaryl, cyclyl or heterocyclyl, each of which can be optionally substituted;
$R^{24}$ is $C(O)R^{27}$, $CO_2R^{27}$, $C(O)N(R^{27})_2$, $S(O)R^{27}$, $S(O)_2R^{27}$, alkyl, alkenyl, alkynyl, acyl, aryl, heteroaryl, cyclyl, heterocyclyl, each of which can be optionally substituted;
$R^{25}$ is halogen, $CF_3$, CN, —$(CH_2)_tOR^{27}$ (t is 1, 2, 3, 4, 5, 6, 7, 8, 9 or 10), $C(O)R^{27}$, $CO_2R^{27}$, $OR^{27}$, $SR^{27}$, $S(O)R^{27}$, $S(O)_2R^{27}$, alkyl, alkenyl, alkynyl, aryl, heteroaryl, cyclyl, heterocyclyl, each of which can be optionally substituted;
$R^{26}$ is independently for each occurrence halogen, $N(R^{27})_2$, $NO_2$, $OR^{27}$, $CF_3$, CN, $C(O)R^{27}$, $CO_2R^{27}$, $SO_3R^{27}$, $SR^{27}$, $S(O)R^{27}$, $S(O)_2R^{27}$, $CH(CO_2R^{27})_2$, alkyl, alkenyl, alkynyl, acyl, aryl, heteroaryl, cyclyl or heterocyclyl, each of which can be optionally substituted;

$R^{27}$ is independently for each occurrence H, alkyl, alkenyl, alkynyl, acyl, aryl, heteroaryl, cyclyl, or heterocyclyl, each of which can be optionally substituted p is 1, 2, 3, or 4;

q is 0, 1, 2, 3, or 4; and analogs, derivatives, stereoisomers and pharmaceutically acceptable salts thereof.

13. The compound of paragraph 12, wherein p is 1.
14. The compound of any of paragraphs 12-13, wherein $R^{21}$ is selected from the group consisting of H, methyl, ethyl, propyl, butyl, pentyl, hexyl, allyl, but-2-ynyl, 3-methyl-but-2ynyl, benzyl, phenyl, hept-6-ynyl,

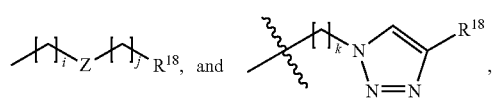

wherein i, j and k are independently an integer from 1 to 10; Z is O, S, NH or $CH_2$; and $R^{18}$ is optionally substituted alkyl, optionally substituted alkenyl, optionally substituted aryl, optionally substituted heteroaryl, optionally substituted cyclyl, or optionally substituted heterocyclyl.

15. The compound of any of paragraphs 12-14, wherein at least one of $R^{22}$ and $R^{23}$ is selected from the group consisting of $CO_2Me$, $CH_3$, $CF_3$, CN, SMe, $CH(CO_2Me_2)_2$, aryl, heteroaryl and any combinations thereof.
16. The compound of any of paragraphs 12-15, wherein $R^{24}$ is selected from the group consisting of

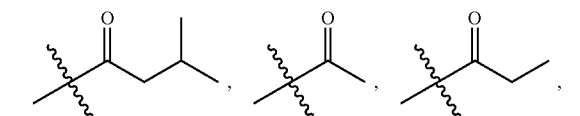

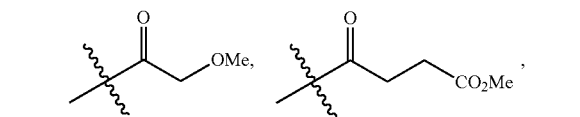

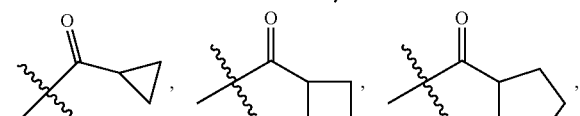

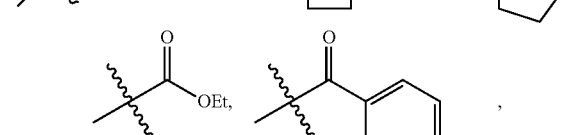

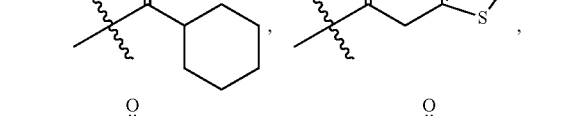

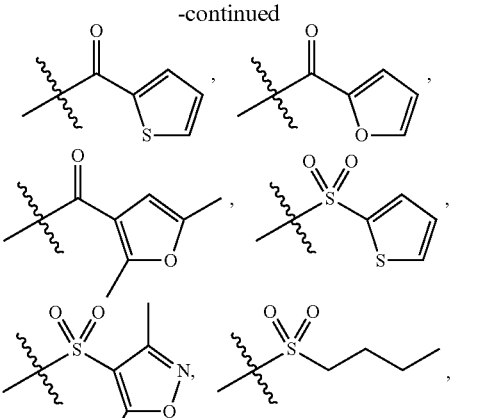

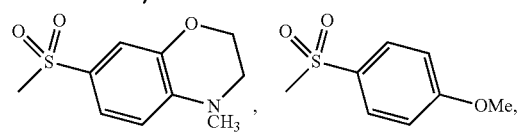

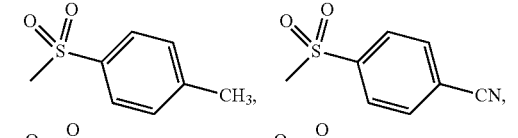

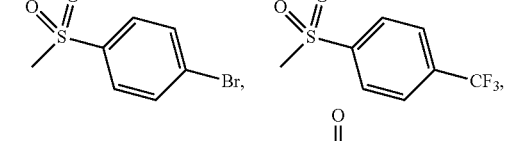

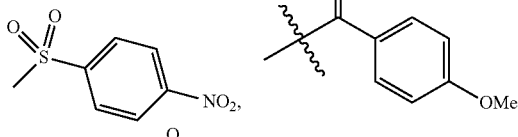

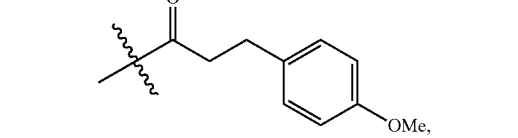

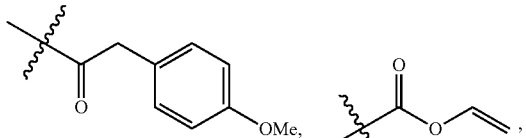

and any combinations thereof.

17. The compound of any of paragraphs 12-16, wherein $R^{25}$ is $-CO_2Me$ or $-CH_2OMe$.
18. The compound of any of paragraphs 12-17, wherein $R^{26}$ is selected from the group consisting of OMe, $NH_2$, F, Br, I, Cl, CN, $NO_2$, $CF_3$, $-C\equiv CCH_2CH_2CH_2CH_2CH_2CH_3$, $-C\equiv CCH_2CH_2CH_3$, $-C\equiv CCH_2CH_2OH$,

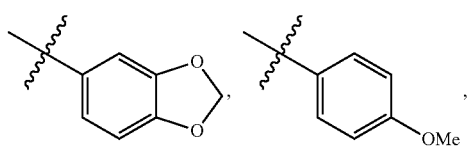

-continued

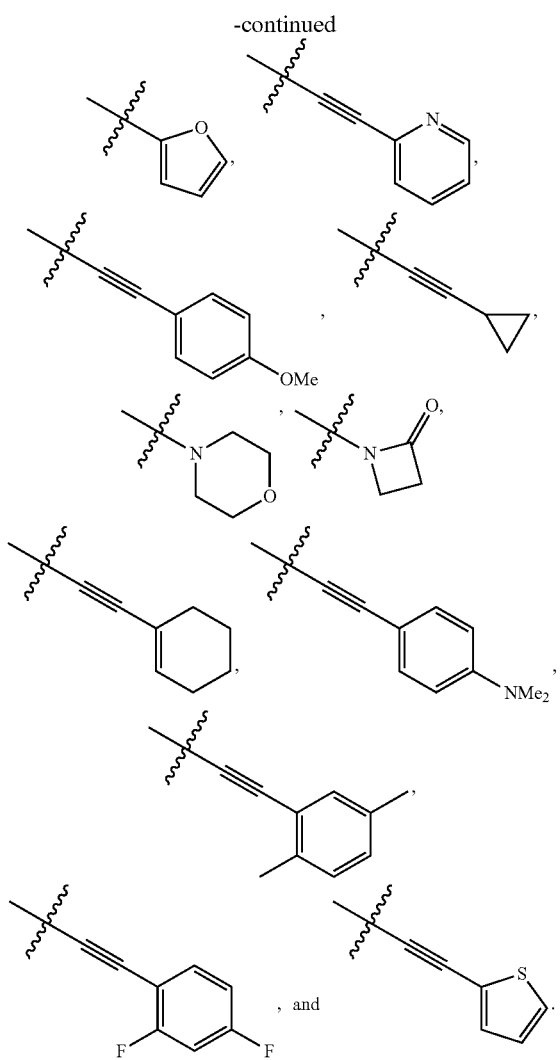

19. The compound of any of paragraphs 12-18, wherein compound is of formula (IIa) or (IIb):

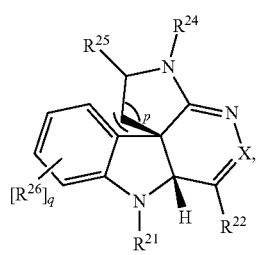

Formula (IIa)

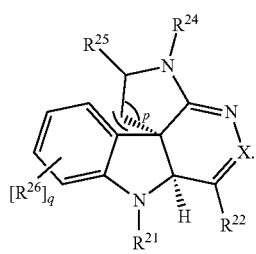

Formula (IIb)

20. The compound of any of paragraphs 12-19, wherein q is 0.
21. The compound of any of paragraphs 12-19, wherein the compound is of formula (IIc):

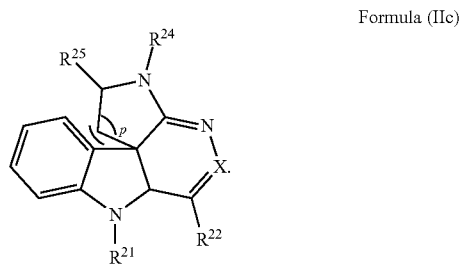

Formula (IIc)

22. A compound having the structure shown in formula (III):

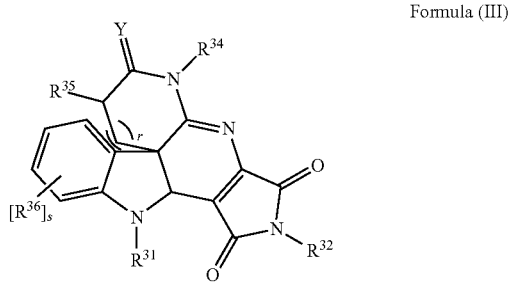

Formula (III)

wherein:
Y is O or S
$R^{31}$ is H, $C(O)R^{37}$, $CO_2R^{37}$, $S(O)R^{37}$, $S(O)_2R^{37}$, alkyl, alkenyl, alkynyl, acyl, aryl, heteroaryl, cyclyl, heterocyclyl, each of which can be optionally substituted, or $R^{31}$ is a linker that links two compounds of formula (III) together;
$R^{32}$ is H, halogen, $N(R^{37})_2$, $NO_2$, $OR^{37}$, $CF_3$, CN, $C(O)R^{37}$, $-(CH_2)_tOR^{37}$ (t is 1, 2, 3, 4, 5 or 6), $CO_2R^{37}$, $SO_3R^{37}$, $SR^{37}$, $S(O)R^{37}$, $S(O)_2R^{37}$, $CH(CO_2R^{37})_2$, alkyl, alkenyl, alkynyl, acyl, aryl, heteroaryl, cyclyl or heterocyclyl, each of which can be optionally substituted;
$R^{34}$ is $C(O)R^{37}$, $CO_2R^{37}$, $C(O)N(R^{37})_2$, $S(O)R^{37}$, $S(O)_2R^{37}$, alkyl, alkenyl, alkynyl, acyl, aryl, heteroaryl, cyclyl, heterocyclyl, each of which can be optionally substituted;
$R^{35}$ is H, halogen, $CF_3$, CN, $-(CH_2)_tOR^{17}$ (t is 1, 2, 3, 4, 5, 6, 7, 8, 9 or 10), $C(O)R^{17}$, $CO_2R^{17}$, $OR^{17}$, $SR^{17}$, $S(O)R^{17}$, $S(O)_2R^{17}$, alkyl, alkenyl, alkynyl, aryl, heteroaryl, cyclyl, heterocyclyl, each of which can be optionally substituted;
$R^{36}$ is independently for each occurrence halogen, $N(R^{37})_2$, $NO_2$, $OR^{37}$, $CF_3$, CN, $C(O)R^{37}$, $CO_2R^{37}$, $SO_3R^{37}$, $SR^{37}$, $S(O)R^{37}$, $S(O)_2R^{37}$, $CH(CO_2R^{37})_2$, alkyl, alkenyl, alkynyl, acyl, aryl, heteroaryl, cyclyl or heterocyclyl, each of which can be optionally substituted;
$R^{37}$ is independently for each occurrence H, alkyl, alkenyl, alkynyl, acyl, aryl, heteroaryl, cyclyl, or heterocyclyl, each of which can be optionally substituted
r is 1, 2, or 3;
s is 0, 1, 2, 3, or 4; and
analogs, derivatives, stereoisomers and pharmaceutically acceptable salts thereof.

23. The compound of paragraph 22, wherein r is 1.

24. The compound of any of paragraphs 22-23, wherein $R^{31}$ is selected from the group consisting of H, methyl, ethyl, propyl, butyl, pentyl, hexyl, allyl, but-2-ynyl, 3-methyl-but-2ynyl, benzyl, phenyl, hept-6-ynyl,

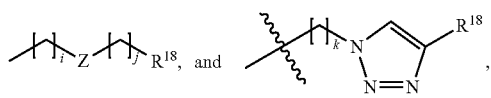

wherein i, j and k are independently an integer from 1 to 10; Z is O, S, NH or $CH_2$; and $R^{18}$ is optionally substituted alkyl, optionally substituted alkenyl, optionally substituted aryl, optionally substituted heteroaryl, optionally substituted cyclyl, or optionally substituted heterocyclyl.

25. The compound of any of paragraphs 22-24, wherein $R^{32}$ is selected from the group consisting of

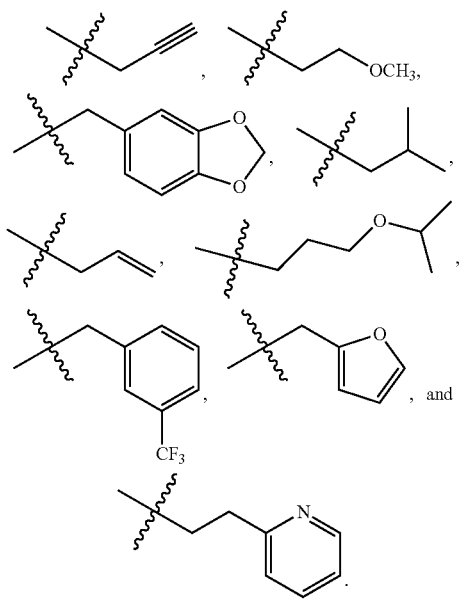

26. The compound of any of paragraphs 22-25, wherein $R^{34}$ is selected from the group consisting of

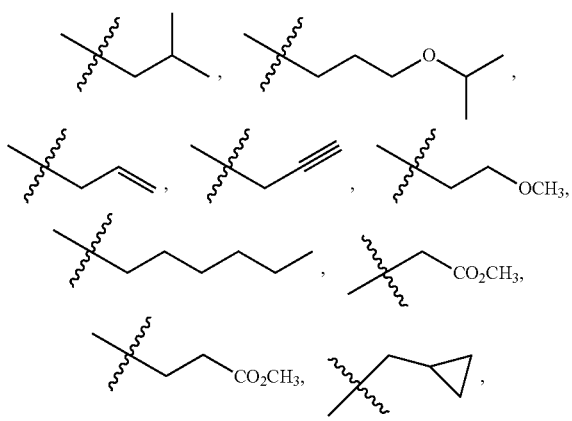

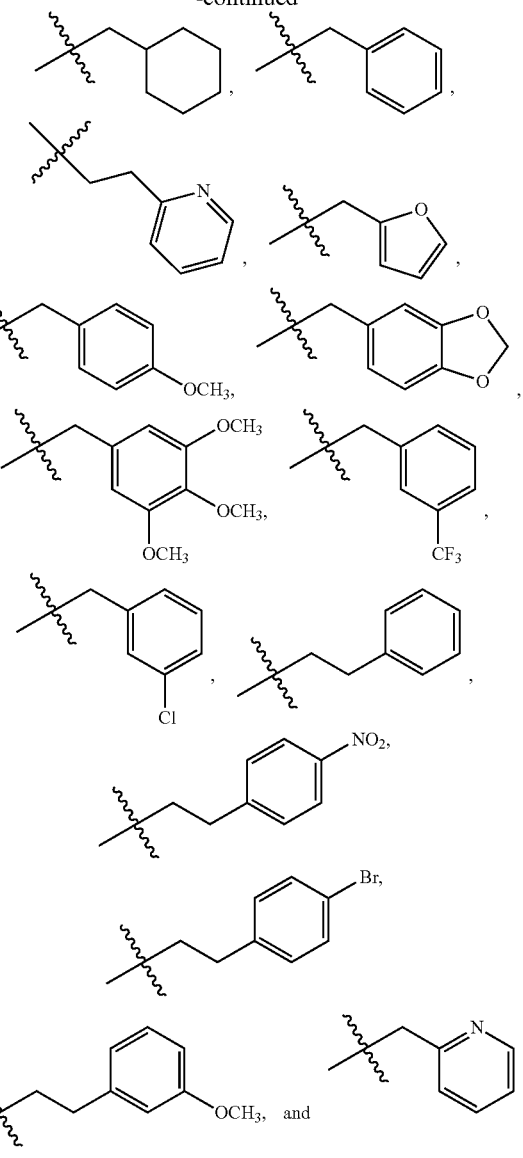

27. The compound of any of paragraphs 22-26, wherein $R^{35}$ is H.

28. The compound of any of paragraphs 22-27, wherein $R^{36}$ is selected from the group consisting of OMe, $NH_2$, F, Br, I, Cl, CN, $NO_2$, $CF_3$, —C≡CCH$_2$CH$_2$CH$_2$CH$_2$CH$_2$CH$_3$, —C≡CCH$_2$CH$_2$CH$_3$, —C≡CCH$_2$CH$_2$OH,

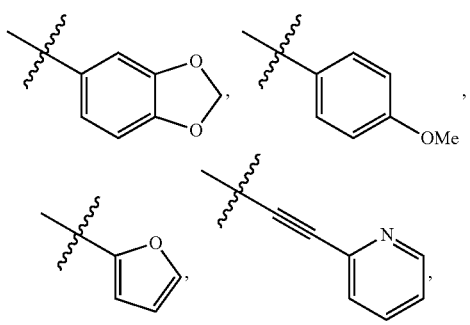

53

-continued

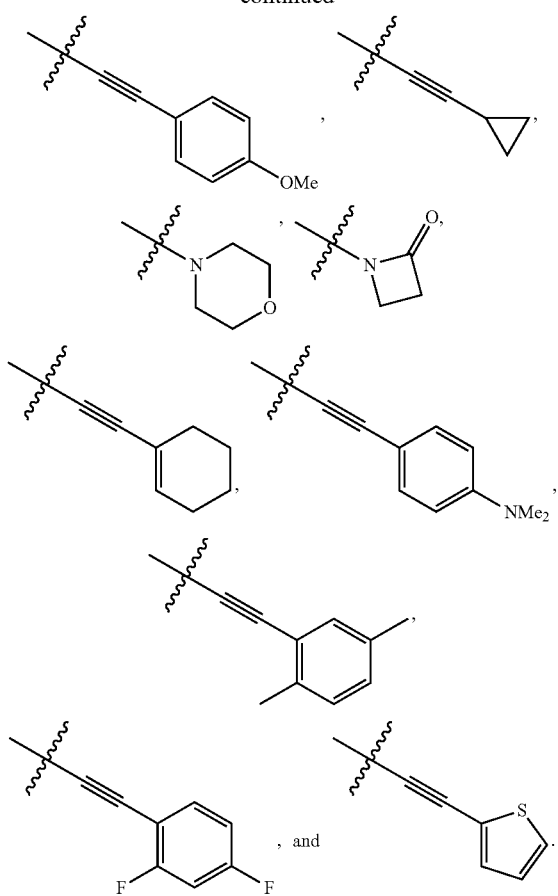

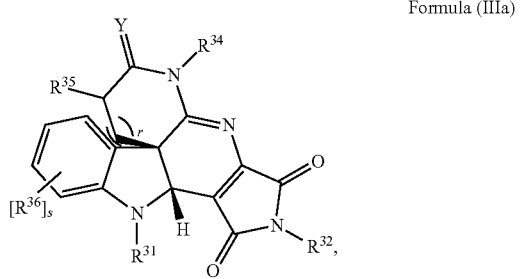

, and

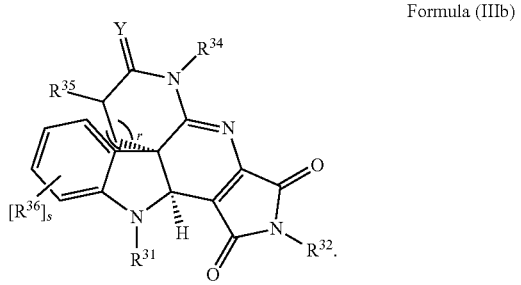

29. The compound of any of paragraphs 22-28, wherein the compound is of formula (IIIa) or (IIIb):

Formula (IIIa)

Formula (IIIb)

30. The compound of any of paragraphs 22-29, wherein s is 0.

54

31. The compound of any of paragraphs 22-29, wherein compound is of formula (IIIc):

Formula (IIIc)

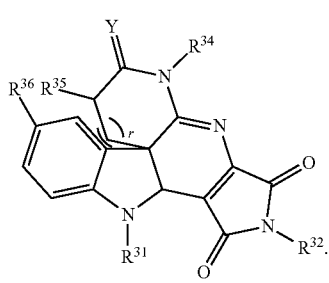

32. A compound having the structure shown in formula (IV):

Formula (IV)

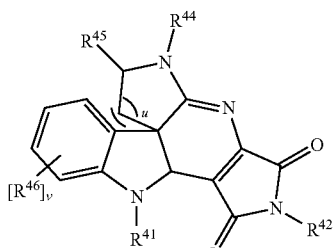

wherein:
$R^{41}$ is H, C(O)$R^{47}$, CO$_2$$R^{47}$, S(O)$R^{47}$, S(O)$_2$$R^{47}$, alkyl, alkenyl, alkynyl, acyl, aryl, heteroaryl, cyclyl, heterocyclyl, each of which can be optionally substituted, or $R^{41}$ is a linker that links two compounds of formula (IV) together;

$R^{42}$ is H, halogen, N($R^{47}$)$_2$, NO$_2$, O$R^{47}$, CF$_3$, CN, C(O)$R^{47}$, —(CH$_2$)$_t$O$R^{47}$ (t is 1, 2, 3, 4, 5 or 6), CO$_2$$R^{47}$, SO$_3$$R^{47}$, S$R^{47}$, S(O)$R^{47}$, S(O)$_2$$R^{47}$, CH(CO$_2$$R^{47}$)$_2$, alkyl, alkenyl, alkynyl, acyl, aryl, heteroaryl, cyclyl or heterocyclyl, each of which can be optionally substituted;

$R^{44}$ is H, C(O)$R^{47}$, CO$_2$$R^{47}$, C(O)N($R^{47}$)$_2$, S(O)$R^{47}$, S(O)$_2$$R^{47}$, alkyl, alkenyl, alkynyl, acyl, aryl, heteroaryl, cyclyl, heterocyclyl, each of which can be optionally substituted;

$R^{45}$ is halogen, CF$_3$, CN, —(CH$_2$)$_t$O$R^{47}$ (t is 1, 2, 3, 4, 5, 6, 7, 8, 9 or 10), C(O)$R^{47}$, CO$_2$$R^{47}$, O$R^{47}$, S$R^{47}$, S(O)$R^{47}$, S(O)$_2$$R^{47}$, alkyl, alkenyl, alkynyl, aryl, heteroaryl, cyclyl, heterocyclyl, each of which can be optionally substituted;

$R^{46}$ is independently for each occurrence halogen, N($R^{47}$)$_2$, NO$_2$, O$R^{47}$, CF$_3$, CN, C(O)$R^{47}$, CO$_2$$R^{47}$, SO$_3$$R^{47}$, S$R^{47}$, S(O)$_R$$^{47}$, S(O)$_2$$R^{47}$, CH(CO$_2$$R^{47}$)$_2$, alkyl, alkenyl, alkynyl, acyl, aryl, heteroaryl, cyclyl or heterocyclyl, each of which can be optionally substituted;

$R^{47}$ is independently for each occurrence H, alkyl, alkenyl, alkynyl, acyl, aryl, heteroaryl, cyclyl, or heterocyclyl, each of which can be optionally substituted u is 1, 2, 3, or 4;
v is 0, 1, 2, 3, or 4; and
analogs, derivatives, isomers and pharmaceutically acceptable salts thereof.

33. The compound of paragraph 32, wherein u is 1.
34. The compound of any of paragraphs 32-33, wherein $R^{41}$ is selected from the group consisting of H, methyl, ethyl, propyl, butyl, pentyl, hexyl, allyl, but-2-ynyl, 3-methyl-but-2ynyl, benzyl, phenyl, hept-6-ynyl,

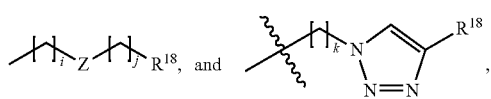

wherein i, j and k are independently an integer from 1 to 10; Z is O, S, NH or $CH_2$; and $R^{18}$ is optionally substituted alkyl, optionally substituted alkenyl, optionally substituted aryl, optionally substituted heteroaryl, optionally substituted cyclyl, or optionally substituted heterocycyl.

35. The compound of any of paragraphs 32-34, wherein $R^{42}$ is selected from the group consisting of $SCH_3$, methyl, CN, $CH(CO_2Me)_2$,

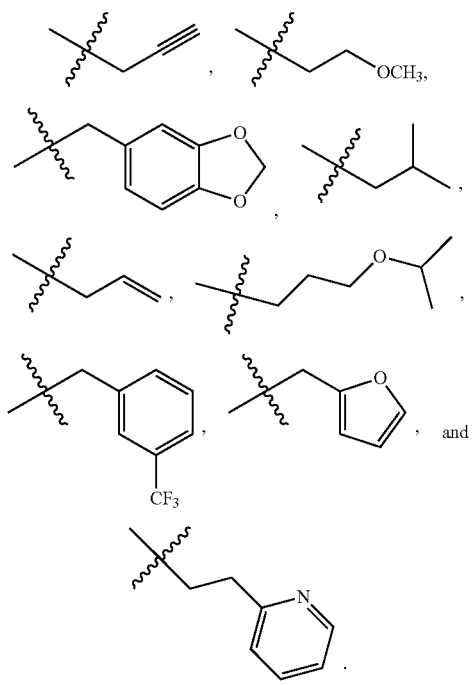

36. The compound of any of paragraphs 32-35, wherein $R^{44}$ is selected from the group consisting of

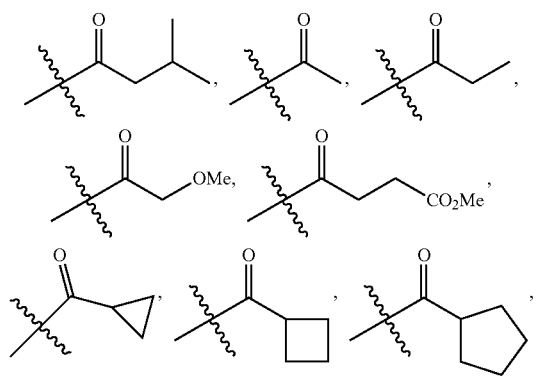

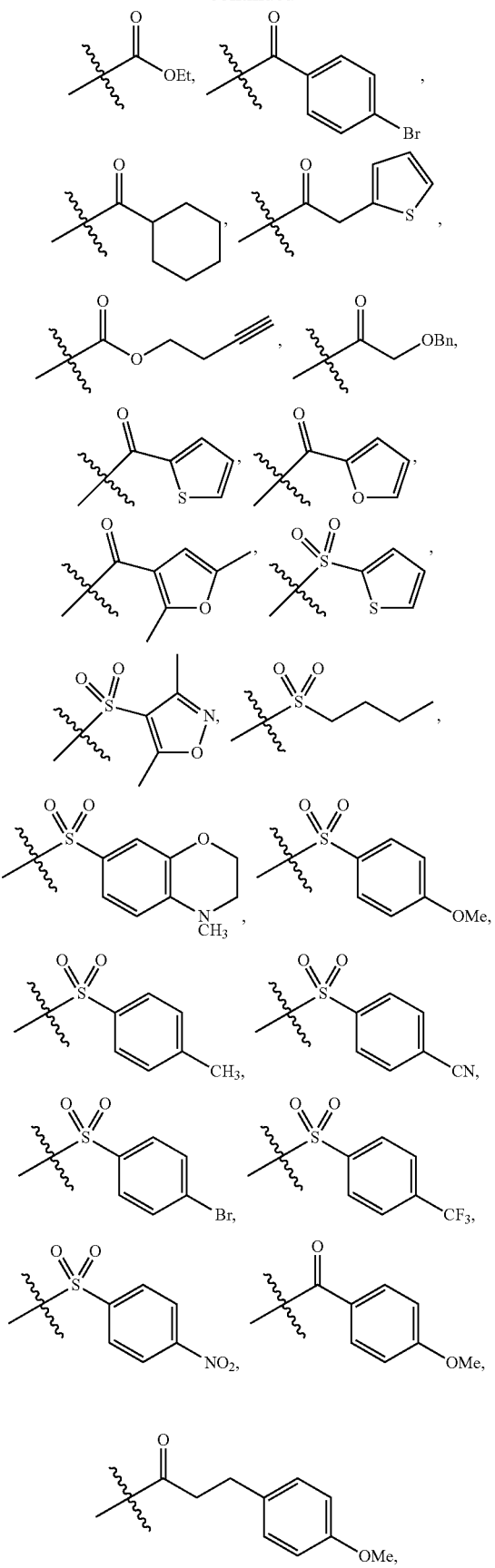

-continued

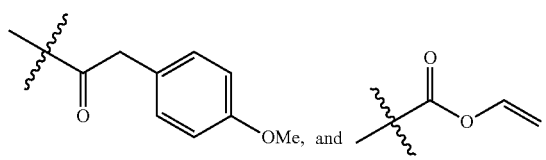

37. The compound of any of paragraphs 32-36, wherein $R^{45}$ is $CO_2Me$ or —$CH_2OMe$.
38. The compound of any of paragraphs 32-37, wherein $R^{46}$ is selected from the group consisting of OMe, $NH_2$, F, Br, I, Cl, CN, $NO_2$, $CF_3$, —C≡CCH$_2$CH$_2$CH$_2$CH$_2$CH$_2$CH$_3$, —C≡CCH$_2$CH$_2$CH$_3$, —C≡CCH$_2$CH$_2$OH,

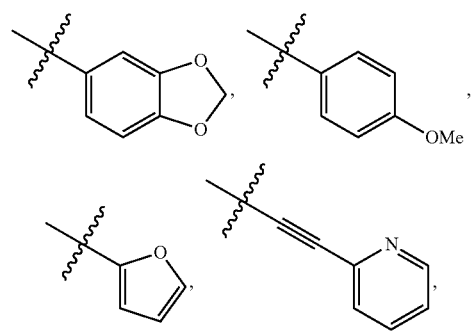

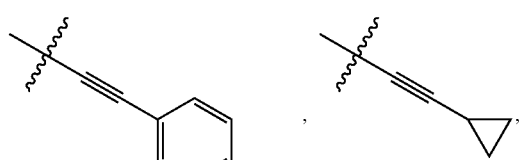

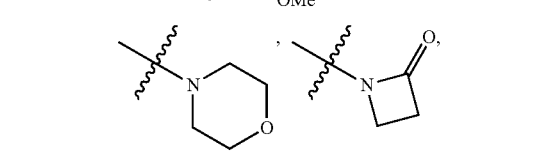

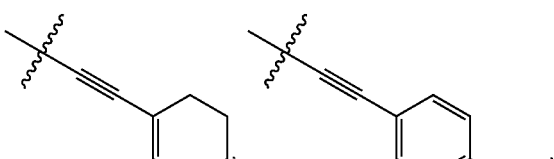

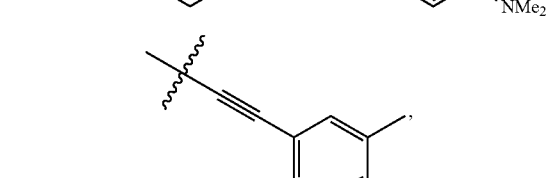

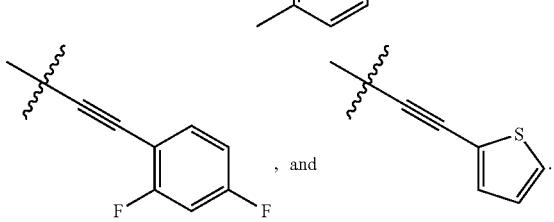

39. The compound of any of paragraphs 32-38, wherein the compound is of formula (IVa) or (IVb):

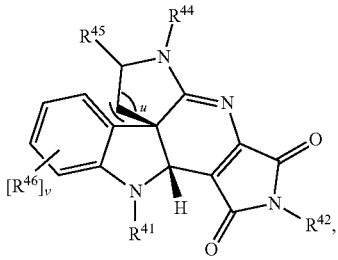

Formula (IVa)

Formula (IVb)

40. The compound of any of paragraphs 32-39, wherein v is 0.
41. The compound of any of paragraphs 32-39, wherein the compound is of formula (IVc):

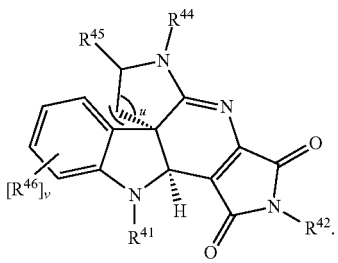

Formula (IVc)

42. A pharmaceutical composition comprising a compound of any of paragraphs 1-41 and a pharmaceutically acceptable carrier.
43. A method of treating a viral infection or preventing a disease or disorder caused by a viral infection in a subject in need thereof, the method comprising administering to the subject a therapeutically effective amount of a compound of any of paragraphs 1-41.
44. The method of paragraph 43, wherein the viral infection is a hepatitis C virus infection.
45. The method of any of paragraphs 43-44, wherein said administering is by injection, infusion, instillation, inhalation, or ingestion.
46. The method of any of paragraphs 43-45, wherein the effective amount is 1 µg/kg of body weight to 150 mg/kg of body weight.
47. The method of any of paragraphs 43-46, wherein said administering is everyday, every third day, every fourth day, every fifth day, every sixth day, or once a week.
48. The method of any of paragraphs 43-47, wherein said administering is once a day, twice a day, three-times a day, or four times a day.
49. The method of any of paragraphs 43-48, wherein administering is for a period of 1 week to 6 months.

50. The method of any of paragraphs 43-49, wherein the compound is co-administered with a second agent.
51. The method of paragraph 50, wherein the second agent is an anti-viral agent.
52. The method of any of paragraphs 50-51, wherein the second agent is selected from an interferon, ribavirin, levovirin, viramidine, isatoribine, an HCV protease inhibitor, an HCV polymerase inhibitor, an HCV IRES inhibitor, an HCV Helicase, an HCV ATPase inhibitor, an NS5A phosphorylation inhibitor, an HCV NS2 inhibitor, a-methyl-1-adamantanemethylamine, hydroxy-ethoxymethylguanine, adamantanamine, 5-iodo-2'-deoxyuridine, trifluorothymidine, adenine arabinoside, a L-nucleoside, non-immunosuppressive cyclosporins, and any combinations thereof.
53. The method of any of paragraphs 43-52, wherein the compound and the second agent are co-administered at the same time.
54. The method of any of paragraphs 43-53, wherein the subject is a mammal.
55. The method of any of paragraphs 43-54, wherein the subject is a human.
56. The method of any of paragraphs 43-55, further comprising selecting the subject to be treated by diagnosing the subject with the viral infection or a disease or disorder caused by the viral infection before onset of said administering.
57. The method of any of paragraphs 43-56, further comprising selecting a subject previously diagnosed with a viral infection or a disease or disorder caused by a viral infection before onset of said administering.
58. The method of any of paragraphs 43-57, wherein the subject is being treated for a viral infection or a disease or disorder caused by a viral infection before onset of said administering.
59. Use of a compound of any of paragraphs 1-41 for treating a viral infection or preventing a disease or disorder caused by a viral infection in a subject in need thereof, comprising administering to the subject a therapeutically effective amount of a compound of any of paragraphs 1-41.
60. The use of paragraph 59, wherein the viral infection is a hepatitis C virus infection.
61. The use of any of paragraphs 59-60, wherein said administering is by injection, infusion, instillation, inhalation, or ingestion.
62. The use of any of paragraphs 59-61, wherein the effective amount is 1 µg/kg of body weight to 150 mg/kg of body weight.
63. The use of any of paragraphs 59-62, wherein said administering is everyday, every third day, every fourth day, every fifth day, every sixth day, or once a week.
64. The use of any of paragraphs 59-63, wherein said administering is once a day, twice a day, three-times a day, or four times a day.
65. The method of any of paragraphs 59-64, wherein administering is for a period of 1 week to 6 months.
66. The use of any of paragraphs 59-65, wherein the compound is co-administered with a second agent.
67. The use of paragraph 66, wherein the second agent is an anti-viral agent.
68. The use of any of paragraphs 66-67, wherein the second agent is selected from an interferon, ribavirin, levovirin, viramidine, isatoribine, an HCV protease inhibitor, an HCV polymerase inhibitor, an HCV IRES inhibitor, an HCV Helicase, an HCV ATPase inhibitor, an NS5A phosphorylation inhibitor, an HCV NS2 inhibitor, a-methyl-1-adamantanemethylamine, hydroxy-ethoxymethylguanine, adamantanamine, 5-iodo-2'-deoxyuridine, trifluorothymidine, adenine arabinoside, a L-nucleoside, non-immunosuppressive cyclosporins, and any combinations thereof.
69. The use of any of paragraphs 59-68, wherein the compound and the second agent are co-administered at the same time.
70. The use of any of paragraphs 59-69, wherein the subject is a mammal.
71. The use of any of paragraphs 59-70, wherein the subject is a human.
72. The use of any of paragraphs 59-71, further comprising selecting the subject to be treated by diagnosing the subject with the viral infection or a disease or disorder caused by the viral infection before onset of said administering.
73. The use of any of paragraphs 59-72, further comprising selecting a subject previously diagnosed with a viral infection or a disease or disorder caused by a viral infection before onset of said administering.
74. The use of any of paragraphs 59-73, wherein the subject is being treated for a viral infection or a disease or disorder caused by a viral infection before onset of said administering.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±10%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

By "treatment", "prevention" or "amelioration" of a viral infection is meant delaying or preventing the onset, reversing, alleviating, ameliorating, inhibiting, slowing down or stopping the progression, aggravation or deterioration the progression or severity of a condition, disease and/or disorder associated with such a viral infection. In one embodiment, at least one symptom associated with the viral infection is alleviated by at least 5%, at least 10%, at least 20%, at least 30%, at least 40%, or at least 50%.

In some embodiments, HCV mRNA, e.g., serum HCV RNA amount is reduced by at least 5%, at least 10%, at least 20%, at least 30%, at least 40%, at least 50%, at least 60%, at least 70%, at least 80%, at least 90%, at least 95%, or by 100% (e.g. complete reduction) relative to a control. In some embodiments, control can be the amount of HCV RNA before onset of treatment regime.

As used herein, the term "metabolite" refers to any compound that results from the metabolism of a compound of formula (I)-(IV).

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane polarized light in different directions). Enantiomers generally have identical physical properties, such as melting points and boiling points, and also have identical spectroscopic properties. Enantiomers can differ from each other with respect to their interaction with plane polarized light and with respect to biological activity.

The designations "R" and "S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); 65 (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(-)}$ (where the sum of $F_{(+)}$ and $F_{(-)}=1$). The enantiomeric excess is defined as $*F_{(+)}-F_{(-)}*$ and the percent enantiomeric excess by $100x*F_{(+)}-F_{(-)}*$. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A nonselective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenyloin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, hydrochloric, and the like; and the salts prepared from organic acids such as acetic, trifluoroacetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The term "alkyl" refers to saturated non-aromatic hydrocarbon chains that may be a straight chain or branched chain, containing 1 to 24 carbon atoms, which may be optionally inserted with N, O, or S. For example, $C_1$-$C_6$ indicates that the group may have from 1 to 6 (inclusive) carbon atoms in it. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. The term "alkenyl" refers to an alkyl that comprises at least one double bond. Exemplary alkenyl groups include, but are not limited to, for example, ethylenyl, propylenyl, 1-butenyl, 2-butenyl, isobutylenyl, 1-pentenyl, 2-pentenyl, 3-methyl-1-butenyl, 1-methyl-2-buten-1-yl, 2-methyl-2-butenyl, 2,3-dimethyl-2-butenyl, and the like The term "alkynyl" refers to an alkyl that comprises at least one triple bond. Exemplary alkynyl groups include, acetylenyl, propynyl, 1-butynyl, 2-butynyl, 1-pentynyl, 2-pentynyl, 3-methyl-1-butynyl, and alkyls and alkenyls with a terminal C≡C.

The term "halogen" refers to any radical of fluorine, chlorine, bromine or iodine.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like. When an aryl is substituted, it can be a o-, m-, or p-substituted aryl. Exemplary substituents for aryls include, but are not limited to, halogen, hydroxy, oxo, nitro, haloalkyl, trifluoromethyl, alkyl, alkenyl, alkynyl, alkaryl, aryl, heteroaryl, cyclyl, heterocyclyl, aralkyl, alkoxy, aryloxy, amino, acylamino, alkylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, acetamido, cyano (nitriles), ureido, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 4-nitrophenyl, and the like.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

The term "optionally substituted" means that the specified group or moiety, such as an alkyl group, alkenyl group, and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halogen, hydroxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "alkoxy" refers to an —O-alkyl radical.

The term "alkylamine" refers to an alkyl substituted with an amino.

The term "mercapto" refers to an —SH radical.

The term "thioalkoxy" refers to an —S-alkyl radical.

The term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylherocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Preparation of Library 7

A library of indoline alkaloid-type compounds was prepared using inverse electron demand Diels-Alder chemistry. The initial library (7, 132 members) originated from the intramolecular cycloaddition of tryptophan derivatives with tethered 1,2,4-triazines following protocols previously reported by the inventors in Benson, et al., Tetrahedron (1999) 62: 471. (Scheme 1). The N-alkylate tryptophan derivatives were prepared by reaction of the N-Boc tryptophan methyl ester with the appropriate alkyl halide after treatment with NaH at −30 to −78° C. in THF. No racemization was observed under these conditions. The cycloaddition precursors 4 were prepared by $S_NAr$ displacements following BOC-deprotection of L-tryptophan derivatives 2 on triazine 3 as described by Benson, et al., J. Org. Chem. (1990) 55: 3257. In situ trifluoroacetylation of the nitrogen linker, accomplished by treatment with trifluoroacetic anhydride, lowers the LUMO of the heteroaromatic azadiene and thereby enables the cycloaddition to proceed immediately after acylation under the reaction conditions without isolation of intermediate. Following deacylation upon chromatography on silica gel, the cycloadducts 6, which resemble truncated Aspidosperma-type alkaloids, were obtained in good to excellent yields. The two newly generated two stereogenic centers at C1 and C9 were formed with complete stereoselectivity controlled by chirality of the tryptophan dienophile, as previously noted by Benson, et al., Tetrahedron (1999) 62: 471. The relative stereochemistry of the cycloadducts was confirmed by NOE studies as previously described by Benson, et al., 1999. The overall yields of scaffolds 6 ranged from 42% to 64% (three steps) on a 2 g scale (FIG. 1). Diversification of scaffolds then proceeded by acylation and sulfonylation of N14 with commercially available acid chlorides and sulfonylchlorides, shown in FIG. 1, producing sublibrary 7. Reactions were run on a 39 mg/scaffold scale, and the library members were purified by mass-directed HPLC, then plated for storage. Of the 162 reactions attempted, 132 produced sufficient quantities (>40 mg) for inclusion in the library. All library members were stable to storage in the solid state, as well as in DMSO solution over several months.

Scheme 1: Preparation of Library 7

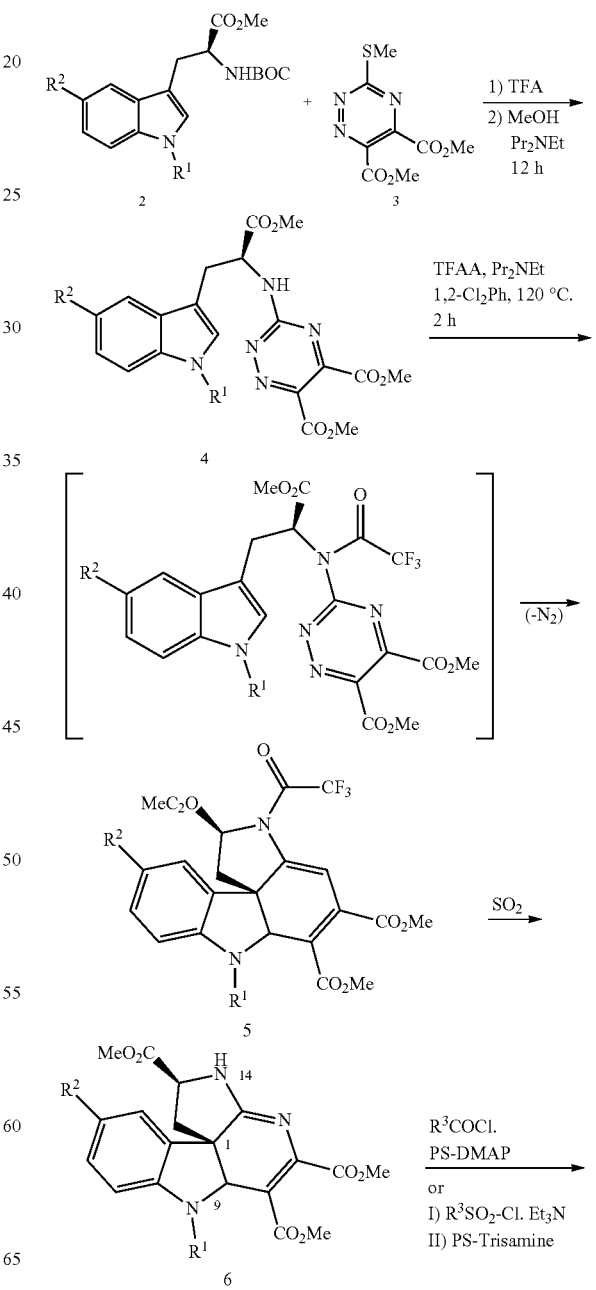

-continued

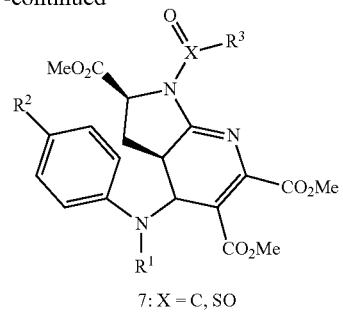

7: X = C, SO

Example 2

Preparation of δ-Lactam Library 14

Figure 3:
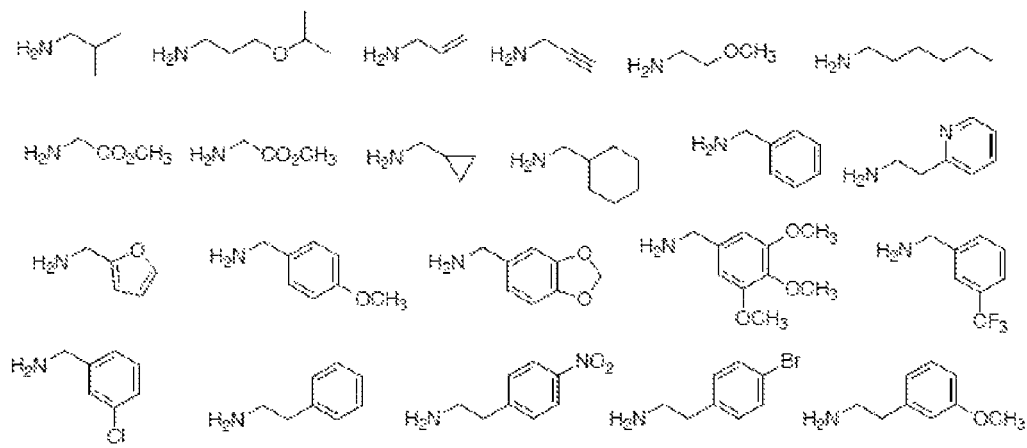
FIG. 3 shows primary amines used to diversify scaffolds 14 on the D-ring lactam nitrogen.
Figure 4:
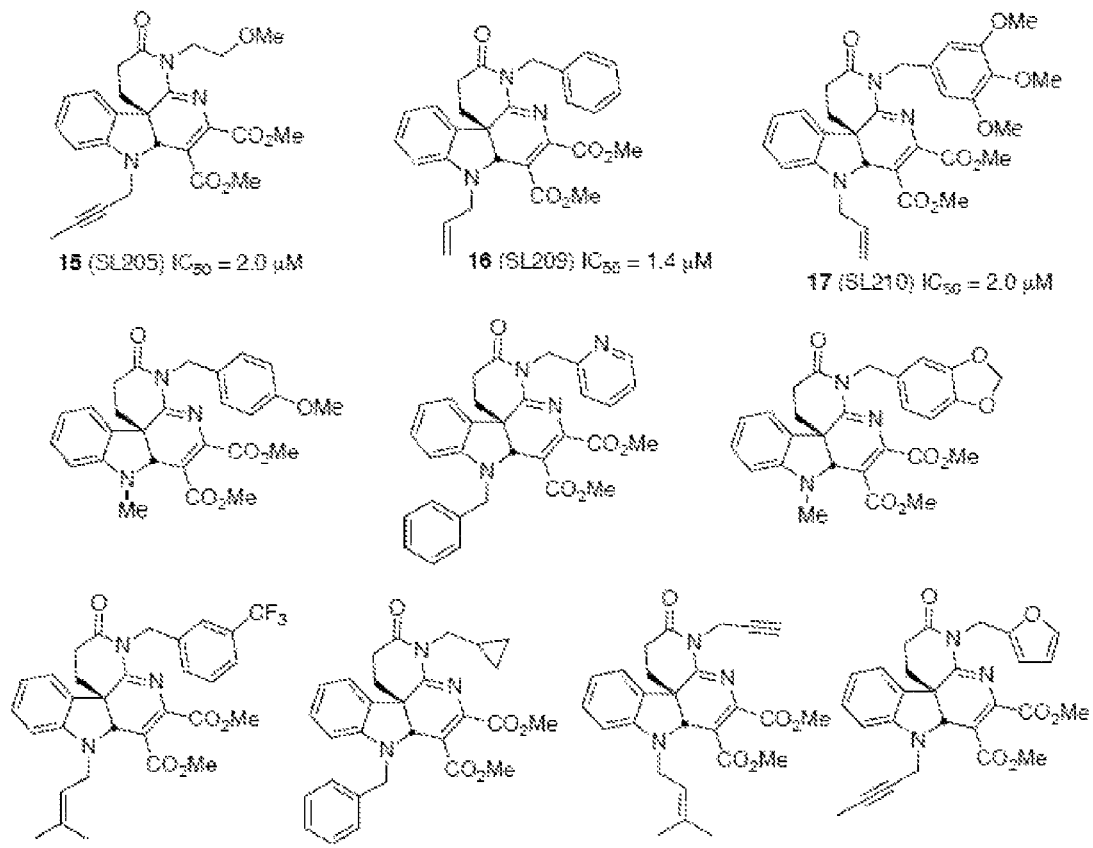
FIG. 4 shows some exemplary compounds of library 14 of Example 2. Analogues 15-17 of 1 were also active as core dimerization inhibitors in vitro. $IC_{50}$'s were determined for most active compounds.

A second generation indoline library with an expanded D-ring was prepared exploiting the intramolecular inverse electron demand Diels-Alder chemistry beginning with five N-alkylated indolylpropionic acids 8a-e and triazine 2. The indolylpropionic acids were prepared by straightforward pathways as shown in Scheme 2. For N-methylindolylpropionic acid 8a, permethylation of indolylpropionic acid, followed by basic methyl ester hydrolysis with acid work-up gave 8a in 87% yield over three steps. For the remaining acids 8b-e, methyl ester 9 formation, then N-alkylation, followed by ester hydrolysis all proceeded uneventfully in good yields. With the five indolylpropionic acids in hand, the second sublibrary again formed through an intramolecular inverse electron demand Diels-Alder reaction of an indolyl subunit with a tethered triazine, was pursued (Scheme 3). Conversion of the propionic acids to the acid chlorides 10a-e, then amidation of 10 with aminotriazines derived from 2 produced the tethered diene/dieno-phile pairs 13. Intramolecular cycloadditions by heating to 120° C. in 1,2-dichlorobenzene yielded sublibrary 14 quantitatively. Twenty-two primary amines (FIG. 3) were employed in the $S_NAr$ displacements on the chlorotriazine, producing 22 aminotriazines 12. All amidations and cycloadditions were accomplished smoothly, resulting in a 110-membered, racemic sublibrary 14; all members were stable to storage in DMSO. FIG. 4 shows some exemplary compounds from the library. Compound 15-17, from this library, were found to be the most active in vitro inhibitors of core dimerization.

Scheme 2: Preparation of indolylpropionic acids 8

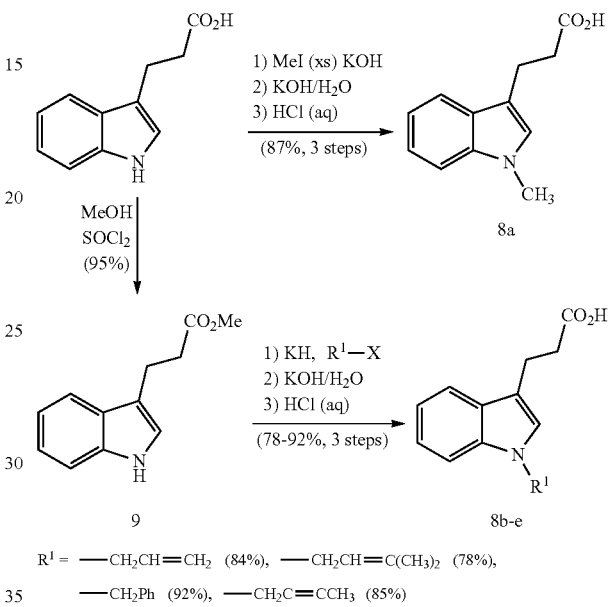

$R^1 =$ —$CH_2CH$=$CH_2$ (84%), —$CH_2CH$=$C(CH_3)_2$ (78%),
—$CH_2Ph$ (92%), —$CH_2C$≡$CCH_3$ (85%)

Scheme 3: Preparation of δ-lactam sublibrary 14 (racemic)

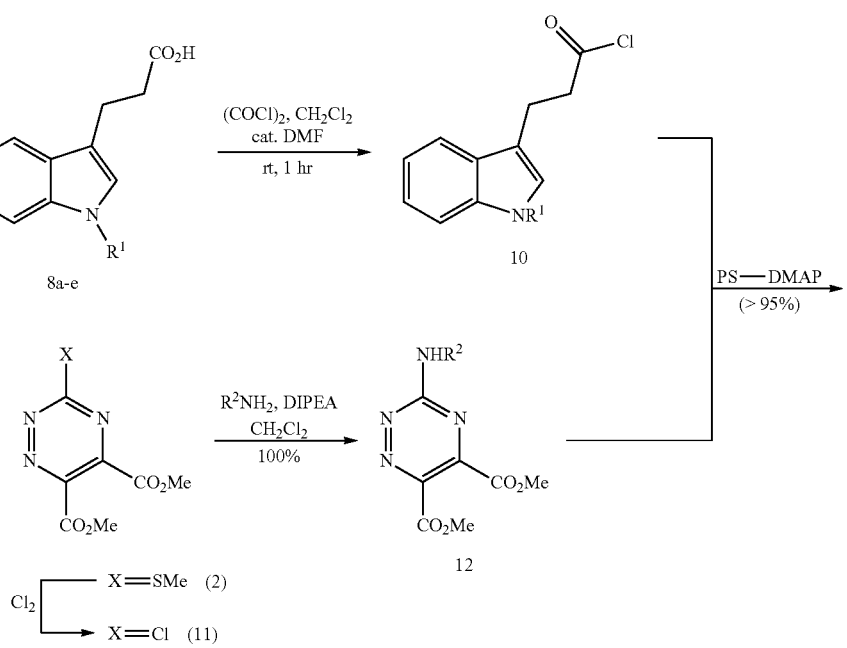

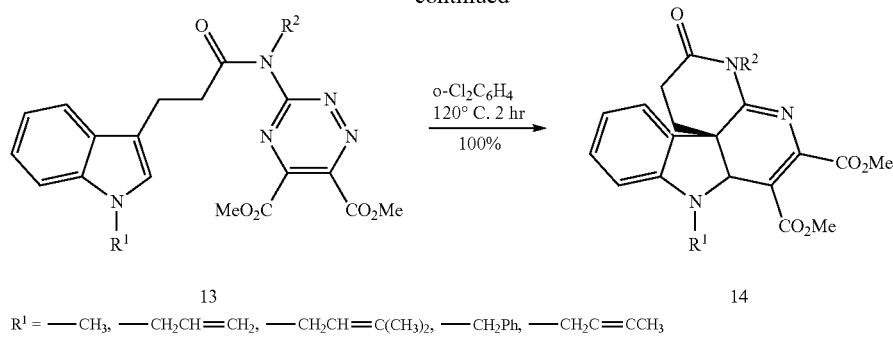

13

$R^1$ = —CH$_3$, —CH$_2$CH=CH$_2$, —CH$_2$CH=C(CH$_3$)$_2$, —CH$_2$Ph, —CH$_2$C≡CCH$_3$

14

Example 3

Synthesis of Analogues of Library 7 with Reduced Numbers of Esters

Analogues of library 7, with a reduced numbers of esters (22a and 22b), were prepared as outlined in Scheme 4. Namely, 3-(methylthio)-5-(4-nitrophenyl)-6-trifluoromethyl-1,2,4-triazine (19), was prepared with exclusive regioselectivity by the condensation of dione derived from the acidic hydrolysis of 18 with methyl carbamohydrazonothioate. Tethering with both N-methyl and N-benzyl tryptophan derivatives (20) produced 21, with the intramolecular inverse electron demand Diels-Alder reaction leading to 22a (also known as SL220) and 22b (also known as SL221), the targeted analogues 1 with two ester groups removed.

Scheme 3: Preparation of analogues 22a and 22b

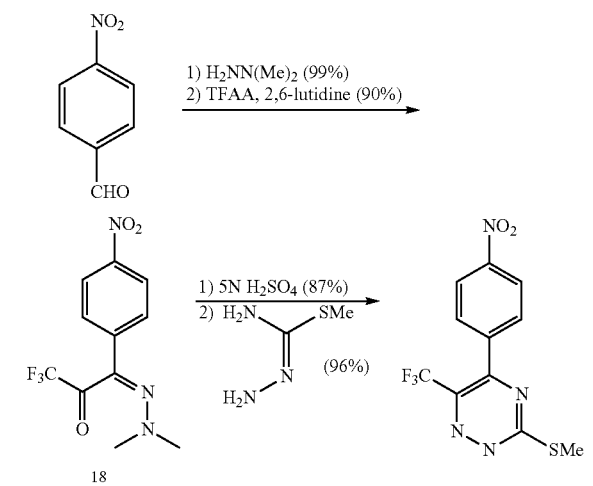

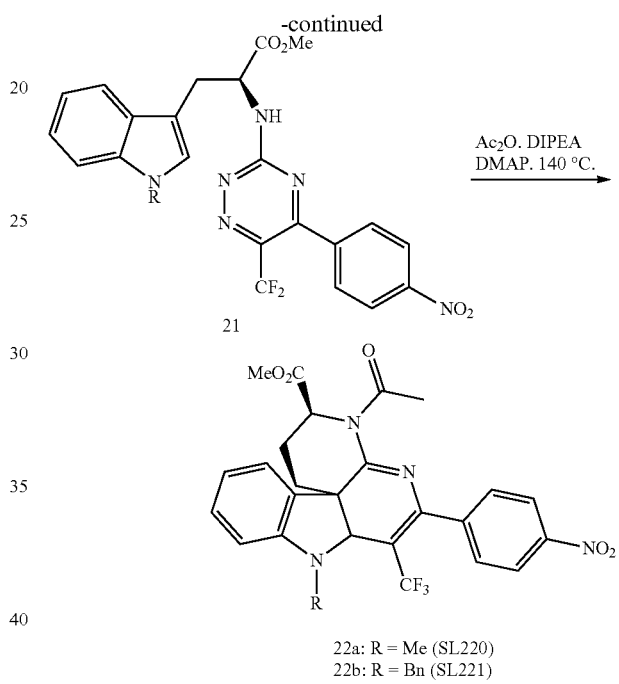

22a: R = Me (SL220)
22b: R = Bn (SL221)

Example 4

Synthesis of Dimeric Compounds

Figure 5:
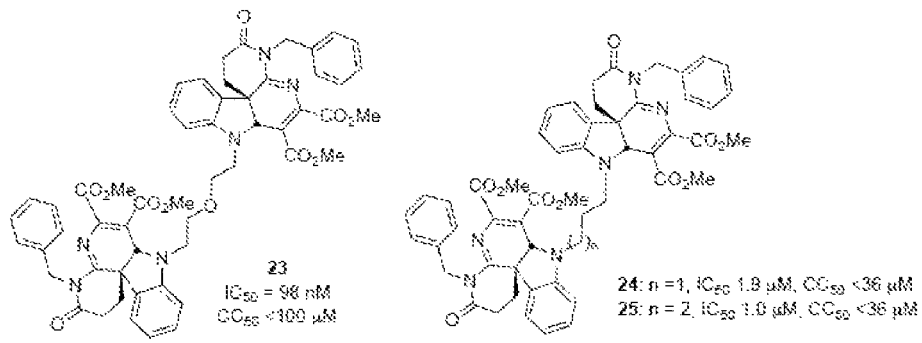
FIG. 5 shows three exemplary dimers of 16.

Dimeric compounds 23-25, shown in FIG. 5, were synthesized by standard synthetic procedures that paralleled the preparation of the monomers as described in Examples 1 and 2.

Example 5

Synthesis of Analogues 27 and 28

Triazoles 27 (SL250) and 28 (SL251) were prepared from monomer analogue 26 with the tethered alkynyl group as shown in Scheme 5.

Example 6

Cyclic Imides

Figure 6:
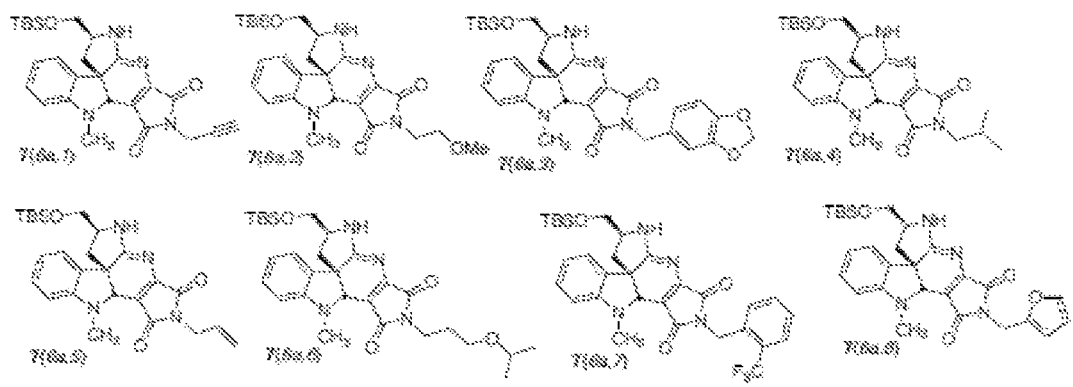
FIG. 6 shows the cyclic imide sublibrary scaffolds 7{6a,1-8}.

A library of cyclic imides was prepared utilizing eight cycloadduct scaffolds illustrated in FIG. 6. These scaffolds were prepared beginning the N—BOC tryptophan methyl ester (1, Scheme 6). Methylation of the indole nitrogen following standard procedures produced 2a (Scheme 6, RX=CH₃I, BnBr). Reduction of the methyl ester to the primary alcohol, followed by removal of the BOC group, then tethering of the triazine 3 through base promoted S_NAr displacement as gave the tethered triazines 4a,b. Protection of the primary alcohol as the TBS ether 5a,b, then cycloaddition by refluxing in dioxane in the presence of trifluoroacetic anhydride (TFAA), a reaction which proceeds by initial acylation of the tethering nitrogen, cycloaddition, loss of nitrogen gas, then deacylation (Scheme 7), yielded 6a,b.

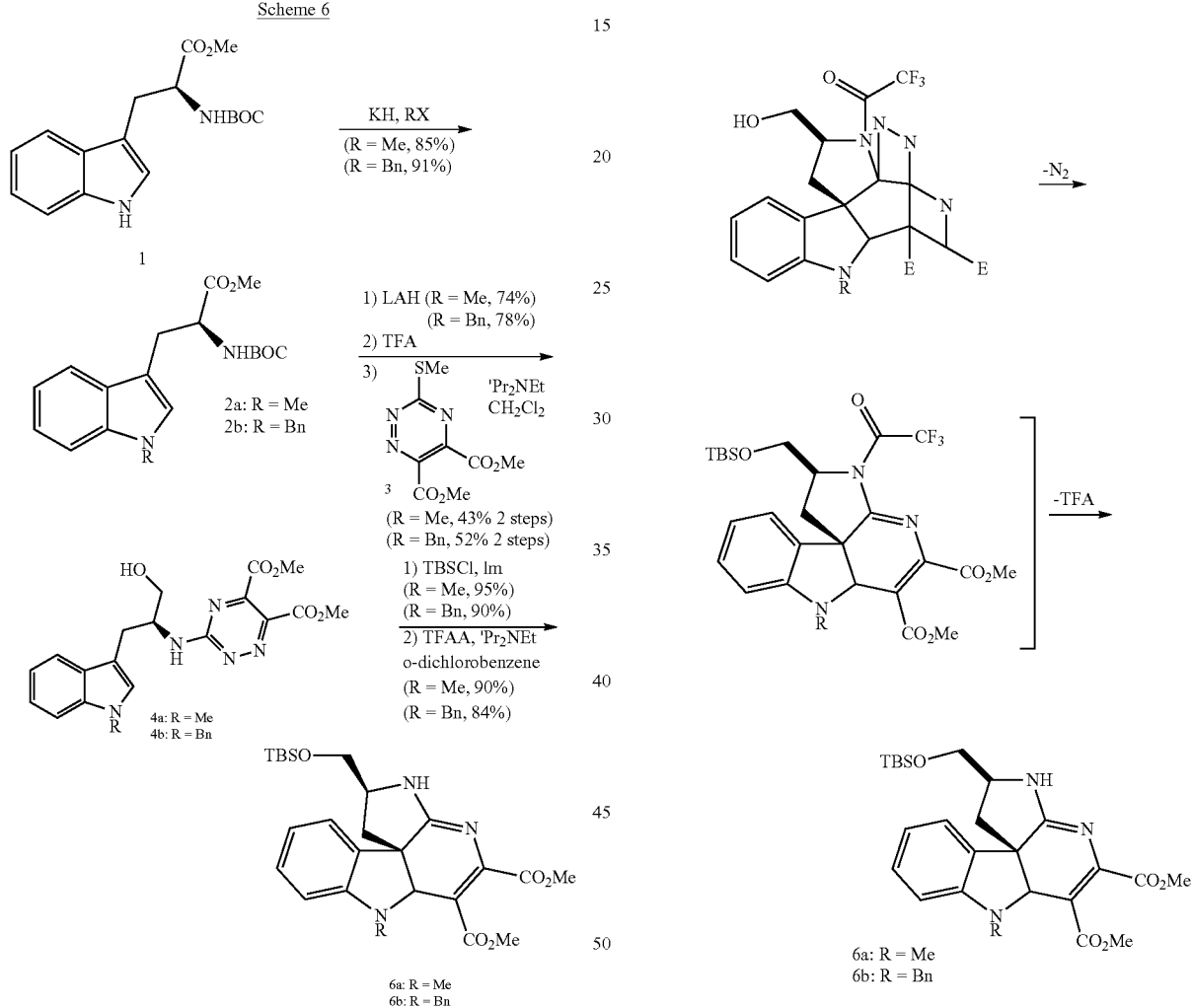

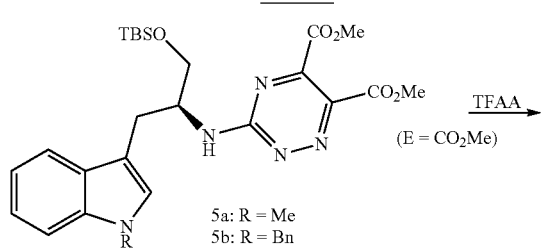

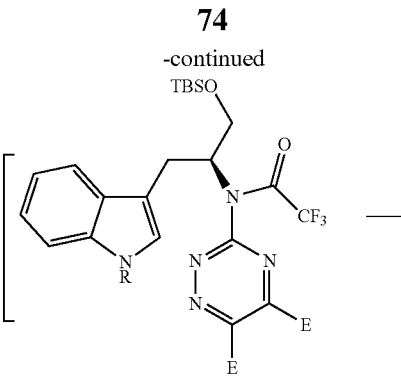

Figure 7:
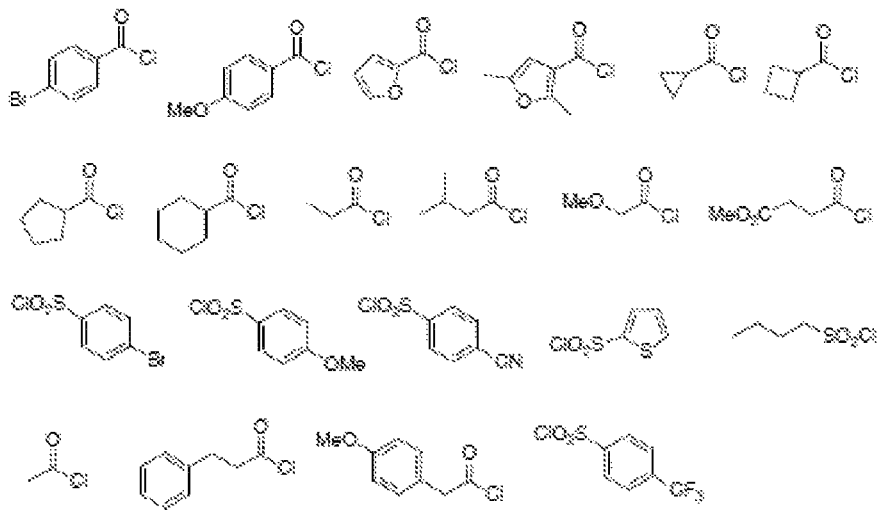
FIG. 7 shows the acylating and sulfonylating reagents for diversification of scaffolds 7{6a,1-8}.
Figure 8:
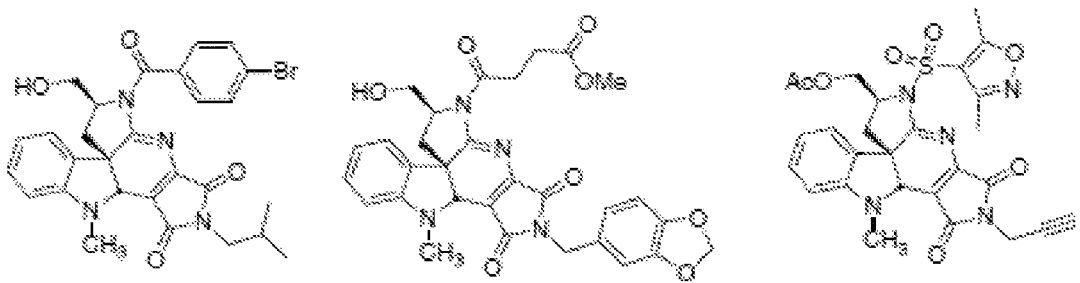
FIG. 8 shows exemplary compounds of the cyclic imide sublibrary (151 members total).

Completion of the cyclic imide scaffolds was accomplished by basic hydrolysis of both esters, then imide formation with primary amines (Scheme 8). Diversification of scaffolds 7{6a,1-8} by acylation and sulfonylation using the acyl and sulfonyl chlorides shown in FIG. 7, then desilylation with TBAF gave the first subset of 85 cyclic imide library members 8{6a,1-8,1-20}. Sixty of these members were further acetylated at the primary alcohol as well (9), to produce a total number of 151 cyclic imides, which includes the scaffolds 7{6a,1-8} themselves. Library members were purified by mass-directed LC-MS; representative examples are shown in FIG. 8. All members of this sublibrary were single enantiomers with the chirality determined by that of the starting tryptophan.

Scheme 8

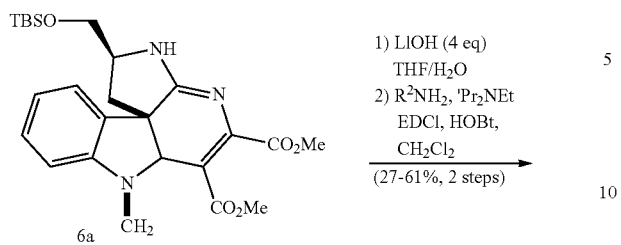

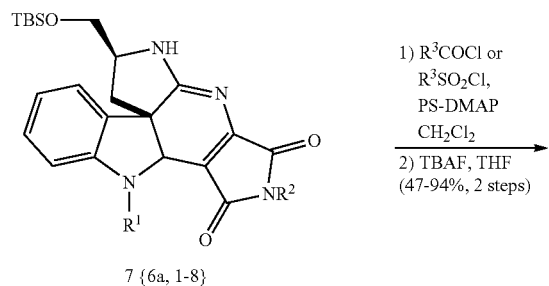

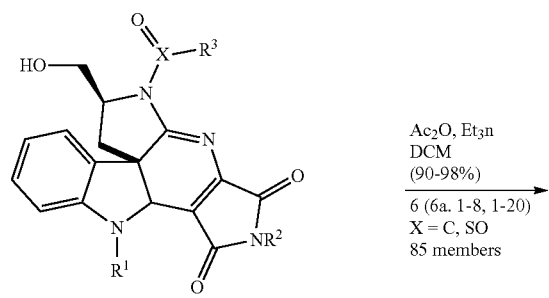

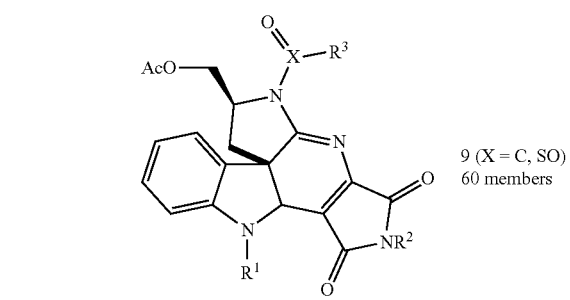

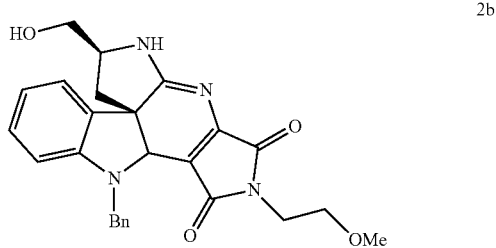 [SMILES: COCCN1C(=O)C2=C(C1=O)C1N(Cc3ccccc3)c3ccccc3[C@@]13C[C@@H](CO)NC3=N2]

Potential expansion of this cyclic imide library lies not only in diversification of the three groups $R^1$-$R^3$, but also in substitution on the indolyl benzene ring, as well as in variation of the primary alcohol acylating group, which can also include sulfonylation with sulfonyl chlorides, carbamate formation with isocyanates, and carbonates with alkyl/aryl chloroformates. Further diversification of the acylating agent (—X(O) $R^3$ subunit) can be achieved by urea formation with isocyanates, and carbamate formation with alkyl/aryl chloroformates. In addition to the library described in the preceding paragraph, select analogues, which demonstrate the potential for library expansion in subsequent generations, were prepared beginning with the N-benzyl tryptophan derivative 2b, and following the same chemistry outlined above in Scheme 6 and Scheme 8.

Example 7

Cross-Coupling Sublibraries

As shown in Scheme 4, another library was generated through cross-coupling chemistry employing members of both the original cycloadduct library described in Example 1 and the δ-lactam sublibrary of the second generation library described in Example 2. Iodination of both scaffold 10 from the original library, as well as select library members 11 from the δ-lactam sublibrary with NIS in acetonitrile occurred at rt (30 min for 10, 10 hr for 11). In all cases, exclusive regioselectivity was observed, with iodination occurring solely at the position para to the original indole nitrogen. The iodinations were successful on a multigram scale.

With the aryl iodides 12 and 14 in hand, various Pd-catalyzed cross-couplings were examined. Results are shown in Table 1. Suzuki and Sonagashira couplings (Entries 1-6), along with aryl aminations (Entries 7 and 10) all proceeded smoothly under standard conditions. In contrast, Stille coupling and aryl cyanation (Entries 8-9) were unsuccessful in the single attempts undertaken.

Scheme 9

Eq 1

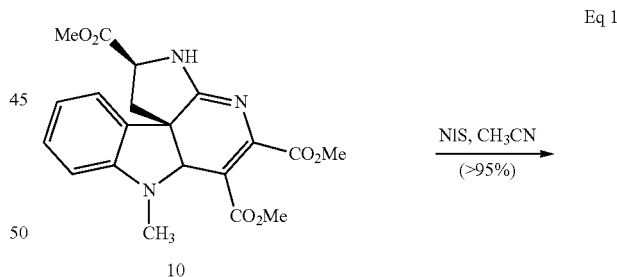

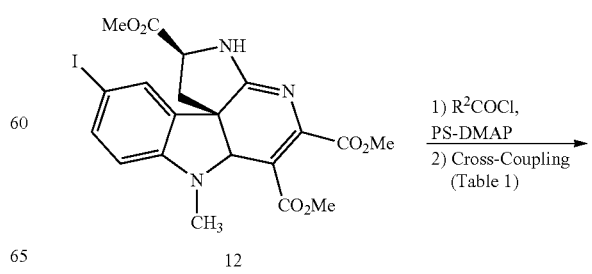

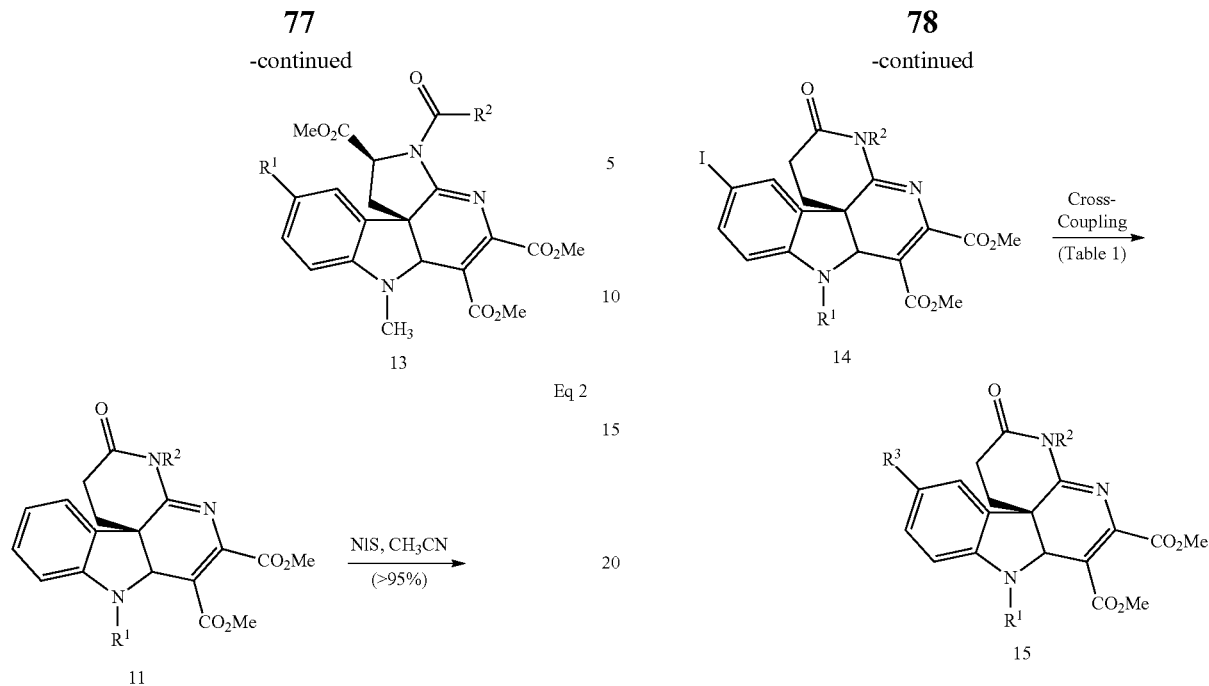
TABLE 1
Cross-Couplings of Aryl Iodides 19 and 21.

TABLE 1-continued

Cross-Couplings of Aryl Iodides 19 and 21.

| Entry | Aryl Iodide | Coupling Partner | Product[a] | Yield[a] |
|---|---|---|---|---|
| 4 | | | | 80% |
| 5 | | | | 86% |
| 6 | | | | 89% |
| 7 | | | | ND[b] |
| 8 | | ZN(CN)$_2$ | No Rxn | — |

TABLE 1-continued

Cross-Couplings of Aryl Iodides 19 and 21.

| Entry | Aryl Iodide | Coupling Partner | Product[a] | Yield[a] |
|---|---|---|---|---|
| 9 | 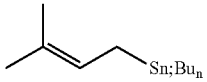 |  | No Rxn | — |
| 10 | 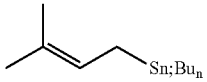 |  | 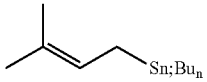 | ND[b] |

[a]Isolated yields.
[b]Not determined.

Figure 9:
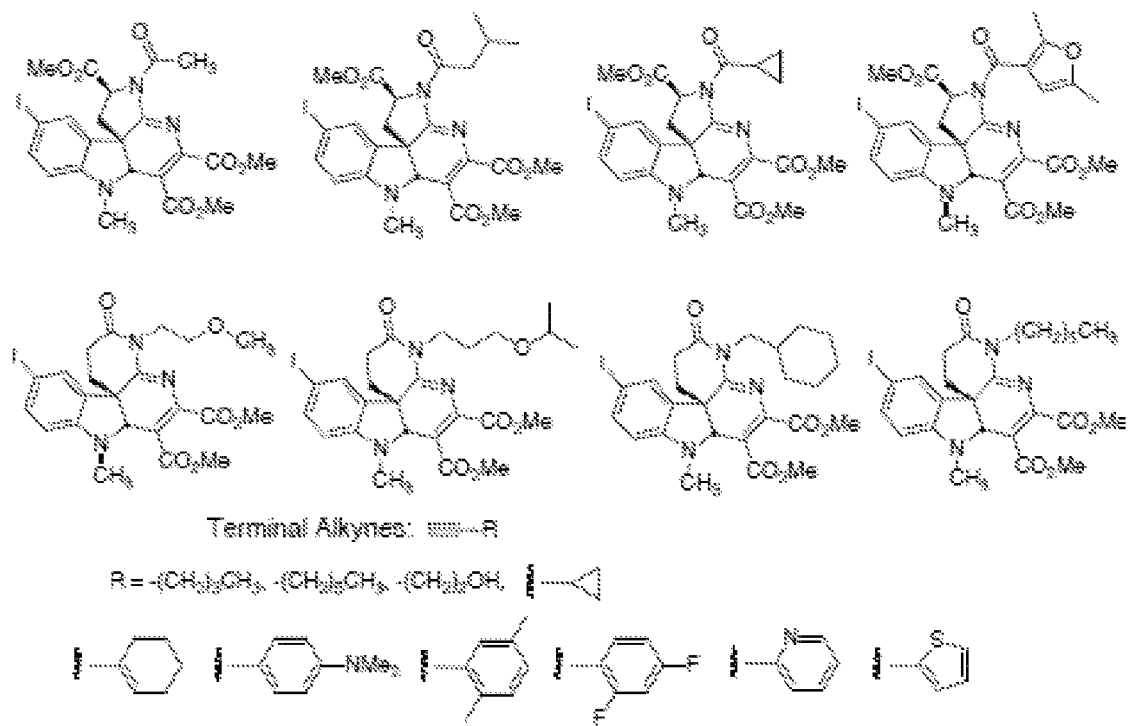
FIG. 9 shows the aryl iodides and terminal alkynes used in the cross-coupling sublibrary (80 members).
Figure 10:
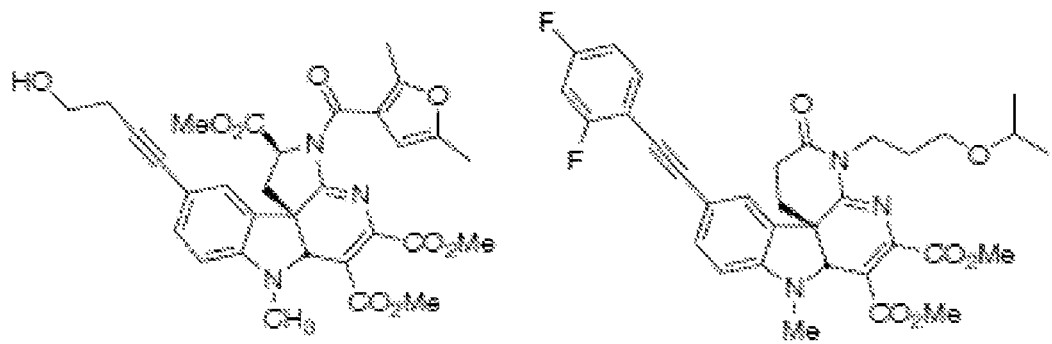
FIG. 10 shows representative members of the cross-coupling library.

Given the success with the Sonagashira couplings, a library of eighty members was prepared by Pd-catalyzed Sonagashira cross-coupling beginning with aryl iodides and terminal alkynes shown in FIG. 9, producing a library with 80 members. The products were purified by mass-directed preparative HPLC, with representative members of this sublibrary are shown in FIG. 10.

Example 8

Cyclic Imides (II)

Figure 11:
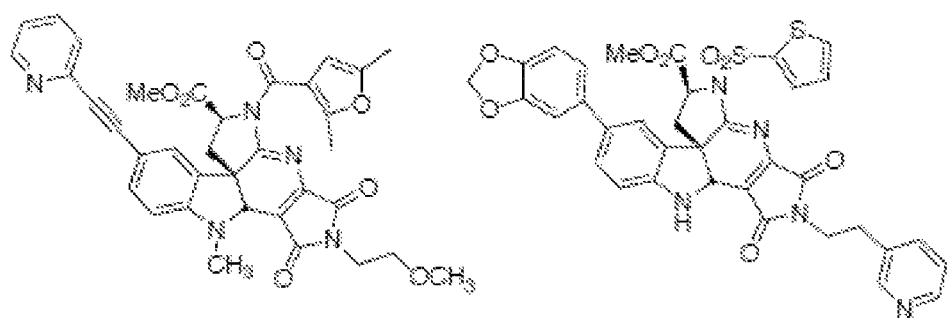
FIG. 11 shows representative members of cyclic imide library derived from cross-coupling products.

Members of the δ-lactam and cross-coupling sublibraries can be converted into cyclic imides, Scheme 10, using the chemistry described above for imide formation (Example 6, Scheme 8). For example, the primary amines depicted in FIG. 3 can be employed for preparation of δ-lactam sublibrary, though the number of primary amines is readily expanded. Cyclic imides can be produced with both 5- and 6-membered D-rings, 16 and 17, respectively. Representative members of this sublibrary are shown in FIG. 11.

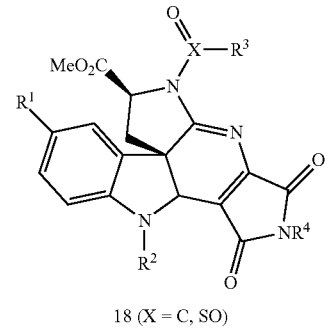

18 (X = C, SO)

Scheme 10

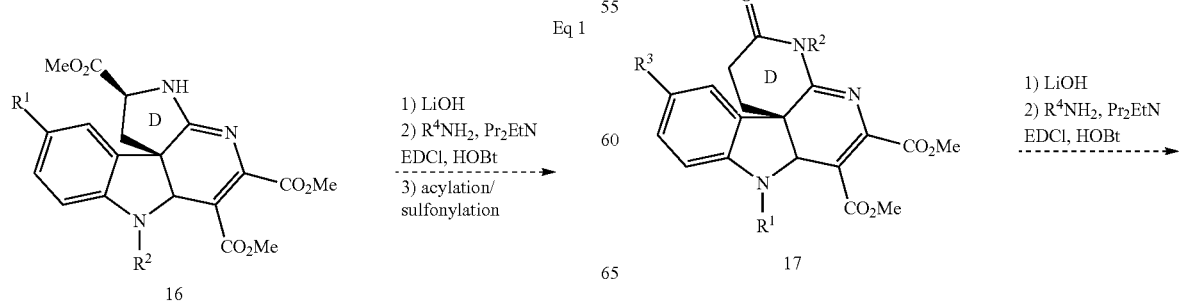

Example 9

Tetrazine-Derived Libraries

Figure 12:
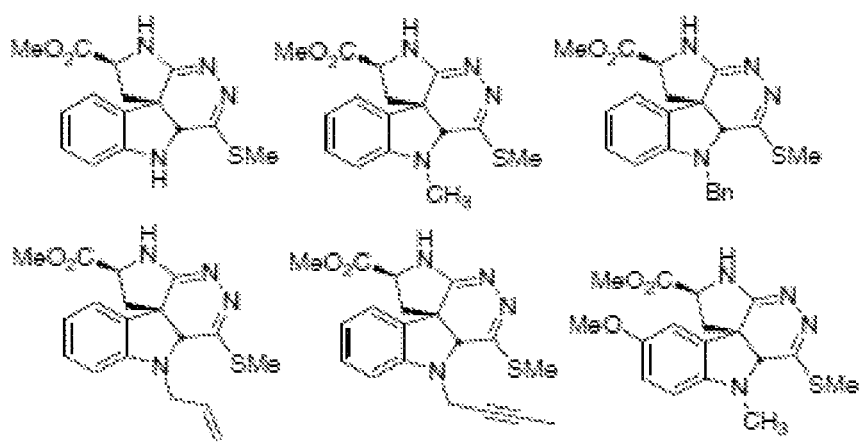
FIG. 12 shows the tetrazine/tryptophan cycloadduct scaffolds.
Figure 13:
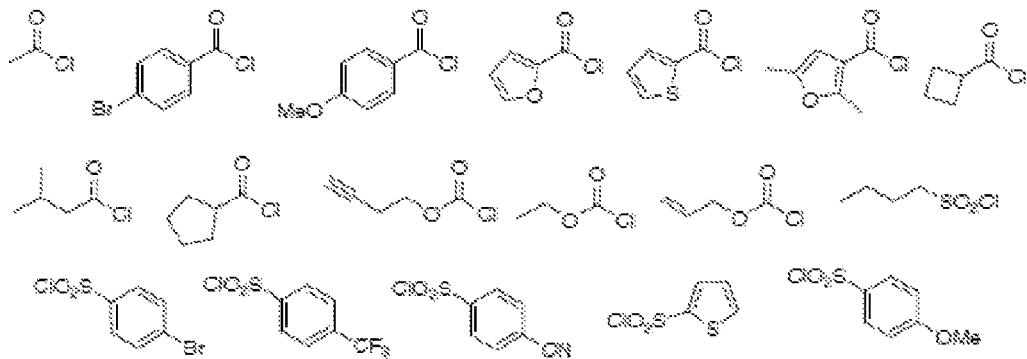
FIG. 13 shows acylating and sulfonylating reagents for diversification of tetrazine/tryptophan cycloadduct scaffolds 25 of Example 9.
Figure 14:
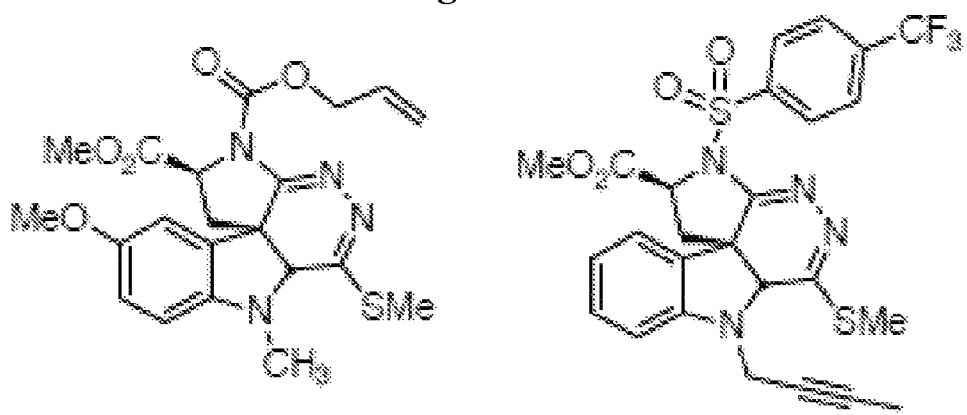
FIGS. 14 and 15 show representative examples of tetrazine/tryptophan cycloadduct library.
Figure 15:
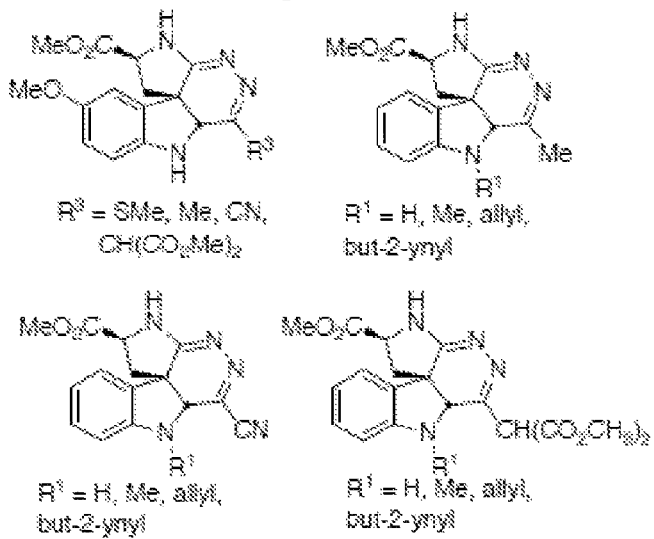

Cycloadducts formed from tryptophan tethered with tetrazines (24 and 25, Scheme 11) were previously described in Benson, et al., Tetrahedron (2000) 56: 1165-1180. These compounds were thought to be unstable on storage in DMSO, so they were not further pursued as library members in the first generation library for preliminary screening. Now, these tetrazine-derived scaffolds have been further diversified, as described for the triazine cycloadducts, by acylation and sulfonylation of 25 at the N14 nitrogen. To this end, an 82-membered library derived from six tryptophan/tetrazine cycloadduct scaffolds 25 ($R^3$=$CO_2CH_3$, FIG. 12), and commercially available acylating and sulfonylating agents (FIG. 13) were prepared. Representative members are shown in FIG. 14. For further expansion of this library, additional cycloadduct scaffolds from tethered tetrazine-tryptophan pairs have also been obtained, see FIG. 15. These scaffolds can also be further utilized for diversification with the acylating and sulfonylating agents.

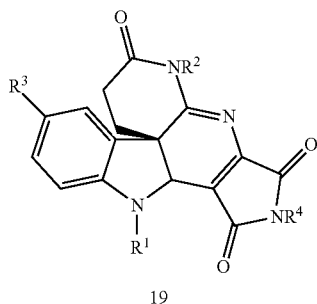

19

Scheme 11

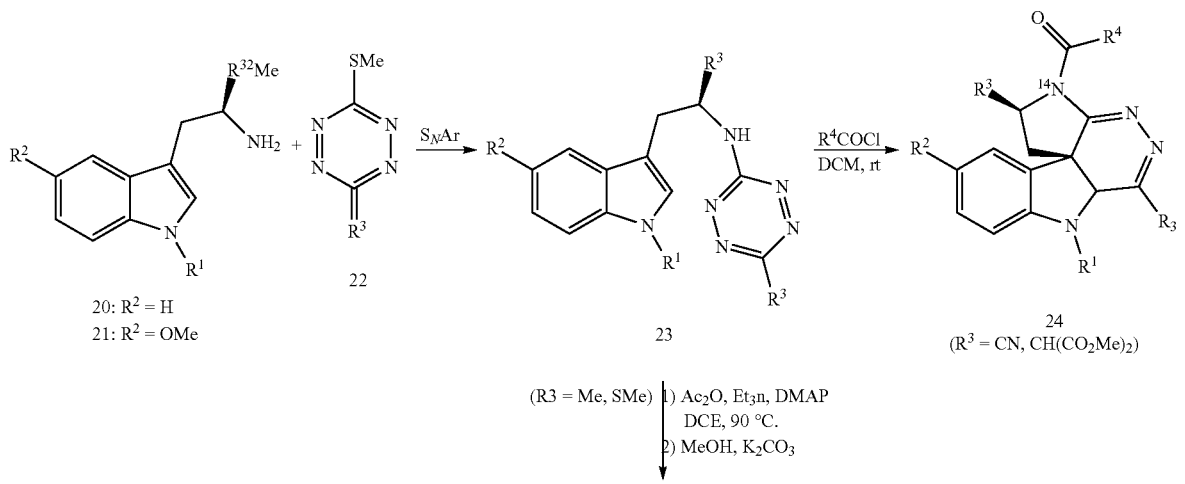

20: $R^2$ = H
21: $R^2$ = OMe

23

24
($R^3$ = CN, CH($CO_2$Me)$_2$)

(R3 = Me, SMe) 1) Ac$_2$O, Et$_3$n, DMAP
DCE, 90 °C.
2) MeOH, K$_2$CO$_3$

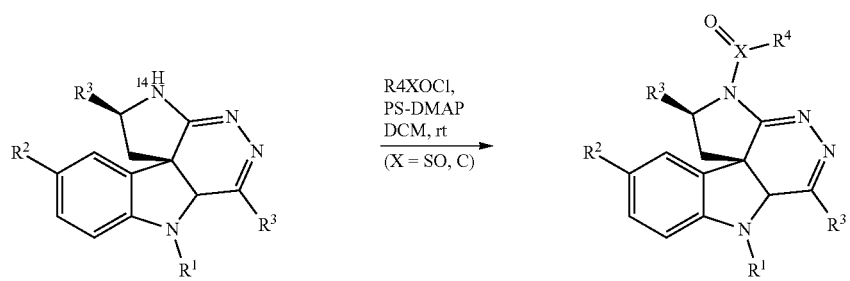

25

R4XOCl,
PS-DMAP
DCM, rt
(X = SO, C)

26

Example 10

Synthesis of Enantiomeric Compounds

All of the examples of compounds which employed tryptophan as the intramolecular dienophile, began with the natural (S)-tryptophan methyl ester. The enantiomeric compounds are readily accessible beginning with the (R)-tryptophan methyl ester. To confirm this, the inventors prepared 27 from the BOC-protected "unnatural" tryptophan methyl ester in five steps (Scheme 12) using the synthetic protocols described in Examples 1 and 2.

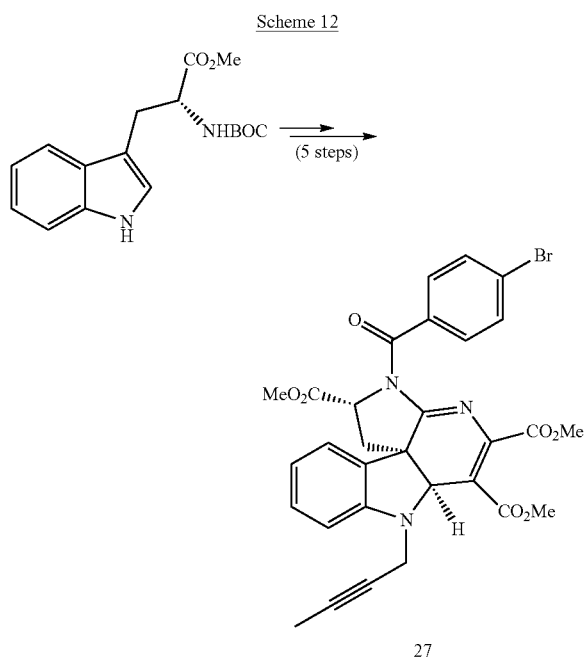

Scheme 12

27

Example 11

Biological Assays

Determination of $IC_{50}$ Values:

This assay employed the AlphaScreen® technology, a secondary Amplified Luminescent Proximity Homogeneous Assay as described in Kota, et al, J. Gen Virol. (2009) 90: 1319-1328, content of which is herein incorporated by reference. AlphaScreen is based on the use of photoactive donor and acceptor beads that recognize specific tags on interacting proteins (Peppard, 2003). Core106 dimerization was confirmed using AlphaScreen technology in which a core106 protein domain was tagged with either Glutathione-S-transferase (GST) tag or a Flag peptide tag. The untagged core106 protein domain was used as a model competitor in the assay. The proteins were diluted to working concentrations in 'protein buffer' (100 mM HEPES pH 7.5, 1 mM EDTA, 5 mM DTT, 0.1% CHAPS, 10% glycerol). The donor and acceptor beads were diluted to working concentrations in 'bead buffer' (20 mM HEPES pH7.5, 125 mM NaCl, 0.1% BSA, 0.1% CHAPS). GST-tagged core106 (150 nM) was incubated with 150 nM of Flag-tagged core106 for 1 h at room temperature. Anti-Flag acceptor beads (Perkin Elmer Lifesciences) were added to the proteins at a final concentration of 20 μg/ml and incubated for 1 h at room temperature. Then, Glutathione donor beads (Perkin Elmer Lifesciences) were added to the proteins at a final concentration of 20 μg/ml and incubated for 1 h. The assays were executed in a white 384 well Packard opti plate (Perkin Elmer Lifesciences) and were read on Perkin Elmer Envision.

Uninhibited or 0% inhibition control is defined as wells containing only GST-core106 and Flag-core106. 100% inhibition control is defined as wells containing GST-core106 and Flag-core106 with core106 as an inhibitor. Test compound is wherein the test compound is analyzed.

Compounds were tested in triplicate in a 10-point series starting at a nominal test concentration of 50 nM. For each test compound, percent inhibition was plotted against compound concentration. A four parameter equation describing a sigmoidal dose-response curve was plotted using GraphPad Prism® (GraphPad Software Inc). The reported $IC_{50}$ values were generated from fitted curves by solving for the X-intercept value at the 50% inhibition level of the Y-intercept value.

Determination of $CC_{50}$ Values:

This assay utilized the compound XTT (2,3-bis[2-methoxy-4-nitro-5-sulfophenyl]-2H-tetrazolium-5-carboxyanilide inner salt) with addition of an electron coupling agent phenazine methosulfate (PMS) to measure mitochondrial dehydrogenases activity in living cells, e.g., Huh-7.5 cells. Dehydrogenases in mitochondria of living cells cleave the tetrazolium ring of XTT changing the color of the solution from clear to orange. As designed, compounds that reduce cell viability will reduce activity of the mitochondrial dehydrogenases, and leave a decreased orange color in solution.

The Huh-7.5 cell line was routinely cultured in 15-cm dishes at 37 degrees C. and 95% relative humidity (RH). The growth media consisted of DMEM supplemented with 10% v/v certified fetal bovine serum, 4 mM L-glutamine, 1 mM sodium pyruvate, 1× antibiotic mix (penicillin, streptomycin, and glutamine), and 1× non-essential amino acids.

Prior to the start of the assay 8000 cells in 100 microliter volume of colorless growth media were dispensed into each well of 96-well tissue culture-treated microtiter plates and incubated overnight at 37 degrees C. (5% CO2, 95% RH) to allow cells to adhere to the plate. The next day, 100 microliter of test compound in DMSO (1.25% final DMSO concentration) and DMSO only were added to wells. Wells with only test compound in media without cells were used to normalize the data (to account for the color a test compound may have). Next, the plates were incubated for 72 hours at 37 degrees C. (5% $CO_2$, 95% RH). Solution of XTT-PMS was prepared in 1×PBS and added to the cells in 50 microliter volume to each well and incubated for 4 hours at 37 degrees C. (5% CO2, 95% RH). After equilibrating the plates to room temperature for 10 minutes, optical density at 450 nM and 650 nM was measured on Biotek plate reader.

The percent inhibition for each compound was calculated as follows:

% Inhibition=((DMSO Control−Test compound)/
DMSO Control)*100, wherein Test compound is
defined as wells containing test compound.

Compounds were tested in triplicate in a 7-point 1:3 dilution series starting at a nominal test concentration of 320 micromolar. For each test compound, percent inhibition was plotted against compound concentration. A four parameter equation describing a sigmoidal dose-response curve was then fitted with adjustable baseline using MicroSoft Excel software. The reported $CC_{50}$ values were generated from fitted curves by solving for the X-intercept value at the 50% inhibition level of the Y-intercept value. In cases where the highest concentration tested (i.e. 40 micromolar) did not result in greater than 50% inhibition, the $CC_{50}$ value was determined manually as greater than 320 micromolar.

Determination of $EC_{50}$ Values:

In this assay HCV infectivity is measured using real-time RT-PCR to monitor changes in expression of HCV 2a J6/JFH-1 RNA. Cells are incubated with test compound in the presence of HCV, followed by isolation of RNA, conversion to cDNA, and Taqman-based QPCR. As designed, a compound that inhibits HCV infectivity will reduce HCV RNA expression, leading to decreased production of the PCR amplicon, thereby reducing fluorescence, and increasing Ct.

Huh-7.5 cells were plated the day before the assay. After allowing the cells to adhere overnight, test compound was prepared in HCV supernatant by making 1:10 serial dilutions from 100 micromolar down to 0.001 micromolar. Doses of test compound in virus were added to cells and incubated for 24 hours. The next day, cell culture media was removed from each well and replaced with same dilutions of compound in complete media were added to cells and incubated for another 48 hours for T1 timepoint. Then cells were lysed and RNA was isolated using the RNeasy kit (QIAGEN, Valencia, Calif.). Supernatant from T1 was transferred to fresh naïve cells and incubated for 24 hours. Culture media were removed from cells and replaced with complete media and incubated for 48 hours for T2 timepoint. Cells for T2 timepoint were lysed and RNA was isolated using the RNeasy kit (QIAGEN, Valencia, Calif.). DNA was generated using the Taqman reverse transcription kit (Applied Biosystems, Foster City, Calif.). Quantitative real-time polymerase chain reaction (PCR) was performed in triplicate using LightCycler RNA Amplification Kit HybProbe master mix (Roche) with Taqman MGB Probe 6FAM-TATGAGTGTCGTGCAGC-CTC-MGBNFQ on a model LightCycler480 real time PCR system (Roche). Data are expressed as the mean fold change plus or minus SE of 3 replicates normalized to 100 ug total RNA. Primers used were forward CTTCACGCA-GAAAGCGTCTA and reverse CAAGCACCCTATCAG-GCAGT. The range of activity was normalized based on measurement of total RNA. Compounds were tested in triplicate in a 6-point 1:10 dilution series starting at a nominal test concentration of 100 micromolar.

Discussion

Figure 16:
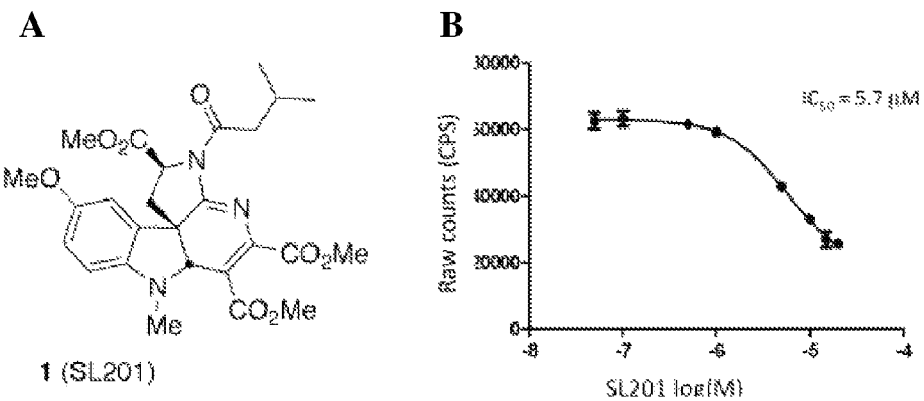
FIG. 16a shows structure of compound 1 (SL201).
FIG. 16b is a dose-response analysis of compound 1 (SL201). Core106 ALPHA screen assay was used for the dose-response analyses. The compound was dosed from 0 to 100 μM. The $IC_{50}$ was calculated using a non-linear regression 'Log (inhibitor) versus response' with four points for each concentration.

To achieve the discovery of small molecules as drug candidates which bind to Core and thereby inhibit HCV replication, a bioassay, described in Kota, et al., *ASSAY Drug Dev. Tech*, (2009) 8: 96 content of which is herein incorporated by reference, was employed to screen for inhibitors of Core dimerization. Compound 1, designated as SL201, was the most active inhibitor found, IC$_{50}$ 5.7 μM, upon screening 132 members of library 7, from Example 1, using the AlphaScreen® technology as described in Kota, et al, *J. Gen Virol.* (2009) 90: 1319-1328. FIG. 16 shows the structure of compound 1 along with a dose-response curve. Screening the library 14, from Example 2, using the AlphaScreen® technology identified 10 compounds that inhibited Core dimerization when screened at 15 μM. See FIG. 4. Three of these compounds (15-17) showed IC$_{50}$ values of 10 μM or less.

Figure 17:
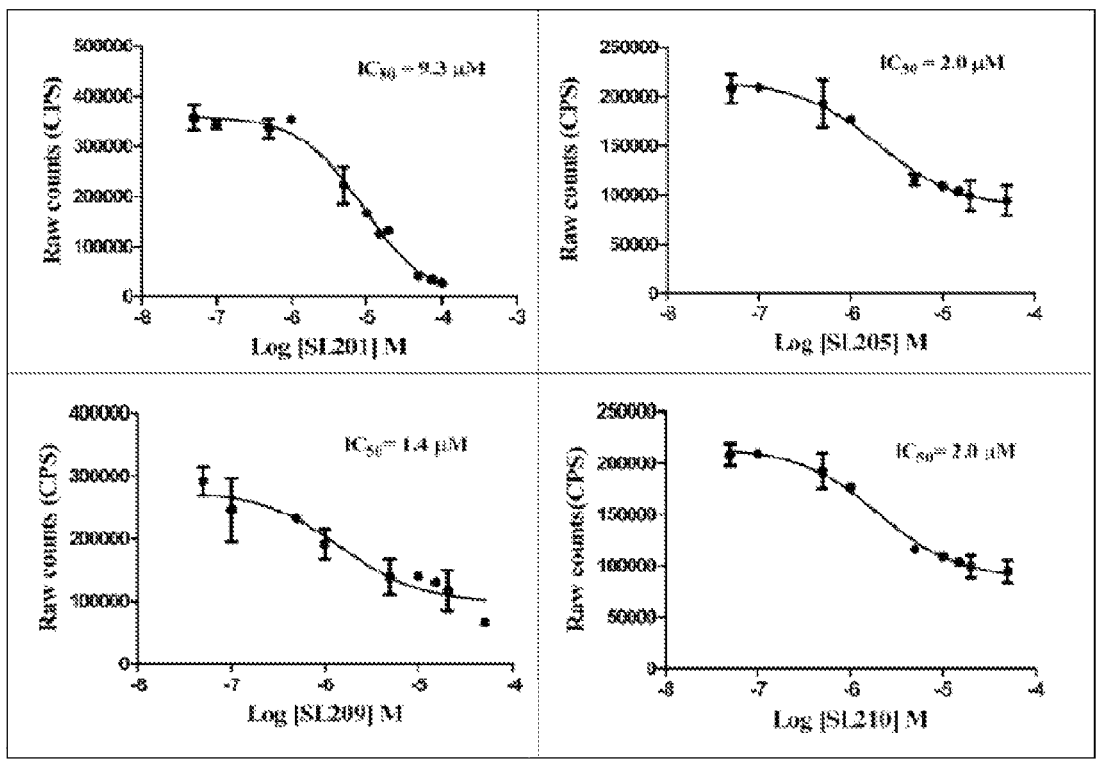
FIG. 17 shows the dose-response analyses of 1 (SL201), 15 (SL205), 16 (SL209), and 17 (SL210). Core106 ALPHA screen assay was used for the dose response analyses. The compounds were dosed from 0 to 100 μM. The $IC_{50}$ were calculated using a nonlinear regression "Log (inhibitor) vs. response" with 4 points for each concentration. The difference in $IC_{50}$ for compound 1 (SL201) is due to the using two different lots of SL201 and the values are within experimental error.

Of these compounds 1, 15-17, compound 1 (SL201) is homochiral, while all of the analogues of library 14 were prepared as racemic mixtures. The activities of the most active compounds 1, and 15-17 were validated by resynthesis and resubmission to the assay, then further evaluated for cytotoxicity and in vivo efficacy (Table 2, FIG. 17). Cytotoxicity was evaluated with hepatoma Huh7-5 cells (Table 2, column 2). Half-maximal cytotoxicity concentrations (CC$_{50}$'s) demonstrated that compounds 1, 15, and 16 were either non-cytotoxic, or showed cytotoxicity at concentrations well above the IC$_{50}$ values (1 CC$_{50}$>320 μM; 15 CC$_{50}$>320 μM; 16 CC$_{50}$=127 μM). In contrast, compound 17 was cytotoxic against this cell line at a concentration only twice that of the IC$_{50}$ for inhibition of core dimerization (17 CC$_{50}$=5.3 μM).

The compounds were then studied in the same Huh7-5 cells infected with HCV 2a strain J6/JFH-1 (Kota, et al., ASSAY Drug Dev. Tech (2009) 8: 96). Huh-7.5 hepatoma cells were electroporated with RNA from HCV and the 72-hour supernatant was used as a source of infectious virus. This supernatant was combined with compounds identified as inhibitors of core dimerization. Two stages of infection were studied: early stage (T1), corresponding to the initial 72-hour culture of naïve cells infected in the presence of the inhibitor, and late stage (T2), corresponding to the second 72-hour passage through naïve cells. HCV RNA detected in T1 results from actual viral infection and replication. HCV RNA detected in T2 results from infectious virus secreted in T1 and replicated in freshly infected naïve cells. Real-time reverse-transcriptase PCR was done on RNA extracted and purified from the cells treated with increasing concentrations (0.001-100 μM) of each of the compounds. The EC$_{50}$'s were calculated at an early (T1) and late (T2) stage, and varied from 2.3 to 14.8 μM at T1, and from 0.7 to 22.2 μM at T2, data shown in Table 2. For comparative purposes, data for BILN2061 known inhibitor of the NS3/NS4A protease (Lamarre, et al., Nature (2003) 426: 186), is included. All four were shown to be effective in inhibiting HCV 2a strain J6/JFH-1 proliferation in isolated hepatoma cells, with the relatively non-toxic 15 and 16 having EC50's in the single digit μM range.

TABLE 2

Summary of Activities for Inhibitors 1 and 15-17.

| Compound | CC$_{50}$$^a$ (μM) | IC$_{50}$$^b$ (μM) | HCV2a T1-EC$_{50}$ (μM)$^c$ | J6/JFH-1 T2-EC$_{50}$ (μM)$^c$ |
|---|---|---|---|---|
| BILN2061 | 5.3 | N/A | 0.072 | 0.071 |
| 1 | >320 | 9.3 | 14.8 | 22.2 |
| 15 | >320 | 2.0 | 4.9 | 0.7 |
| 16 | 127.2 | 1.4 | 2.3 | 3.2 |
| 17 | 5.3 | 2.0 | 3.8 | 3.0 |

$^a$50% Cytotoxic concentration vs Huh7-5 hepatoma cells; average of triplicate runs.
$^b$See FIG. 17.
$^c$EC$_{50}$'s average of triplicate runs.

With the data from preliminary screening in hand, attention was turned to three areas. First, designing core dimerization inhibitors with fewer or no ester groups. Second, designing core inhibitors with greater activity based on the structural core of inhibitors 1, and 15-17. Third, generate third generation compound libraries with additional diversity for screening.

Figure 18:
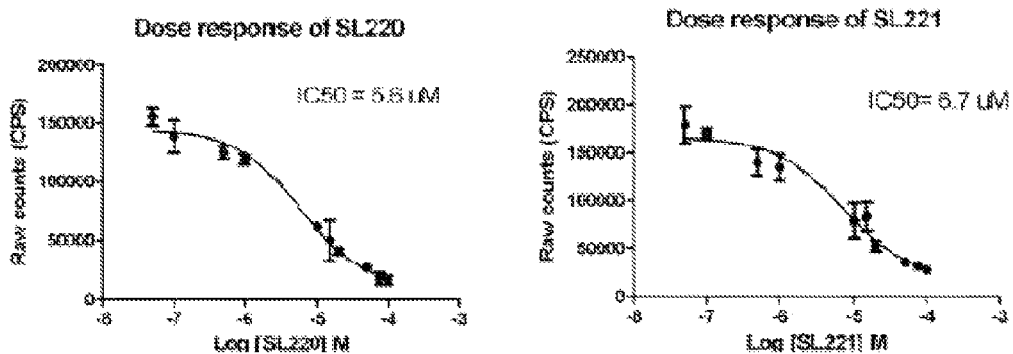
FIG. 18 shows the dose-response analyses of 22a (SL220) and 22b (SL221). Core106 ALPHA screen assay was used for the dose response analyses. The compounds were dosed from 0 to 100 μM. The $IC_{50}$ were calculated using a nonlinear regression "Log (inhibitor) vs. response" with 4 points for each concentration.

The first goal was achieved by the design of new 1,2,4-triazines capable of participating in the intramolecular inverse electron demand Diels-Alder reaction when tethered to a tryptophan and tryptamine dienophile (Example 3, Scheme 4). Initial studies focused on 3-(methylthio)-5-(4-nitrophenyl)-6-trifluoromethyl-1,2,4-triazine, which was prepared with exclusive regioselectivity by the condensation of dione derived from the acidic hydrolysis of 18 with methyl carbamohydrazonothioate. Tethering with both N-methyl and N-benzyl tryptophan derivatives produced 21, with the intramolecular inverse electron demand Diels-Alder reaction leading to 22a (also known as SL220) and 22b (also known as SL221), the targeted analogues 1 with two ester groups removed. Both 22a (IC$_{50}$=5.6 μM) and 22b (IC$_{50}$=6.7 μM) inhibited core dimerization in the single digit μM range (FIG. 18).

Since core dimerization is a protein-protein interaction, and hence the inhibitors of core dimerization are protein-protein interaction inhibitors, the search for more potent compounds began with the preparation of dimers of 16, the most potent inhibitor identified to date at 1.4 μM IC$_{50}$. While compound 23 with the monomeric subunits linked through a diethylether tether was significantly more potent (IC$_{50}$=98 nM), this dimer was also significantly more toxic (CC5$_{50}$<100 μM) than then monomer 16 (FIG. 4). The dimers with the all carbon tethers, 24 (5-carbon tether) and 25 (3-carbon tether) were only slightly more active than 16, but significantly more cytotoxic.

Figure 19:
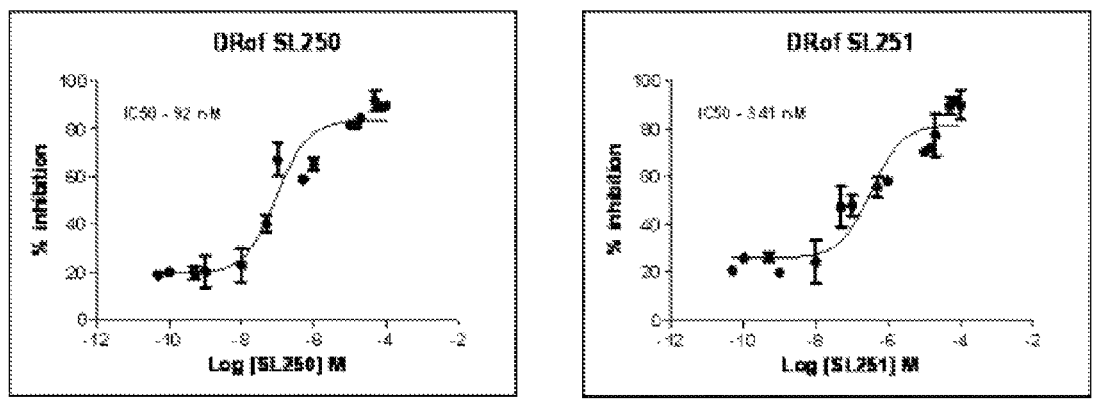
FIG. 19 shows the dose-response analyses of 27 (SL250) and 28 (SL251). Core106 ALPHA screen assay was used for the dose response analyses. The compounds were dosed from 0 to 100 μM. The $IC_{50}$ were calculated using a nonlinear regression "Log (inhibitor) vs. response" with 4 points for each concentration.

The activity of the dimers established, dimer analogues with lower molecular weights were next prepared. To this end, triazoles 27 (SL250) and 28 (SL251) were prepared from monomer analogue 26 with the tethered alkynyl group (Example 5, Scheme 5). Both triazoles showed sub-micromolar levels of inhibition of core dimerization (FIG. 19), with 27 having an IC$_{50}$ of 92 nM. This level of activity was comparable to the in vitro activity observed for the dimer 23. Thus, replacing the second monomeric unit of dimer 23 with a smaller heterocycle (the triazole) reduces the molecular weight from the dimer (MW=961) to MW=702 for 27.

Figure 20:
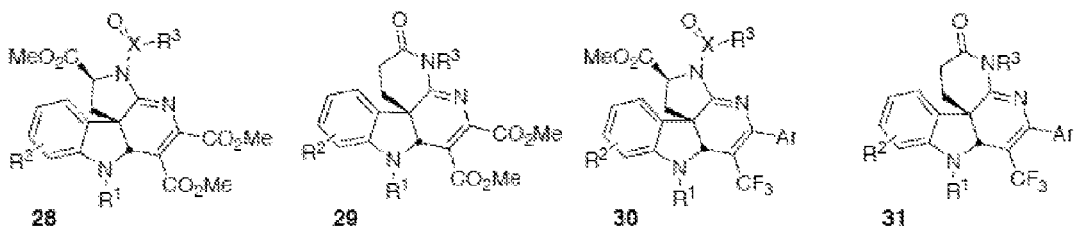
FIG. 20 shows exemplary subclasses of inhibitors of core dimerization.

Accordingly, the invention provides at least four subclasses of core dimerization inhibitors 28-31 (FIG. 20). Members of the subclasses 28-30 have been prepared and shown to inhibit core dimerization. Members of the 28 and 29 subclasses have also been shown to inhibit HCV proliferation in whole cell assays (data not shown). Importantly, these results also demonstrate that tethering a second aromatic or other heterocyclic ring as part of the substituent R$^1$ can lead to enhanced activity. Table 3 summarizes the activity of some of the exemplary inhibitors.

TABLE 3

Summary of Activities for Inhibitors 1 and 15-17.

| CMLD ID | Structure | SL number | IC$_{50}$ [µM] | CC$_{50}$ [µM] | HCV 2A [µM] T1 - EC$_{50}$ | HCV 2A [µM] T2 - EC$_{50}$ |
|---|---|---|---|---|---|---|
| CMLD 003452 | 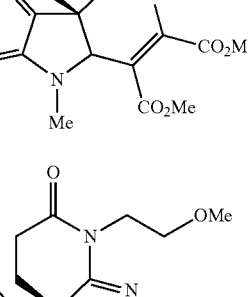 | SL201 | 9.3 | >320 | 8.8 | 8.1 |
| CMLD 005040 | 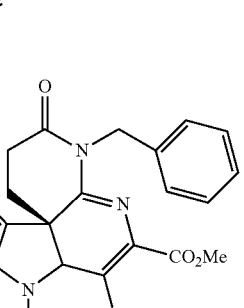 | SL205 | 2 | >320 | 4.9 | 0.7 |
| CMLD 005699 | 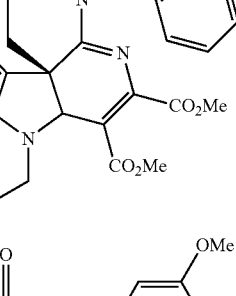 | SL209 | 1.4 | 127.2* | 2.3 | 3.2 |
| CMLD 005084 | 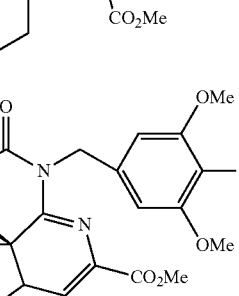 | SL210 | 2 | 5.3 | 3.8 | 3 |

TABLE 3-continued

Summary of Activities for Inhibitors 1 and 15-17.

| CMLD ID | Structure | SL number | IC$_{50}$ [µM] | CC$_{50}$ [µM] | HCV 2A [µM] | |
|---|---|---|---|---|---|---|
| | | | | | T1 - EC$_{50}$ | T2 - EC$_{50}$ |
| NA (De-esterified comp 1) | 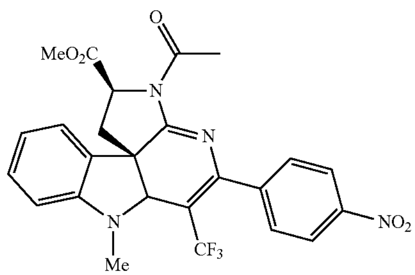 [SMILES: COC(=O)[C@@H]1C[C@@]23C(=NC(c4ccc([N+](=O)[O-])cc4)=C(C(F)(F)F)C2N(C)c2ccccc23)N1C(C)=O] | SL220 | 5.6 | 309.7 | 1.3 | 0.9 |
| NA (De-esterified comp 2)) | 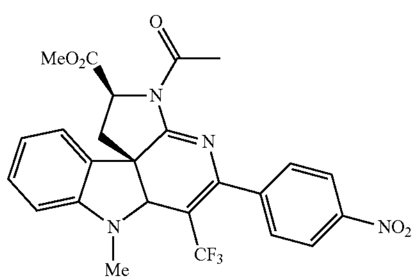 [SMILES: COC(=O)[C@@H]1C[C@@]23C(=NC(c4ccc([N+](=O)[O-])cc4)=C(C(F)(F)F)C2N(C)c2ccccc23)N1C(C)=O] | SL221 | 6.7 | 3.3 | 14.1 | 15.3 |
| NA (Dimer of SL209) | 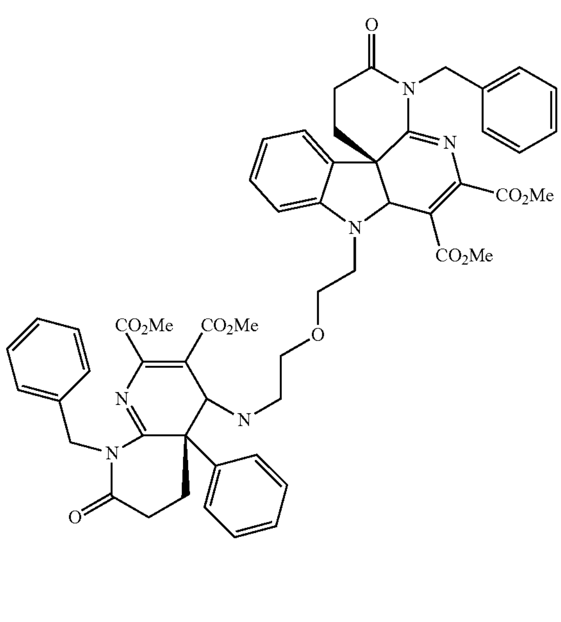 [SMILES: COC(=O)C1=C(C(=O)OC)C(NCCOCCN2c3ccccc3[C@]34CCC(=O)N(Cc5ccccc5)C3=NC(C(=O)OC)=C(C(=O)OC)C24)[C@@]2(c3ccccc3)CCC(=O)N(Cc3ccccc3)C2=N1] | SL231 | 0.098 | >100* | 0.476 | 2.5 |

TABLE 3-continued
Summary of Activities for Inhibitors 1 and 15-17.
| CMLD ID | Structure | SL number | IC$_{50}$ [μM] | CC$_{50}$ [μM] | HCV 2A [μM] | |
|---|---|---|---|---|---|---|
| | | | | | T1 - EC$_{50}$ | T2 - EC$_{50}$ |
| NA | 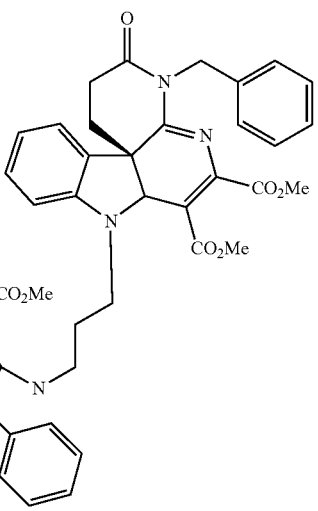 | SL235 | 2.9 | >36* | 0.088 | 0.735 |
| NA | 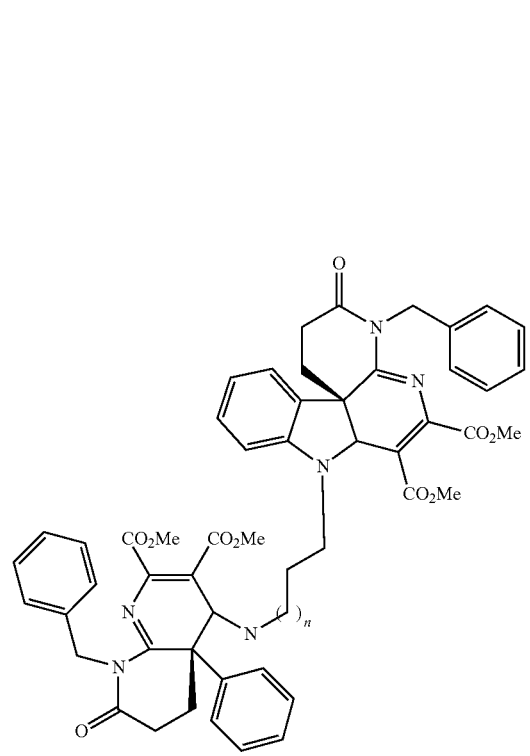 [SMILES: COC(=O)C1=C(C(=O)OC)C(NCCCN2c3ccccc3[C@]34CCC(=O)N(Cc5ccccc5)C3=NC(C(=O)OC)=C(C(=O)OC)C24)[C@@]2(c3ccccc3)CCC(=O)N(Cc3ccccc3)C2=N1] n = 2 | SL236 | 0.72 | >36* | 0.09 | 29.9 |

TABLE 3-continued

Summary of Activities for Inhibitors 1 and 15-17.

| CMLD ID | Structure | SL number | IC$_{50}$ [µM] | CC$_{50}$ [µM] | HCV 2A [µM] | |
|---|---|---|---|---|---|---|
| | | | | | T1 - EC$_{50}$ | T2 - EC$_{50}$ |
| NA | | SL250 | 0.092 | >100* | 1.4 | 1.1 |
| NA | | SL251 | 0.341 | 150 | 26.2 | 56.2 |

REFERENCES

All patents and other publications identified in the specification are expressly incorporated herein by reference for all purposes. These publications are provided solely for their disclosure prior to the filing date of the present application. Nothing in this regard should be construed as an admission that the inventors are not entitled to antedate such disclosure

We claims:

1. A compound having the structure shown in formula (I):

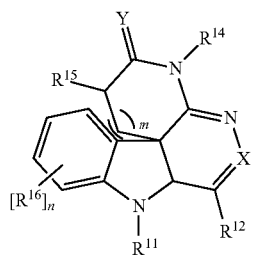

Formula (I)

wherein:
X is CR$^{13}$ or N;
Y is O or S;
R$^{11}$ is H, C(O)R$^{17}$, CO$_2$R$^{17}$, S(O)R$^{17}$, S(O)$_2$R$^{17}$, alkyl, alkenyl, alkynyl, acyl, aryl, heteroaryl, cyclyl, heterocyclyl, each of which can be optionally substituted, or R$^{11}$ is a linker that links two compounds of formula (I) together;
R$^{12}$ and R$^{13}$ are independently for each occurrence H, halogen, N(R$^{17}$)$_2$, NO$_2$, OR$^{17}$, CF$_3$, CN, C(O)R$^{17}$, CO$_2$R$^{17}$, SO$_3$R$^{17}$, SR$^{17}$, S(O)R$^{17}$, S(O)$_2$R$^{17}$, CH(CO$_2$R$^{17}$)$_2$, alkyl, alkenyl, alkynyl, acyl, aryl, heteroaryl, cyclyl or heterocyclyl, each of which can be optionally substituted;
R$^{14}$ is C(O)R$^{17}$, CO$_2$R$^{17}$, C(O)N(R$^{17}$)$_2$, S(O)R$^{17}$, S(O)$_2$R$^{17}$, alkyl, alkenyl, alkynyl, acyl, aryl, heteroaryl, cyclyl, heterocyclyl, each of which can be optionally substituted;
R$^{15}$ is H, halogen, CF$_3$, CN, —(CH$_2$)$_t$OR$^{17}$ (t is 1, 2, 3, 4, 5, 6, 7, 8, 9 or 10), C(O)R$^{17}$, CO$_2$R$^{17}$, OR$^{17}$, SR$^{17}$, S(O) R$^{17}$, S(O)$_2$R$^{17}$, alkyl, alkenyl, alkynyl, aryl, heteroaryl, cyclyl, heterocyclyl, each of which can be optionally substituted;
R$^{16}$ is independently for each occurrence halogen, N(R$^{17}$)$_2$, NO$_2$, OR$^{17}$, CF$_3$, CN, C(O)R$^{17}$, CO$_2$R$^{17}$, SO$_3$R$^{17}$, SR$^{17}$, S(O)R$^{17}$, S(O)$_2$R$^{17}$, CH(CO$_2$R$^{17}$)$_2$, alkyl, alkenyl, alkynyl, acyl, aryl, heteroaryl, cyclyl or heterocyclyl, each of which can be optionally substituted;
R$^{17}$ is independently for each occurrence H, alkyl, alkenyl, alkynyl, acyl, aryl, heteroaryl, cyclyl, or heterocyclyl, each of which can be optionally substituted
m is 1, 2, or 3;
n is 0, 1, 2, 3, or 4; and
stereoisomers and pharmaceutically acceptable salts thereof.

2. The compound of claim 1, wherein R$^{11}$ is selected from the group consisting of H, methyl, ethyl, propyl, butyl, pentyl, hexyl, allyl, but-2-ynyl, 3-methyl-but-2ynyl, benzyl, phenyl, hetp-6-ynyl,

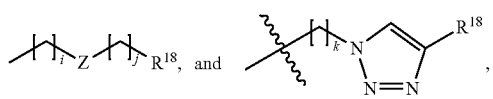

wherein i, j and k are independently an integer from 1 to 10; Z is O, S, NH or CH$_2$; and R$^{18}$ is optionally substituted alkyl, optionally substituted alkenyl, optionally substituted aryl, optionally substituted heteroaryl, optionally substituted cyclyl, or optionally substituted heterocyclyl.

3. The compound of claim 1, wherein at least one of R$^{12}$ and R$^{13}$ is selected from the group consisting of CO$_2$Me, CH$_3$, CF$_3$, SMe, CN, CH(CO$_2$Me$_2$)$_2$, aryl, heteroaryl and any combinations thereof.

4. The compound of claim 1, wherein R$^{14}$ is selected from the group consisting of

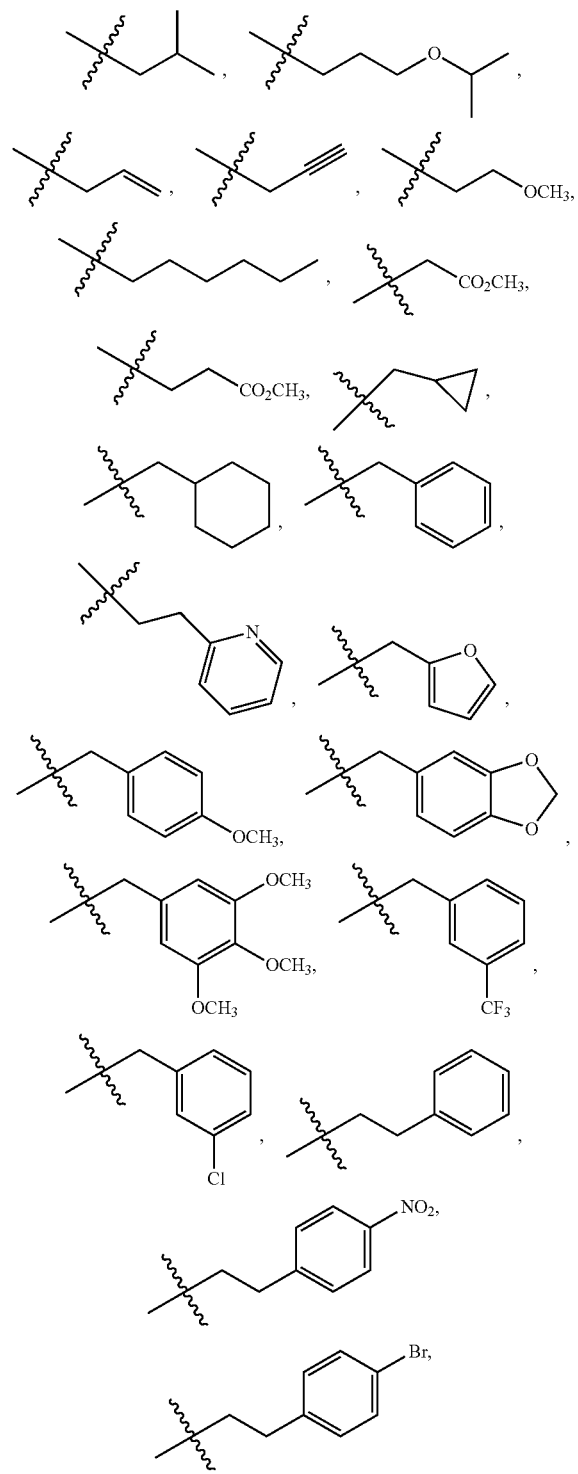

-continued

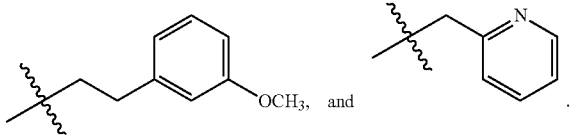 [SMILES: *CCc1cccc(OC)c1 ; "and" ; *Cc1ccccn1 ; "."]

5. The compound of claim 1, wherein $R^{15}$ is H.

6. The compound of claim 1, wherein $R^{16}$ is selected from the group consisting of OMe, $NH_2$, F, Br, I, Cl, CN, $CF_3$, $NO_2$, $CF_3$, —C≡CCH$_2$CH$_2$CH$_2$CH$_2$CH$_2$CH$_3$, —C≡CCH$_2$CH$_2$CH$_3$, —C≡CCH$_2$CH$_2$OH,

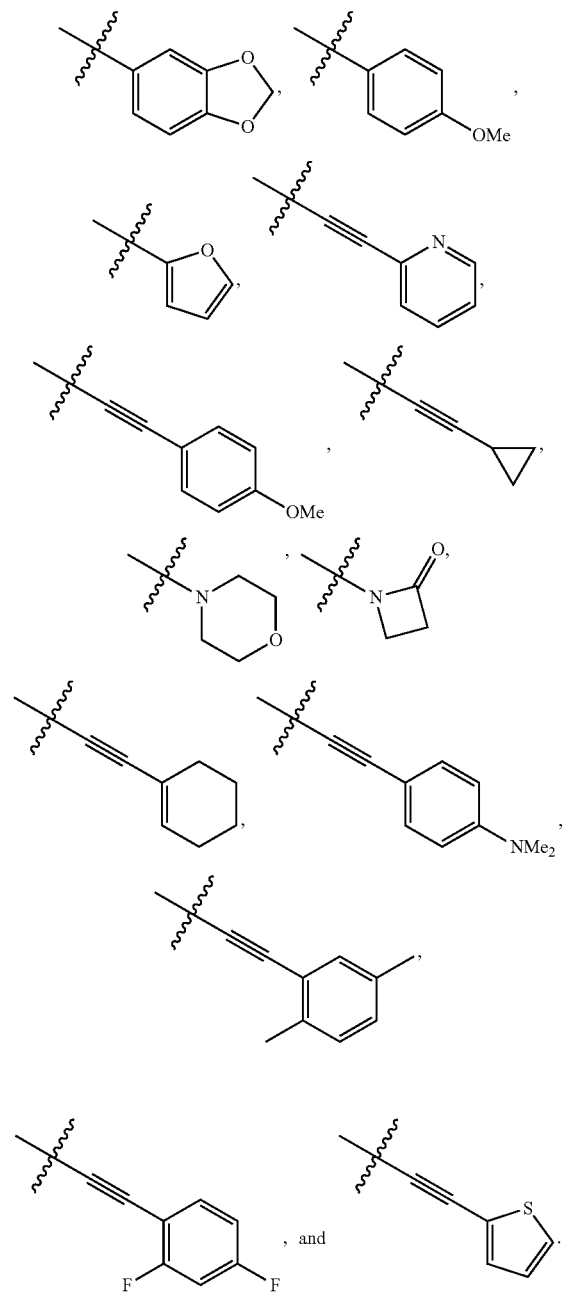

, and

7. The compound of claim 1, wherein the compound is of formula (Ic):

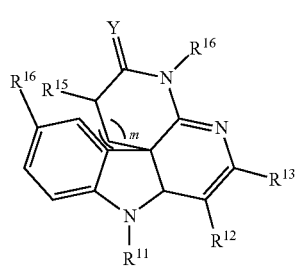

Formula (Ic)

8. A pharmaceutical composition comprising a compound of formula (I) and a pharmaceutically acceptable carrier wherein formula I comprises

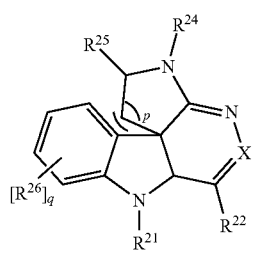

Formula (II)

wherein:

X is $CR^{13}$ or N;

Y is O or S;

$R^{11}$ is H, $C(O)R^{17}$, $CO_2R^{17}$, $S(O)R^{17}$, $S(O)_2R^{17}$, alkyl, alkenyl, alkynyl, acyl, aryl, heteroaryl, cyclyl, heterocyclyl, each of which can be optionally substituted, or $R^{11}$ is a linker that links two compounds of formula (I) together;

$R^{12}$ and $R^{13}$ are independently for each occurrence H, halogen, $N(R^{17})_2$, $NO_2$, $OR^{17}$, $CF_3$, CN, $C(O)R^{17}$, $CO_2R^{17}$, $SO_3R^{17}$, $SR^{17}$, $S(O)R^{17}$, $S(O)_2R^{17}$, $CH(CO_2R^{17})_2$, alkyl, alkenyl, alkynyl, acyl, aryl, heteroaryl, cyclyl or heterocyclyl, each of which can be optionally substituted;

$R^{14}$ is $C(O)R^{17}$, $CO_2R^{17}$, $C(O)N(R^{17})_2$, $S(O)R^{17}$, $S(O)_2R^{17}$, alkyl, alkenyl, alkynyl, acyl, aryl, heteroaryl, cyclyl, heterocyclyl, each of which can be optionally substituted;

$R^{15}$ is H, halogen, $CF_3$, CN, —$(CH_2)_tOR^{17}$ (t is 1, 2, 3, 4, 5, 6, 7, 8, 9 or 10), $C(O)R^{17}$, $CO_2R^{17}$, $OR^{17}$, $SR^{17}$, $S(O)R^{17}$, $S(O)_2R^{17}$, alkyl, alkenyl, alkynyl, aryl, heteroaryl, cyclyl, heterocyclyl, each of which can be optionally substituted;

$R^{16}$ is independently for each occurrence halogen, $N(R^{17})_2$, $NO_2$, $OR^{17}$, $CF_3$, CN, $C(O)R^{17}$, $CO_2R^{17}$, $SO_3R^{17}$, $SR^{17}$, $S(O)R^{17}$, $S(O)_2R^{17}$, $CH(CO_2R^{17})_2$, alkyl, alkenyl, alkynyl, acyl, aryl, heteroaryl, cyclyl or heterocyclyl, each of which can be optionally substituted;

$R^{17}$ is independently for each occurrence H, alkyl, alkenyl, alkynyl, acyl, aryl, heteroaryl, cyclyl, or heterocyclyl, each of which can be optionally substituted m is 1, 2, or 3;

n is 0, 1, 2, 3, or 4; and stereoisomers and pharmaceutically acceptable salts thereof.

9. A method of treating a disease or disorder caused by a Hepatitis C viral infection in a subject in need thereof, the method comprising administering to the subject a therapeutically effective amount of a compound of formula (I), wherein formula I comprises

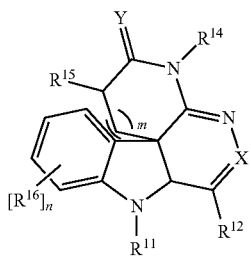

Formula (I)

wherein:

X is $CR^{13}$ or N;

Y is O or S;

$R^{11}$ is H, $C(O)R^{17}$, $CO_2R^{17}$, $S(O)R^{17}$, $S(O)_2R^{17}$, alkyl, alkenyl, alkynyl, acyl, aryl, heteroaryl, cyclyl, heterocyclyl, each of which can be optionally substituted, or $R^{11}$ is a linker that links two compounds of formula (I) together;

$R^{12}$ and $R^{13}$ are independently for each occurrence H, halogen, $N(R^{17})_2$, $NO_2$, $OR^{17}$, $CF_3$, CN, $C(O)R^{17}$, $CO_2R^{17}$, $SO_3R^{17}$, $SR^{17}$, $S(O)R^{17}$, $S(O)_2R^{17}$, $CH(CO_2R^{17})_2$, alkyl, alkenyl, alkynyl, acyl, aryl, heteroaryl, cyclyl or heterocyclyl, each of which can be optionally substituted;

$R^{14}$ is $C(O)R^{17}$, $CO_2R^{17}$, $C(O)N(R^{17})_2$, $S(O)R^{17}$, $S(O)_2R^{17}$, alkyl, alkenyl, alkynyl, acyl, aryl, heteroaryl, cyclyl, heterocyclyl, each of which can be optionally substituted;

$R^{15}$ is H, halogen, $CF_3$, CN, $-(CH_2)_tOR^{17}$ (t is 1, 2, 3, 4, 5, 6, 7, 8, 9 or 10), $C(O)R^{17}$, $CO_2R^{17}$, $OR^{17}$, $SR^{17}$, $S(O)R^{17}$, $S(O)_2R^{17}$, alkyl, alkenyl, alkynyl, aryl, heteroaryl, cyclyl, heterocyclyl, each of which can be optionally substituted;

$R^{16}$ is independently for each occurrence halogen, $N(R^{17})_2$, $NO_2$, $OR^{17}$, $CF_3$, CN, $C(O)R^{17}$, $CO_2R^{17}$, $SO_3R^{17}$, $SR^{17}$, $S(O)R^{17}$, $S(O)_2R^{17}$, $CH(CO_2R^{17})_2$, alkyl, alkenyl, alkynyl, acyl, aryl, heteroaryl, cyclyl or heterocyclyl, each of which can be optionally substituted;

$R^{17}$ is independently for each occurrence H, alkyl, alkenyl, alkynyl, acyl, aryl, heteroaryl, cyclyl, or heterocyclyl, each of which can be optionally substituted m is 1, 2, or 3;

n is 0, 1, 2, 3, or 4; and stereoisomers and pharmaceutically acceptable salts thereof.

* * * * *